(12) United States Patent
Bunch et al.

(10) Patent No.: US 10,702,181 B2
(45) Date of Patent: Jul. 7, 2020

(54) ATRIAL FIBRILLATION TREATMENT SYSTEMS AND METHODS

(71) Applicant: Intermountain Intellectual Asset Management, LLC, Salt Lake City, UT (US)

(72) Inventors: Thomas Jared Bunch, South Jordan, UT (US); John David Day, Salt Lake City, UT (US)

(73) Assignee: Intermountain Intellectual Asset Management, LLC, Salt Lake City, UT (US)

(*) Notice: Subject to any disclaimer, the term of this patent is extended or adjusted under 35 U.S.C. 154(b) by 236 days.

(21) Appl. No.: 15/994,842

(22) Filed: May 31, 2018

(65) Prior Publication Data

US 2019/0008405 A1     Jan. 10, 2019

Related U.S. Application Data

(63) Continuation of application No. 15/047,670, filed on Feb. 19, 2016, now Pat. No. 10,010,258, which is a continuation of application No. 13/923,348, filed on Jun. 20, 2013, now Pat. No. 9,295,399.

(60) Provisional application No. 61/798,456, filed on Mar. 15, 2013, provisional application No. 61/662,323, filed on Jun. 20, 2012, provisional application No. 61/799,242, filed on Mar. 15, 2013.

(51) Int. Cl.
*A61B 5/046* (2006.01)
*A61B 5/00* (2006.01)
*A61B 5/04* (2006.01)

(52) U.S. Cl.
CPC .......... *A61B 5/046* (2013.01); *A61B 5/04012* (2013.01); *A61B 5/6869* (2013.01); *A61B 5/7264* (2013.01)

(58) Field of Classification Search
CPC .... A61B 5/04525; A61B 5/046; A61B 5/7264
See application file for complete search history.

(56) References Cited

U.S. PATENT DOCUMENTS

| | | | |
|---|---|---|---|
| 5,676,153 A | 10/1997 | Smith et al. | |
| 5,868,680 A | 2/1999 | Steiner et al. | |
| 6,236,883 B1 | 5/2001 | Ciaccio et al. | |
| 6,622,042 B1 | 9/2003 | Thacker | |
| 7,117,029 B2 | 10/2006 | Stridh et al. | |
| 7,117,030 B2 | 10/2006 | Berenfeld et al. | |
| 7,187,973 B2 | 3/2007 | Hauck | |
| 7,189,208 B1 | 3/2007 | Beatty et al. | |
| 7,289,845 B2 | 10/2007 | Sweeney et al. | |

(Continued)

OTHER PUBLICATIONS

Extended European Search Report dated May 7, 2010 for EP06814447.6.

(Continued)

*Primary Examiner* — Joseph M Dietrich
(74) *Attorney, Agent, or Firm* — Stoel Rives LLP

(57) ABSTRACT

Methods for treating cardiac complex rhythm disorder in a patient can include receiving a plurality of electrical signals from a sensor system, wherein each electrical signal corresponds with a separate location on a cardiac wall of the heart of the patient, and wherein each electrical signal comprises an electrogram waveform; and ranking the electrical signals relative to each other based on at least a uniformity and a frequency of the electrogram waveform of each electrical signal.

20 Claims, 54 Drawing Sheets

(56) References Cited

U.S. PATENT DOCUMENTS

| | | | |
|---|---|---|---|
| 7,444,179 B2 | 10/2008 | Sherman et al. |
| 7,657,307 B2 | 2/2010 | Van Dam et al. |
| 7,729,753 B2 | 6/2010 | Kremliovsky et al. |
| 7,734,336 B2 | 6/2010 | Ghanem et al. |
| 7,801,594 B1 | 9/2010 | Higham |
| 7,930,020 B2 | 4/2011 | Zhang et al. |
| 8,165,666 B1 | 4/2012 | Briggs et al. |
| 8,175,702 B2 | 5/2012 | Efimov et al. |
| 8,340,766 B2 | 12/2012 | Ryu et al. |
| 9,295,399 B2 | 3/2016 | Bunch et al. |
| 2004/0059237 A1 | 3/2004 | Narayan et al. |
| 2004/0176696 A1 | 9/2004 | Mortara |
| 2004/0176697 A1 | 9/2004 | Kappenberger et al. |
| 2005/0165391 A1 | 7/2005 | Maguire |
| 2007/0239051 A1 | 10/2007 | Ghanem et al. |
| 2007/0299351 A1 | 12/2007 | Harlev |
| 2009/0299424 A1 | 12/2009 | Narayan |
| 2010/0026543 A1 | 2/2010 | Tsai et al. |
| 2010/0204592 A1 | 8/2010 | Hatib et al. |
| 2010/0324435 A1 | 12/2010 | Higham |
| 2011/0077540 A1 | 3/2011 | Belalcazar |
| 2011/0087121 A1 | 4/2011 | Zhang et al. |
| 2011/0251505 A1 | 10/2011 | Narayan et al. |

OTHER PUBLICATIONS

Extended European Search Report dated Oct. 1, 2011 for EP10181954.8.
International Search Report and Written Opinion dated Apr. 19, 2007 for international application PCT/US2006/035290.
International Search Report and Written Opinion dated Apr. 7, 2008 for international application PCT/US2007/069055.
International Search Report and Written Opinion dated Oct. 16, 2013 for international application PCT/US2013/046917.
Abreu, et al.,Effectiveness of the Maze Procedure Using Cooled-Tip Radiofrequency Ablation in Patients with Permanent Atrial Fibrillation and Rheumatic Mitral Valve Disease, Circulation 12(9-Supp):1-20-25, 2005.
Alessie, et al.,Electrical Contractile and Structural Remodeling During Atrial Fibrillation, Cardiovasc Res 54 (2):230-246, 2002.
Barber, et al.,The Quickhull Algorithm for Convex Hulls, ACM Trans on Mathematical Software, 22(4):469-483, Dec. 1996.
Bardy, et al.,Amiodarone or an Implantable Cardioverter—Defibrillator for Congestive Heart Failure, N Engl J Med 352(3):225-237, 2005.
Baykaner, et al.,Mapping and Ablating Stable Sources for Atrial Fibrillation: Summary for the Literature on Focal Impulse and Rotor Modulation, J Intery Card Electrosphysiol Mar. 20, 2014.
Baykaner, et al.,Targeted Ablation at Stable Atrial Fibrillation Sources Improves Success Over Conventional Ablation in High-Risk Patients: A Substudy of the Confirm Trial, Can J. Cardiol Oct. 2013, 29(1):1218-26.
Bunch, et al., Non-Final Office Action dated Mar. 13, 2015 for U.S. Appl. No. 13/923,348.
Bunch, et al., Notice of Allowance dated Mar. 20, 2018 for U.S. Appl. No. 15/047,670.
Bunch, et al., Notice of Allowance dated Nov. 20, 2015 for U.S. Appl. No. 13/923,348.
Bunch, et al., Office Action dated Aug. 28, 2017 for U.S. Appl. No. 15/047,670.
Bunch, et al., Office Action dated Jan. 30, 2017 for U.S. Appl. No. 15/047,670.
Calkins, et al.,HRS/EHRA/ECAS Expert Consensus Statement on Catheter and Surgical Ablation of Atrial Fibrillation: Recommendations for Personnel, Policy Procedures and Follow-Up, Report of the (HRS) Task Force on Catheter and Surgical Ablation of Atrial Fibrillation; (EHRA); (ECAS); (ACC); (AHA); (STS), Hearth Rhythm 4 (6):816-61, 2007.
Cappato, et al.,Prevalence and Causes of Fatal Outcome in Catheter Ablation of Atrial Fibrillation, J Am Coll Cardiol 53(19):1798-803, 2009.
Cappato, et al.,Worldwide Survey on the Methods, Efficacy, and Safety of Catheter Ablation for Human Atrial Fibrillation, Circulation 111(9):1100-1105, 2005.
Cheema, et al.,Long-Term Single Procedure Efficacy of Catheter Ablation of Atrial Fibrillation, J Interv Card Electrophysiol 15(3):145-155, 2006.
Cox, et al.,Cardiac Surgery for Arrhythmias, J Cardiovasc Electrophysiol 15:250-262, 2004.
Cox, et al.,The Central Controversy Surrounding the Interventional-Surgical Treatment of Atrial Fibrillation, J Thorac Cardiovasc Surg 129(1):1-4, 2005.
Eckstein, et al.,Transmural Conduction is the Predominate Mechanism of Breakthrough During Atrial Fibrillation: Evidence from Simultaneous Endo-Epicardial High-Density Activation Mapping, Circ Arrhythm Electrophusiol, 2013, 6 (2):334-41.
Ellis, et al.,Trends in Utilization and Complications of Catheter Ablation for Atrial Fibrillation in Medicare Beneficiaries, Hearth Rhythm, 6(9):1267-73, 2008.
Gaspo, et al.,Functional Mechanisms Underlying Tachycardia-Induced Sustained Atrial Fibrillation in a Chronic Dog Model, Circulation 96(11):4027-4035, 1997.
Hunter, et al.,Validation of a Classification System to Grade Fractionation in Atrial Fibrillation and Correlation with Automated Detection Systems, 11 Eurospace 2009, 1587.
Jarman, et al.,Spatiotemporal Behavior of High Dominant Frequency During Paroxysmal and Persistent Atrial Fribrillation in the Human Left Atrium, circ Arrythm electrophusiol, Aug. 1, 2012, 5(4):650-8.
Jones, et al.,Non-Invasive identification of Stable Rotors and Focal Sources for Human Atrial Fibrillation: Mechanisitc Classification of atrial Fibrillation from the Electrocardiogram, Eropace, Sep. 1, 2013, 15(9):1249-58.
Kalifa, et al.,Mechanisms of Wave Fractionation at Boundaries of High-Frequency Excitation in the Posterior Left Atrium of the Isolated Sheep Heart During Atrial Fibrilation, Circulation 113(5):626-633, 2006.
Knecht, et al.,Long Term Follow-Up of Idiopathic Ventricular Fibrillation Ablation: A Multicenter Study, J Am Coll Cardiol 54(6):552-528, 2009.
Warkides, et al.,New Mapping Technologies: An Overview with a Clinical Perspective, Journal of Interventional Cardiac Electrophysiology 13, 2005, 43-51.
Masse, et al.,Ventricular Fibrillation in Myopathic Human Hearts: Mechanistic Insights from in Vivo Global endocardial and Epicardial Mapping, Am J. Physiol Heart Circ Physiol 292(6):H2589-97, 2007.
Miyamoto, et al.,Characterization of Bipolar Electrograms During Sinus Rhythm for Complex Fractionalized Atrial Electrograms Recorded in Patients with Paroxysmal and Persistent Atrial Fibrillation, Europace, Apr. 2010, 12 (4):494-501.
Myerburg, et al.,Emerging Paradigms of the Epidemiology and Demographics of Sudden Cardiac Arrest, Hearth Thythm 3(2):235-239, 2006.
Nademanee, et al.,A New Approach for Catheter Ablation of Atrial Fibrillation: Mapping of the Electrophysiologic Substrate, J Am Coll Cardiol 43(11):2044-2053, 2004.
Nademanee, et al.,How to Perform Electrogram-Guided Atrial Fibrillation Ablation, Hearth Rhythm 2006, 981.
Narayan, et al.,Ablation of Rotor and Focal Sources reduces Late Recurrence of Atrial Fibrillation Compared to Trigger Ablation Alone, J Am Coll Cardiol, Feb. 28, 2014, pp. S0835-1097 (14) 01305-9.
Narayan, et al.,Direct or Coincidental Elimination of Stable Rotors or Focal sources May Explain Successful Atrial Fibrillation Ablation: On-Treatment Analysis of the Confirm Trial, J Am Coll Cardiol, Jul. 9, 2013, 62(2):138-47.
Narayan, et al.,Evaluating Fluctuations in Human Atrial Fibrillarory Cycle Length Using Monophasic Action Potentials, Pacing Clim Electrophysiol 29(11):1209-1218, 2006.
Narayan, et al.,Treatment of Atrial Fibrillation by the Ablation of Localized Sources: Confirm Trial, J Am Coll Cardiol, Aug. 14, 2012, 60(7):628-36.
Nash, et al.,Evidence for Multiple Mechanisms in Human Ventricular Fibrillation, Circulation 114:536-542, 2006.

(56) References Cited

OTHER PUBLICATIONS

Ng, et al.,Effect of Electrogram Characteristics on the Relationship of Dominant Frequency to Atrial Activation Rate in Atrial Fibrillation, Hearth Rhythm 3(11):1295-1305, 2006.
Ng, et al.,Technical Considerations for Dominant Frequency Analysis, J Cardiovasc Electrophysiol 18(7):757-64, 2007.
Oral, et al.,Radiofrequency Catheter Ablation of Chronic Atrial Fibrillation Guided by Complex Electrograms, Circulation 115(20):2606-12, 2007.
Oral, et al.,Randomized Assessment of the Incremental Role of Ablation of Complex Fractionated Atrial Electrograms after Antral Pulmonary Vein Isolation for Long-Lasting Persistent Atrial Fibrillation, J Am Coll Cardio 53 (9):782-9, 2009.
Orlov, et al.,Rotors of Truly Atypical Atrial Flutters Visualized by Firm Mapping and 3D-MRI Overlay on Live Fluoroscopy, J Intery Card Electrophysiol, Dec. 2013, 38(3):167.
Pachon, et al.,A New Treatment for Atrial Fibrillation Based on Spectral Analysis to Guide the Catheter RF-Ablation, Europace vol. 6, European Society of Cardiology 2004, 590-601.
Pachon, et al.,Cardioneuroablation—New Treatment for Neurocardiogenic Syncope, Functional AV Block and Sinus Dysfunction Using Catheter RF-Ablation, Europace, 2005, 7, 1-13, European Society of Cariology 2005, 1-13.
Ravelli, et al.,A Time-Domain Approach for the Identification of Atrial Fibrillation Drivers, Conf Proc IEEE Eng Med Biol Soc 2011, 2011:5527-30.
Ravelli, et al.,Anatomic Localization of Rapid Repetitive sources in Persistent Atrial Fibrillation: Fusion of Biatrial CT Images with Wave Similarity/Cycle Length Maps, JACC Cariovasc Imaging, Dec. 2012, 5(12):1211-20.
Reddy, et al.,Prophylactic Catheter Ablation for the Prevention of Defribrillator Therapy, N Engl J Med 357 (26):2657-65, 2007.
Ryu, et al.,Frequency Analysis of Atrial Electrograms Identifies Conductive Pathways from the Left to the Right Atrium during Atrial Fibrillation-Studies in Two Canine Models, J Cardiovasc Electrophusiol 2009, 20(6):677-74.
Ryu, et al.,Mapping of Atrial Activation During Sustained Atrial Fibrillation in Dogs with Rapid Ventricular Pacing Induced Heart Failure: Evidence for a Role of Driver Regions, J Cardiovasc Electriphysiol 2005, 16(12):1348-58.
Sahadevan, et al.,Epicardial Mapping of Chronic Atrial Fibrillation in Patients: Preliminary Observations, Circulation, 2004, 110(21):3293-9.
Sanders, et al.,Spectral Analysis Identifies Sites of High-Frequency Activity Maintaining Atrial Fibrillation in Humans, Circulation 112(6):789-797, 2005.
Shivkumar, et al.,Acute Termination of Human Atrial Fibrillation by Identification and Catheter Ablation of Localized Rotors and Sources: First Multicenter Experience of Focal Impulse and Rotor Modulation Firm Abalation, J Cardiovasc Electrophysiol, Dec. 2012, 23(12):1277-85.
Singh, et al.,Amiodarone Versus Sotalol for Atrial Fribrillation, N Engl J Med 352(18):1861-1872, 2005.
Skanes, et al.,Spatiotemporal Periodicity During Atrial Fibrillation in the Isolated Sheep Heart, Circulation 98 (12):1236-1248, 1998.
Tabereaux, et al.,Activation Patterns of Purkinje Fibers During Long-Duration Ventricular Fibrillation in an Isolated Canine Heart Model, Circulation 116(10):1113-9, 2007.
Teh, et al.,The Relationship Between Complex Fractionated Electrograms and Atrial Low-Voltage Zones During Atrial Fibrillation and Paced Thythm, Europace, 2011, 13(12):1709-16.
Vaquero, et al.,Cardiac Fibrillation: From Ion Channels to Rotors in the Human Heart, Hearth Rhythm, 2008.
Waldo, et al.,Inter-Relationships of Atrial Fibrillation and Atrial Flutter Mechanisms and Clinical Implications, J Am Coll Cardiol 51(8):779-86, 2008.
Warren, et al.,Blockade of the Inward Rectifying Potassium Current Terminates Ventricular Fibrillation in the Guine. Pig Heart, J Cardiovasc Electrophysiol 14(6):621-31, 2003.
Wijffels, et al.,Atrial Fibrillation Begets Atrial Fibrillation: A Study in Awake Chronically Instrumented Goats, Circulation 92:1954-1968, 1995.
Yamane, et al.,A Focal Source of Atrial Fibrillation in the Superior Vena Cava: Isolation and Elimination by Radiofrequency Ablation with the Guide of Basket Catheter Mapping, J Intery Card Electrophysiol, 2004, 11(2):131-4.
Zhou, et al.,Analysis of Epicardial Mapping Electrograms of Sustained Atrial Fibrillation Based on Shannon Etropy, Conf Proc IEEE Eng Med Biol Soc., 2009,2009:3470-2.

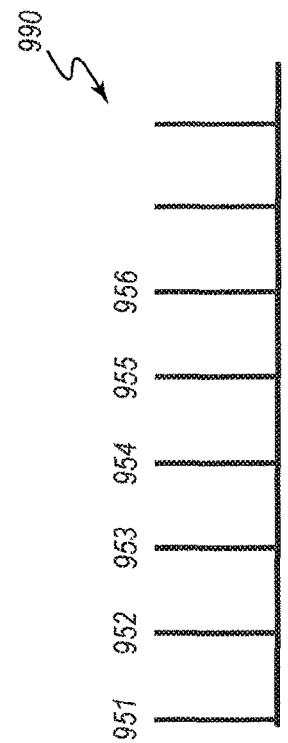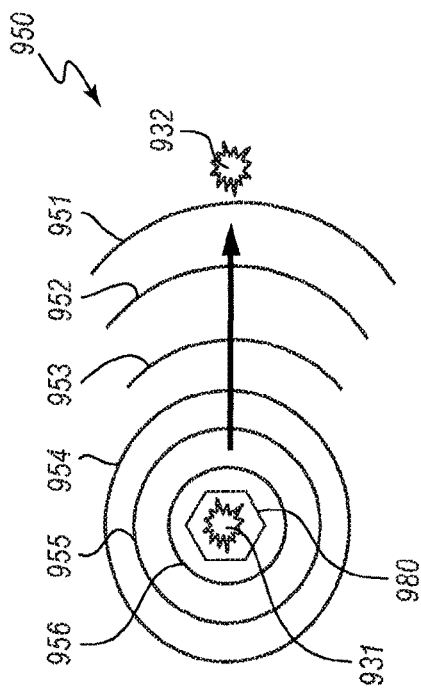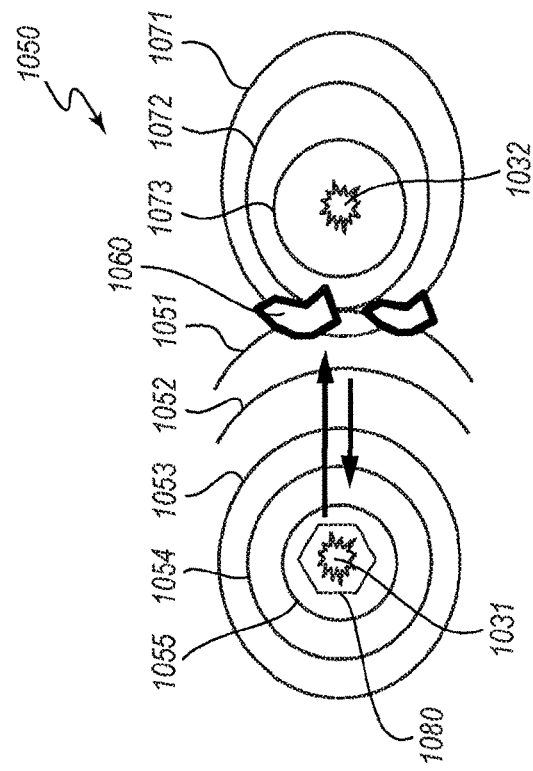

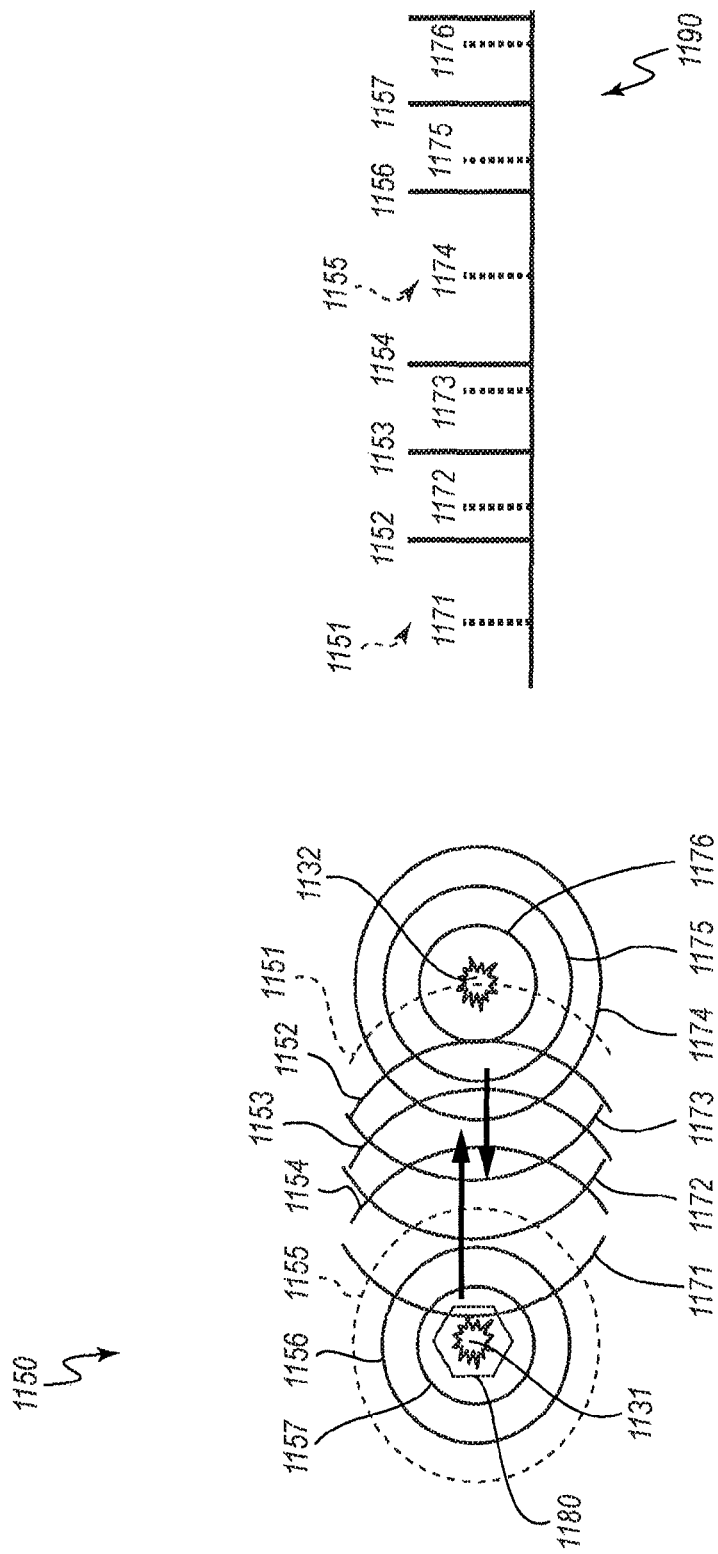

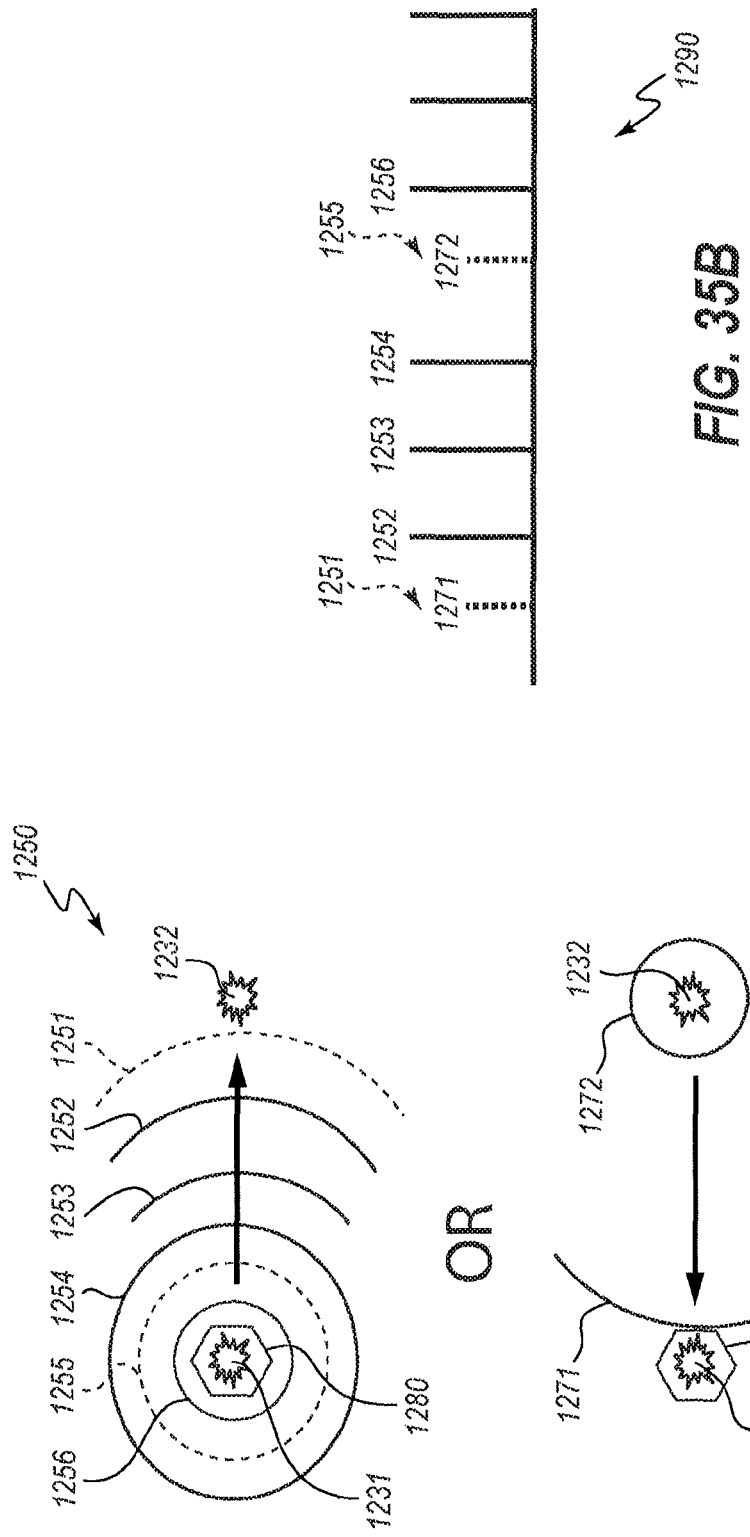

ATRIAL FIBRILLATION TREATMENT SYSTEMS AND METHODS

CROSS-REFERENCE TO RELATED APPLICATIONS

This application is a continuation of U.S. patent application Ser. No. 15/047,670, titled ATRIAL FIBRILLATION TREATMENT SYSTEMS AND METHODS, which was filed on Feb. 19, 2016, which is a continuation of U.S. patent application Ser. No. 13/923,348, now U.S. Pat. No. 9,295,399, titled ATRIAL FIBRILLATION TREATMENT SYSTEMS AND METHODS, which was filed on Jun. 20, 2013, and which claims the benefit under 35 U.S.C. § 119(e) of U.S. Provisional Patent Application No. 61/662,323, titled ATRIAL FIBRILLATION TREATMENTS, which was filed on Jun. 20, 2012; U.S. Provisional Patent Application No. 61/798,456, titled ATRIAL FIBRILLATION TREATMENTS, which was filed on Mar. 15, 2013; and U.S. Provisional Patent Application No. 61/799,242, titled UPSTREAM APPROACH FOR ABLATION OF ATRIAL FIBRILLATION, which was filed on Mar. 15, 2013, the entire contents of each of which are hereby incorporated by reference herein.

BACKGROUND

Atrial fibrillation ("AF") is a heart disease that affects a significant portion of the population of the United States (e.g., about 1 to 2 percent in the general population and up to about 10 percent in elderly populations). In a patient with AF, the electrical impulses that are normally generated by the sinoatrial node are overwhelmed by disorganized electrical activity in the atrial tissue, leading to an irregular conduction of impulses to the ventricles that generate the heartbeat. The result is an irregular heartbeat, which may be intermittent or continuous. In human populations, AF-induced irregular heartbeat is a significant source of stroke, heart failure, disability, and death.

There are a number of surgical options available for treating AF. One approach is known as the Cox-Maze III procedure. In this procedure, the left atrial appendage is excised, and a series of incisions and/or cryo- or radiofrequency-lesions are arranged in a maze-like pattern in the atria. The incisions encircle and isolate the pulmonary veins. The resulting scars block the abnormal electrical pathways, improving normal signal transmission and restoring regular heart rhythm. Less invasive techniques are also possible, which may use heating or cooling sources to create impulse-blocking lesions on the heart by ablation rather than incision.

Catheter-based radiofrequency ablation is a particularly common treatment for symptomatic AF, as it is less invasive than surgery. Whether this, or any of the foregoing treatments is used, however, there are certain drawbacks and/or limitations with known techniques. Embodiments discussed below can ameliorate, avoid, or resolve one or more of these drawbacks, as will be apparent from the present disclosure.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 7 is another schematic representation such as that of FIG. 6, but further including anatomical boundaries or scarred regions between the multiple atrial drivers, wherein the wavefronts are shown at a later time than those in FIG. 5, and wherein FIG. 7 illustrates that the atrial drivers generate primary wavefronts that ultimately collide and interact with the anatomic boundaries or scars to generate secondary wavefronts, further impacting the complexity and irregularity of the electrical wavelets.

FIG. 32A is a schematic representation of a portion of a cardiac substrate, or atrium wall, having a primary atrial driver that generates a regular series of wavefronts of electrical impulses that propagate toward a secondary atrial driver, which may also be referred to as a bystander driver, that is suppressed.

FIG. 32B is a schematic plot illustrating the electrical signals (point-based assessment of an electrical wave), or wavefronts or waveforms, detected at a region of the cardiac substrate designated by a hexagon in FIG. 32A illustrating that the signals generated by the driver are regular and have a predictable, repeated period.

FIG. 33A is a schematic representation of another portion of a cardiac substrate having a primary atrial driver that generates a regular series of wavefronts of electrical impulses that propagate toward a secondary atrial driver, wherein the secondary atrial driver is stable and not suppressed by the primary driver, and likewise generates a regular series of wavefronts of electrical impulses that propagate toward the primary atrial driver, wherein a frequency of the wavefronts produced by the secondary atrial driver is lower than a frequency of the wavefronts produced by the primary atrial driver.

FIG. 33B is a schematic plot illustrating the electrical signals (e.g., waveforms) detected at a region of the cardiac substrate designated by a hexagon in FIG. 33A illustrating that the signals generated by the drivers are regular and have a predictable, repeated period and neither set of waveforms produced by either driver suppresses operation of the other driver.

FIG. 34A is a schematic representation of another portion of a cardiac substrate having a primary atrial driver that generates a regular series of wavefronts of electrical impulses that propagate toward a secondary atrial driver, wherein the secondary atrial driver is stable and likewise generates a regular series of wavefronts of electrical impulses that propagate toward the primary atrial driver, wherein a frequency of the wavefronts produced by the secondary atrial driver is lower than a frequency of the wavefronts produced by the primary atrial driver, and wherein every third wavefront produced by the secondary atrial driver suppresses what would be every fourth wavefront of the primary driver.

FIG. 34B is a schematic plot illustrating the electrical signals (e.g., waveforms) detected at a region of the cardiac substrate designated by a hexagon in FIG. 34A demonstrating the periodic suppression of primary wavefronts due to activity of the stable secondary driver.

FIG. 35A is a schematic representation of another portion of a cardiac substrate having a primary atrial driver that generates a regular series of wavefronts of electrical impulses that propagate toward a secondary atrial driver, wherein the secondary atrial driver functions intermittently, and thus the two operational modes of the secondary driver are designated by alternative scenarios (as indicated by the recitation "OR"); wherein in the upper alternative, the secondary atrial driver is dormant, and thus the primary atrial driver is permitted to generate its electrical wavefronts, and in the lower alternative, the secondary atrial driver is temporarily active and generates a standalone or irregular wavefront that temporarily suppresses generation of a wavefront by the primary driver (which is indicated in the upper alternative by intermittent broken lines where wavefronts would be expected).

FIG. 35B is a schematic plot illustrating the electrical signals (e.g., waveforms) detected at a region of the cardiac substrate designated by a hexagon in FIG. 35A illustrating the periodic suppression of primary wavefronts due to activity of the intermittent secondary driver.

DETAILED DESCRIPTION

As noted above, many procedures for treating AF involve creating a pattern of lesions around the pulmonary veins so as to electrically isolate the pulmonary veins. Further lesion patterns may also be used to block other errant, irregular, problematic, or otherwise undesired electrical signals. The procedures are often quite lengthy and may be protracted or otherwise complicated when it is difficult to determine a location on the heart from which the problematic electrical signals emanate.

Catheter-based radiofrequency ablation is an example of an established treatment for symptomatic AF, and can involve the creation of lesions as just described. Success rates can vary depending on the AF subtype. For example, for paroxysmal AF, a success rate of 70%-85% may be common, as the disease predominantly involves pulmonary or great vein triggers. Stated otherwise, the high success rate may be achievable because the pulmonary or great vein triggers may be readily isolated by creating blocking lesions around the pulmonary veins. In contrast, persistent AF and longstanding persistent AF may have a lower success rate (e.g., 4%-60%), as the disease may involve not only primarily venous triggers, but also scars and/or multiple drivers within the left and right atria. As used herein, the term "driver" refers to any location, area, or region on or in the heart that is a source of AF signals. A driver can comprise, for example, a focal trigger, a substrate trigger, or a ganglion plexus; or stated otherwise, a driver can comprise a malfunctioning autonomic cell bundle. Drivers may also be referred to as focal drivers.

Disclosed herein are methods, systems, and devices for identifying, locating, and/or treating such drivers (e.g., malfunctioning autonomic cell bundles) to treat AF. In some embodiments, an electrophysiology apparatus is used to measure electrical activity occurring in a heart of a patient and/or to visualize the electrical activity and/or information related to the electrical activity. Other or further embodiments include a methodology for mapping the heart so as to identify a driver. Still further embodiments include a methodology for sorting or ranking electrograms to determine a position of a driver. Some embodiments include treating a patient via ablation at or near an identified driver. Various embodiments increase the effectiveness of AF treatment and/or reduce overtreatment of patients (e.g., by avoiding the creation of lengthy and/or complicated scars).

Figure 1:
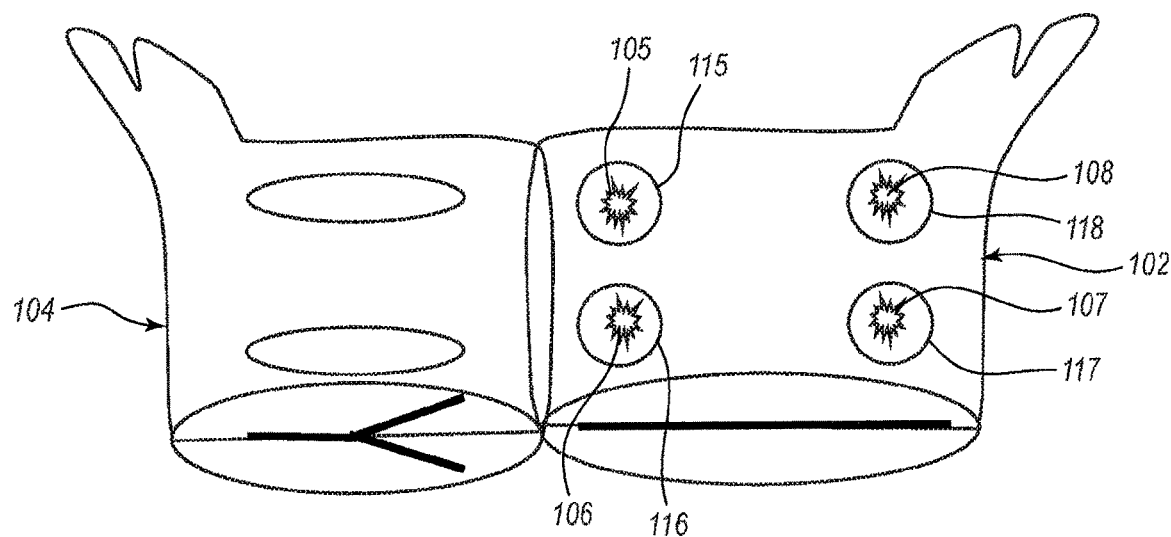
FIG. 1 is a schematic representation of a left and a right atrium with disordered electrical pulses emanating from the pulmonary veins, which may be described as paroxysmal atrial fibrillation.

FIG. 1 is a schematic representation of a left atrium 102 and a right atrium 104 with disordered electrical pulses emanating from drivers 105, 106, 107, 108 (which are schematically represented by starbursts) in the pulmonary veins 115, 116, 117, 118, respectively. FIG. 1 may be described as illustrating paroxysmal atrial fibrillation.

Figure 2:
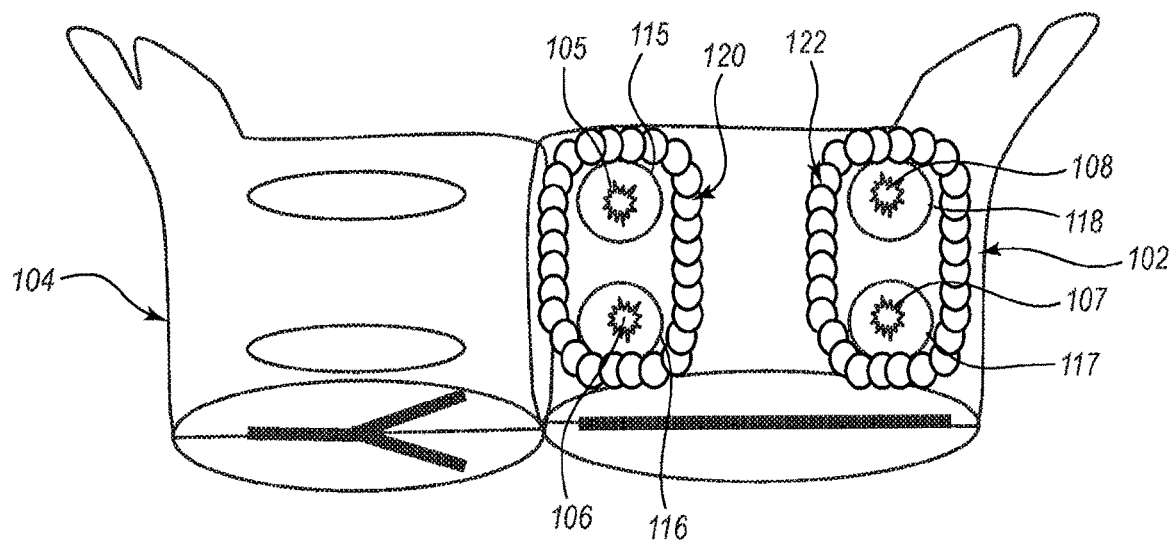
FIG. 2 is a schematic representation illustrating an ablative treatment for isolating the electrical pulses to resolve the disorder illustrated in FIG. 1.

FIG. 2 is a schematic representation illustrating an ablative treatment for isolating the electrical pulses to resolve the disorder illustrated in FIG. 1. In particular, a first ablation path 120 surrounds and isolates the drivers 105, 106 and the pulmonary veins 115, 116, and a second ablation path 122 surrounds and isolates the drivers 107, 108 and the pulmonary veins 117, 118.

Figure 3:
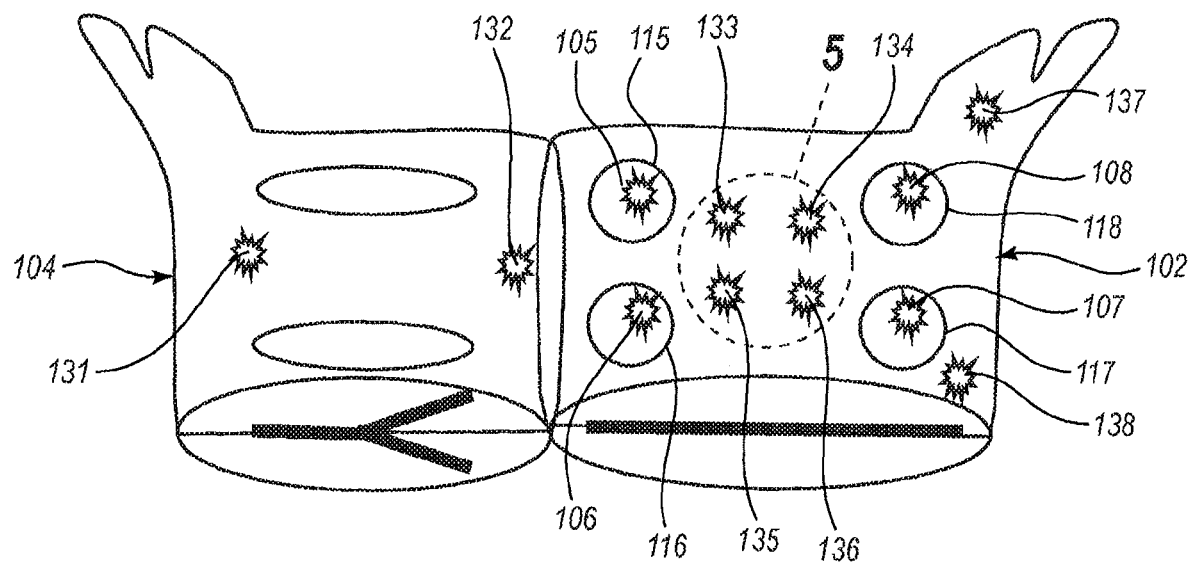
FIG. 3 is a schematic representation of a left and a right atrium with disordered electrical pulses emanating from the pulmonary veins and also emanating from the atrium wall, or cardiac substrate, which may be described as complex paroxysmal, persistent, or longstanding persistent atrial fibrillation.

FIG. 3 is a schematic representation of another example of a left atrium 102 and a right atrium 104 with disordered electrical pulses emanating from the pulmonary veins 115, 116, 117, 118 and also emanating from the atrium wall 124, or cardiac substrate. In particular, the disordered electrical pulses can emanate from multiple drivers 131, 132, 133, 134, 135, 136, 137, 138, as well as the drivers 105, 106, 107, 108. FIG. 3 may be described as illustrating persistent or longstanding persistent atrial fibrillation.

Figure 4:
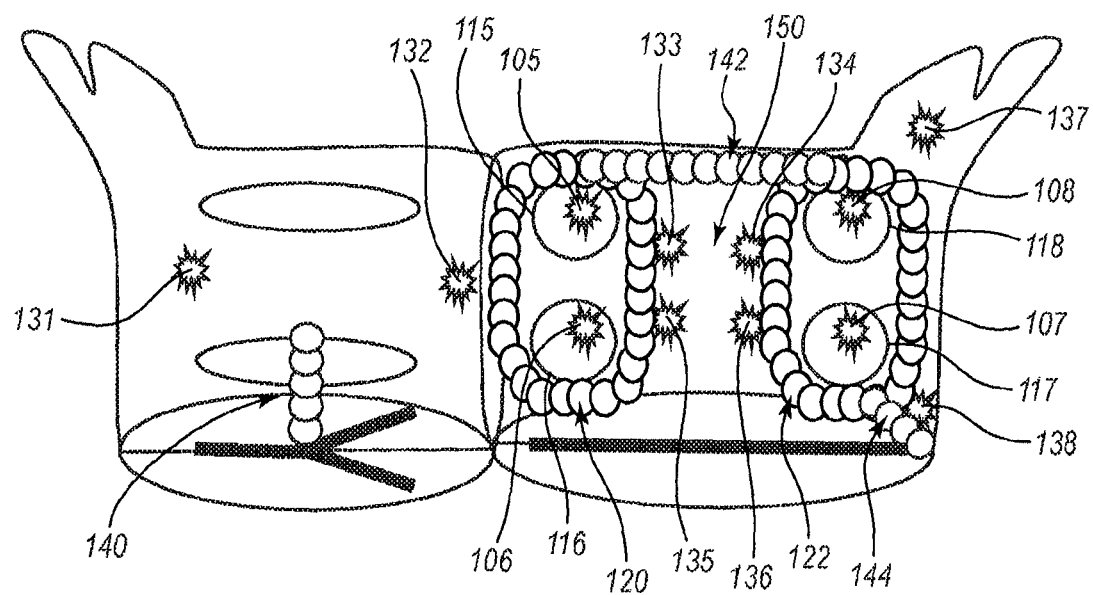
FIG. 4 is a schematic representation illustrating an ablative treatment for isolating sources of electrical pulses to resolve the cardiac complex rhythm disorder illustrated in FIG. 3; in some instances, the ablative treatment may be incomplete as drivers of atrial fibrillation may be missed (e.g., not isolated), depending on their location.

FIG. 4 is a schematic representation illustrating an ablative treatment for isolating sources of electrical pulses to resolve the cardiac complex rhythm disorder illustrated in FIG. 3. Ablation paths 120, 122 can be formed to isolate the pulmonary veins 115, 116 and 117, 118, respectively, along with their associated drivers 105, 106, 107, 108. One or more additional ablation paths 140, 142, 144 can also be formed. These ablation paths 140, 142, 144 can be used to block problematic electrical pulses emanating from the drivers 131, 132, 133, 134, 135, 136, 137, and 138.

Figure 12:
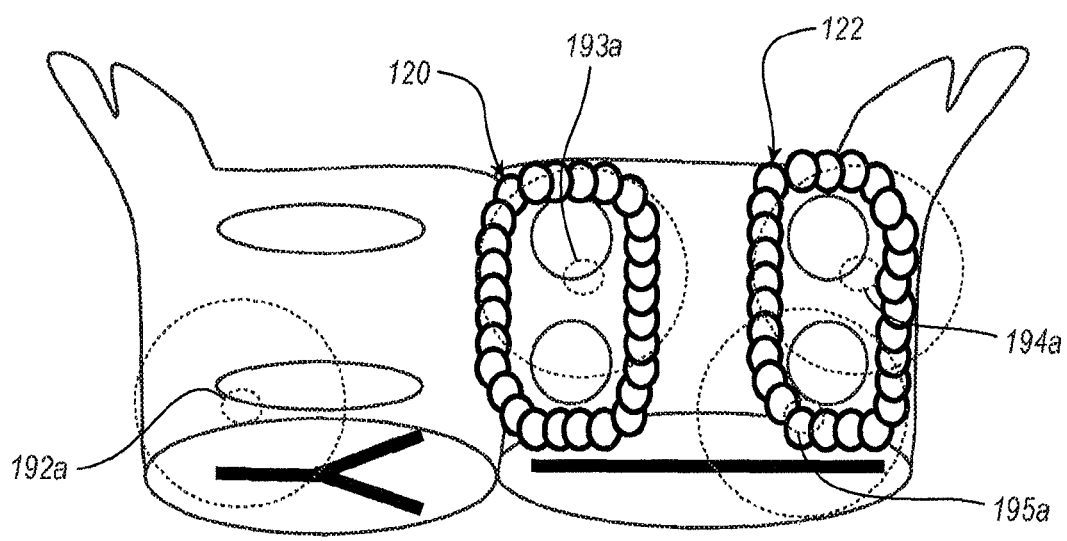
FIG. 12 is a schematic representation illustrating an atrial driver isolation procedure to electrically isolate three of the atrial drivers represented in FIG. 11 so as to prevent undesired signals from these drivers from propagating along the atrial wall.
Figure 13:
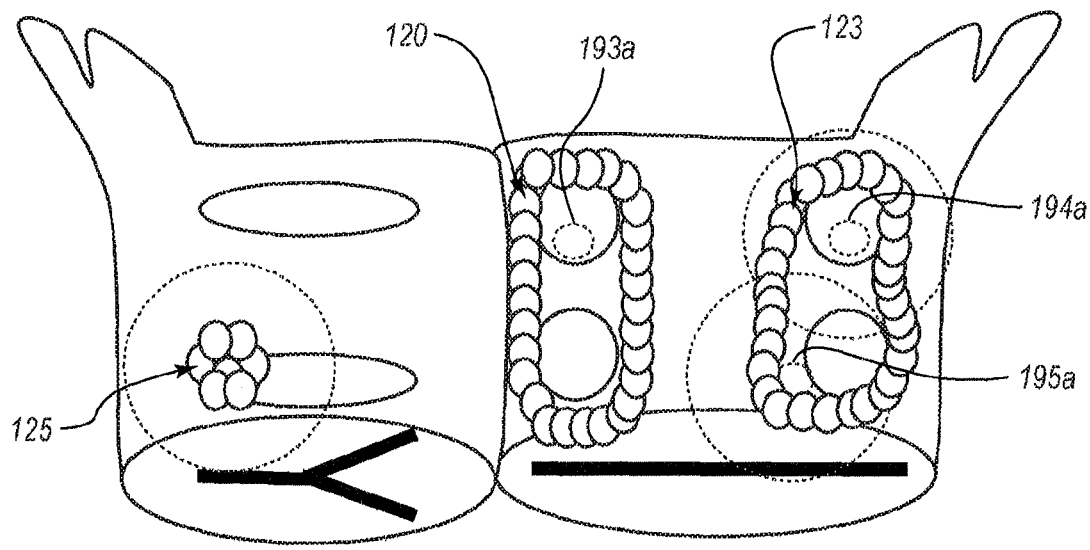
FIG. 13 is a schematic representation illustrating an atrial driver isolation procedure to electrically isolate two of the atrial drivers shown in FIG. 11 in a manner slightly different than that shown in FIG. 12, and further showing a focal ablation procedure to locally isolate a third atrial driver.

FIGS. 1-4 illustrate principles that are generally known. For example, the ablation paths 120, 122, 140, 142, 144 can be formed in any suitable manner. Standard ablation treatments may be used, such as limited pulmonary vein isolation (PVI), wide-area or antral pulmonary vein isolation (APVI), and/or complex fractionated atrial electrogram (CFAE) ablation. FIGS. 5-13, however, illustrate new and/or further approaches for treating cardiac complex rhythm disorders. FIGS. 5-10 illustrate concepts for locating problematic drivers on or within the heart, which can be treated in manners such as illustrated in FIGS. 12 and 13. While the concepts discussed with respect to FIGS. 5-10 can aid in explaining how or why certain methods and systems described herein may be effective, it is to be understood that these concepts are non-limiting. Stated otherwise, the present disclosure—including the disclosure of methods and systems for the treatment of AF—is not bound or limited by theories or explanations relative thereto that are set forth herein.

Figure 5:
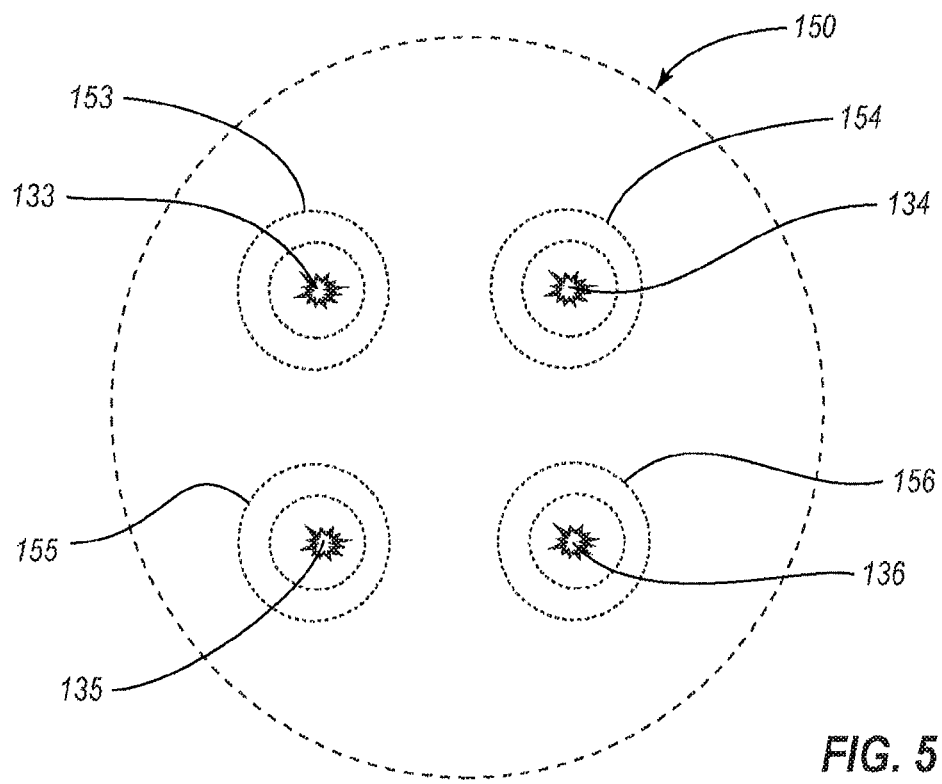
FIG. 5 is a schematic representation of a portion of the cardiac substrate, or atrium wall, having multiple atrial drivers that cause atrial fibrillation, particularly more complex types, wherein the atrial drivers generate wavefronts of electrical impulses; the wavefronts are shown in FIG. 5 at a time soon after formation, and the view of FIG. 5 is a schematic enlarged view of a portion of FIG. 3 taken along the view line 5 shown therein.

FIG. 5 is a schematic representation of a portion of the cardiac substrate 150, or atrium wall, having multiple atrial drivers 133, 134, 135, 136 that each generates multiple wavefronts of electrical impulses. Wavefronts 153, 154, 155, 156 are depicted as circles of a larger diameter, and additional wavefronts generated thereafter, which are depicted as circles at the interior of the wavefronts 153, 154, 155, 156. The drivers 133, 134, 135, 136 can cause atrial fibrillation, and the atrial wall can transmit the errant, erroneous, or irregular signal in the same manner that they conduct regular or desirable signals. The wavefronts detected via the electrograms can be used to identify the positions at which the undesired signals originate. In FIG. 5, the wavefronts 153, 154, 155, 156 are shown at a time soon after formation. The drivers 133, 134, 135, 136 can each be repetitive, each continually initiating stable wavefronts. Stated otherwise, the drivers 133, 134, 135, 136 may be stable so as to regularly generate electrical waveforms that propagate outwardly and that have stable or substantially constant periodicities.

Figure 6:
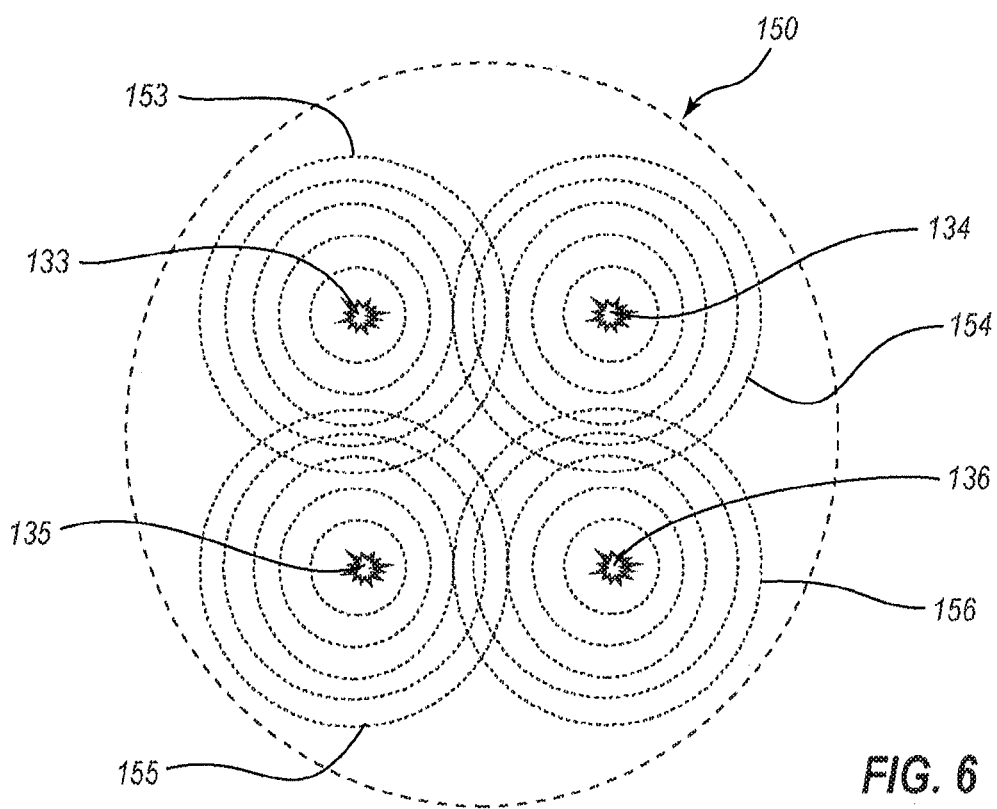
FIG. 6 is a schematic representation such as that of FIG. 5 illustrating the wavefronts at a later time, wherein wavefronts from various atrial drivers collide with each other, and this collision of wavefronts that were initiated by the drivers can lead to complex and fractionated electrical wavelets.

FIG. 6 is a schematic representation of a portion of the cardiac substrate 150, such as that of FIG. 5, illustrating the wavefronts 153, 154, 155, 156 at a later time. The wavefronts 153, 154, 155, 156 from corresponding atrial drivers 133, 134, 135, 136 collide with each other. As a result, portions of the cardiac substrate 150 positioned between the drivers 133, 134, 135, 136 encounter complex electrical signals. The signals may be noisy, and may be sporadic or irregular, as wavefronts from the multiple atrial drivers 133, 134, 135, 136 may arrive with irregular and/or offset timing.

Figure 7:
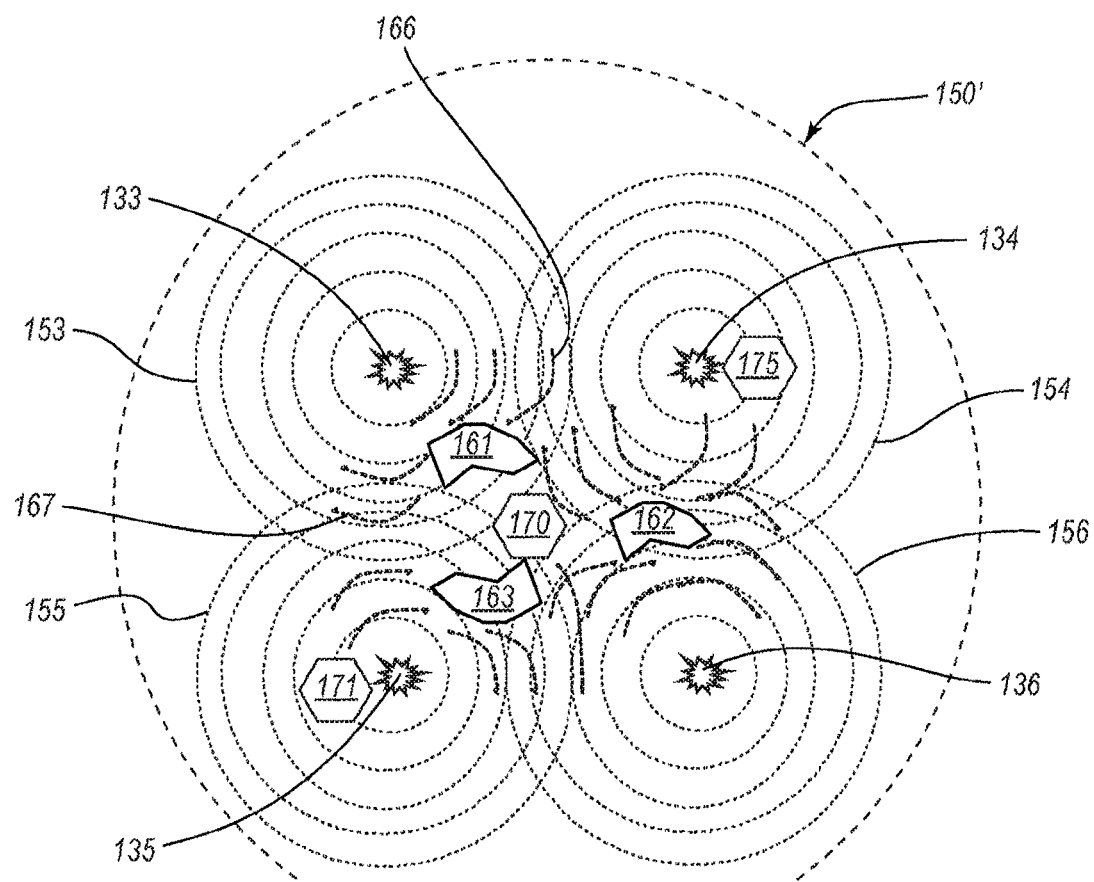

FIG. 7 illustrates a different cardiac substrate 150' that includes anatomical boundaries and/or damaged tissue 161, 162, 163 (e.g., scarred regions, such as from prior ablative procedures and/or degenerative heart ailment), which may more generally be referred to as boundary structures, between the multiple atrial drivers 133, 134, 135, 136. The primary wavefronts 153, 154, 155, 156 generated by the drivers 133, 134, 135, 136 can ultimately collide and interact with the boundary structures 161, 162, 163 to yield secondary wavefronts. For example, secondary wavefronts 166, 167 may result from interaction of a primary wavefront, which is generated by the driver 133, with the boundary structure 161. As a result, portions of the cardiac substrate 150' positioned between the drivers 133, 134, 135, 136 encounter complex electrical signals. The signals may be noisy, and may be sporadic or irregular, as wavefronts from the multiple atrial drivers 133, 134, 135, 136, as well as from the boundary structures 161, 162, 163 may arrive with irregular and/or offset timing.

Three regions or positions 170, 171, 175 in the cardiac substrate 150' are shown in FIG. 7. The positions are schematically represented by hexagons, although the regions may not necessarily be hexagonal in shape. The electrical signals encountered at the positions 170, 171 are illustrated in FIG. 8.

Figure 8:
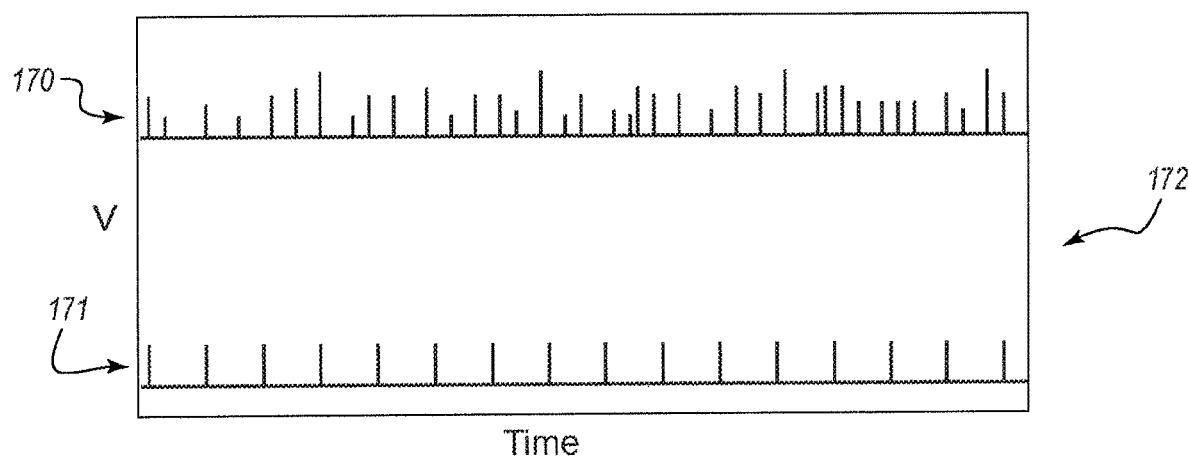
FIG. 8 is a schematic plot illustrating the electrical signals (point-based assessment of an electrical wave), or waveforms, detected at two different regions of the cardiac substrate shown in FIG. 7 across which the primary and/or secondary wavefronts travel, wherein the upper plot illustrates that the signals generated by collision of wavefronts, collision of wavefronts and scars, and/or collision of wavefronts and anatomic boundaries can be more complex and irregular, and wherein the lower plot illustrates that signals from the initial drivers can be rapid and relatively regular.
Figure 24:
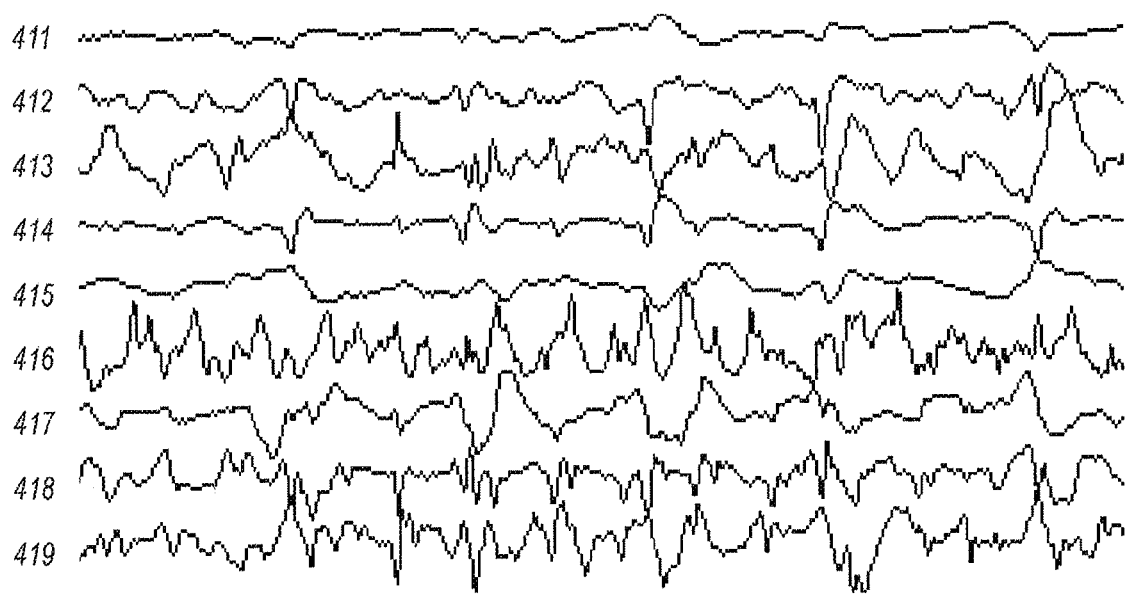
FIG. 24 is a display representing the cardiac signals, specifically electrograms, obtained via an arrangement such as shown in FIG. 23 and their identified associated regions on the cardiac substrate or atrial wall.

In particular, FIG. 8 is a schematic plot 172 illustrating the voltage V of the electrical signals, or waveforms, as a function of time, as detected at the positions 170, 171 of the cardiac substrate 150'. Although the waveforms are depicted with discrete pulses (e.g., showing a point-based assessment of an electrical wave), in other instances, the waveforms appear more wavelike (e.g., such as shown in FIG. 24). As can be appreciated from the plot that corresponds to the position 170, complex fractionated electrograms can be associated with regions of marked electrical variability. Stated otherwise, marked activation shifts can represent collisions of waveforms at a position that is remote from one or more drivers. Accordingly, more complex and/or irregular waveforms can be associated with regions that are remote from one or more drivers. As can be appreciated from the plot that corresponds to the position 171, waveforms that are stable (e.g., relatively regular) and that are rapid (e.g., have a high frequency) can be associated with regions that are at or near a driver.

Figure 9:
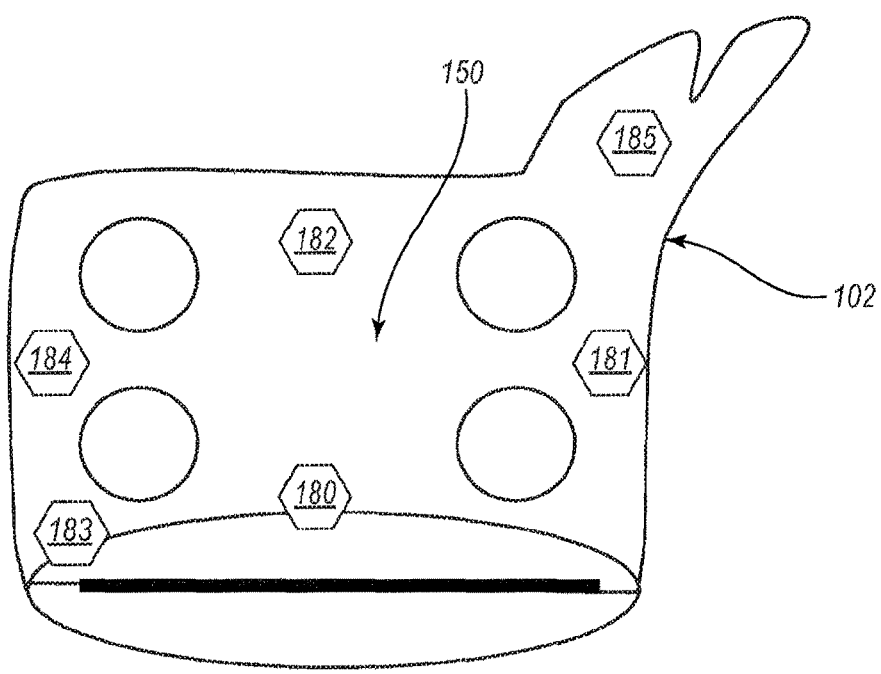
FIG. 9 is a schematic illustration of the left atrium, wherein electrical signals are detected at a plurality of regions.

FIG. 9 is a schematic illustration of the left atrium 102, wherein electrical signals are detected at a plurality of positions 180, 181, 182, 183, 184, 185. Any suitable system and/or device may be used to detect the signals at the plurality of positions. More or fewer positions may be detected than the six shown and/or the detections may be simultaneous. In other or further instances, detection of electrical signals at each of the positions may be carried out individually or in groups, such as by passing a sensor over one or more of the positions at a time.

Figure 16:
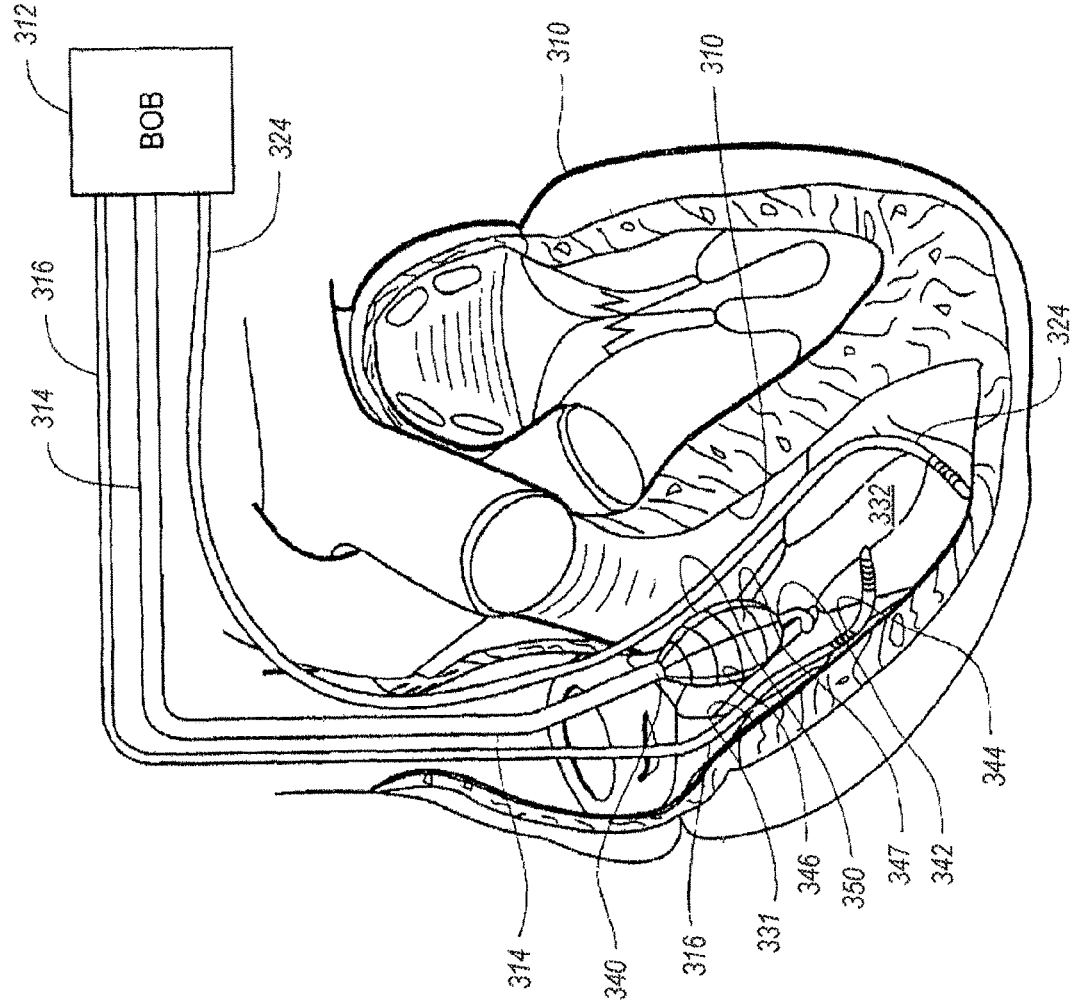
FIG. 16 is a schematic view of a portion of the system of FIG. 15 that includes a cutaway view of a heart of a patient and a perspective view of an embodiment of a non-contact multi-array sensor positioned in the right ventricle of the heart.
Figure 17:
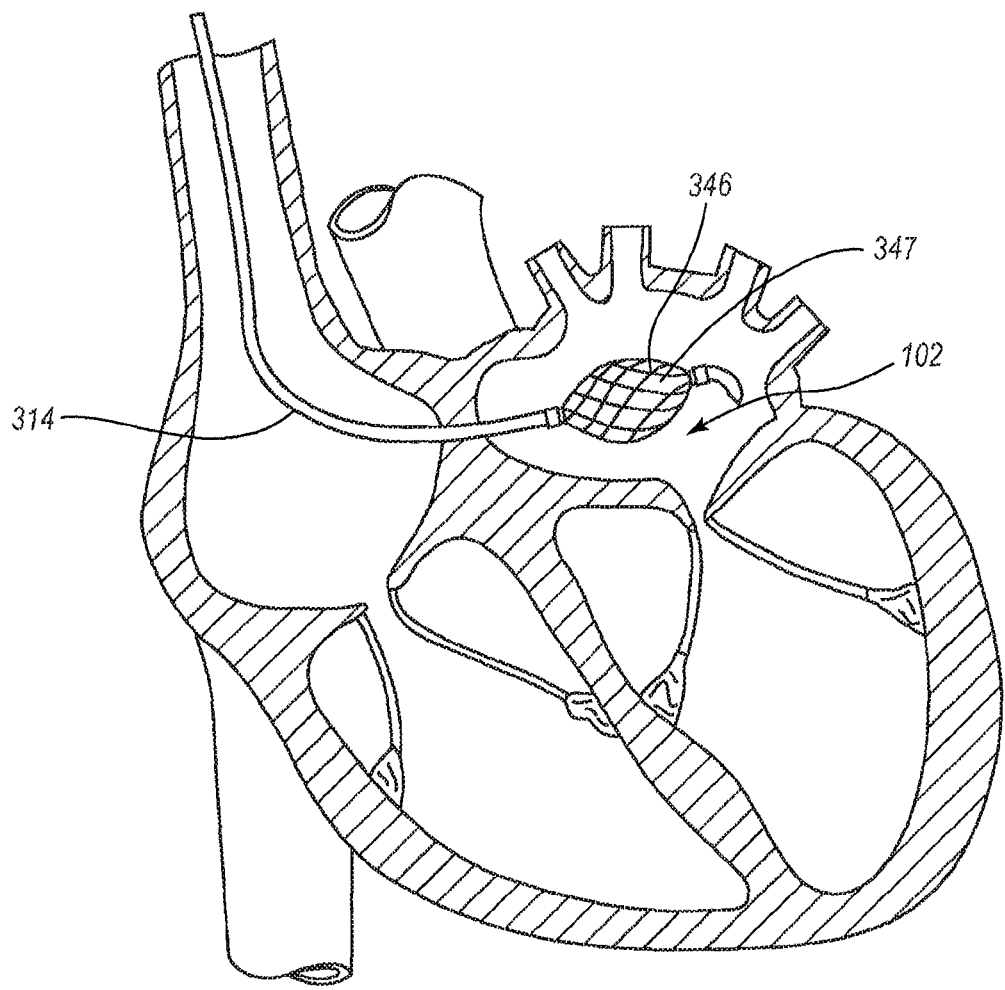
FIG. 17 is a schematic view, similar to FIG. 16, that includes a cross-sectional view of a heart of a patient and a perspective view of a depicts a portion of the system of FIG. 15 cross-sectional view of the non-contact multi-array sensor of FIG. 16 deployed in the left atrium of the heart.
Figure 18:
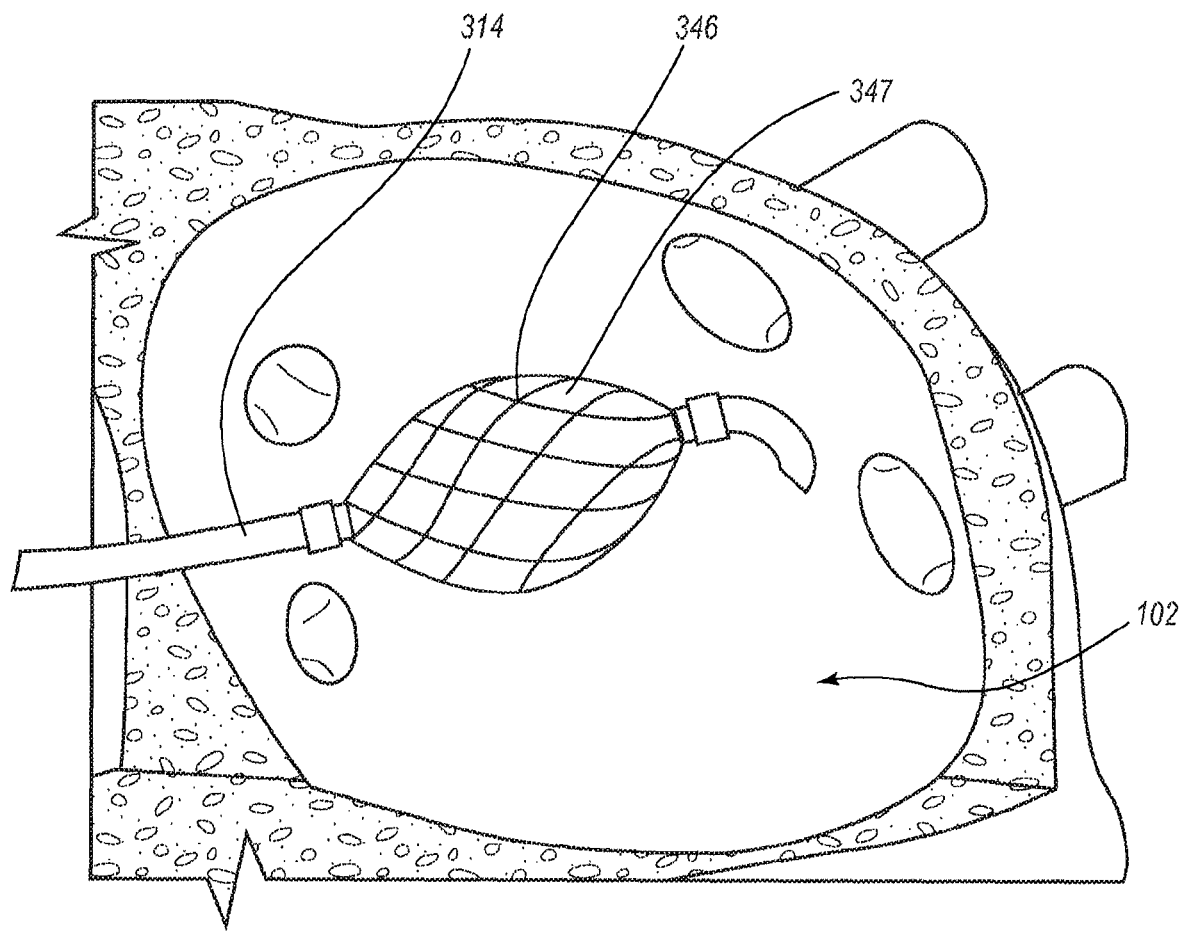
FIG. 18 is an enlarged cutaway view of the left atrium of the heart of a patient, similar to FIG. 17, which shows a non-contact multi-array sensor deployed in the left atrium.

Illustrative examples of sensing systems and devices that are suitable for detecting the electrical signals the correspond with the positions 180, 181, 182, 183, 184, 185 are discussed further below. For example, in some embodiments, a sensor, which may also be referred to as a sensor system or a or a sensor array, can be positioned within the left atrium 102. An illustrative example of such a sensor array is shown in FIGS. 16-18. The sensor array may be spaced from the inner atrial wall and may be capable of substantially simultaneously mapping electrical properties (e.g., electrogram waveforms) at numerous regions of the left atrium 102. The sensor array may similarly be positioned with the right atrium 104 to detect electrical signals corresponding to positions along the inner atrial wall of the right atrium 104. In some instances, the same sensor array is used in either atrium 102, 104, whereas in other embodiments, multiple sensor arrays may be used. The one or more sensor arrays may collect data from both atria 102, 104 simultaneously, or they may collect the data serially.

Figure 25A:
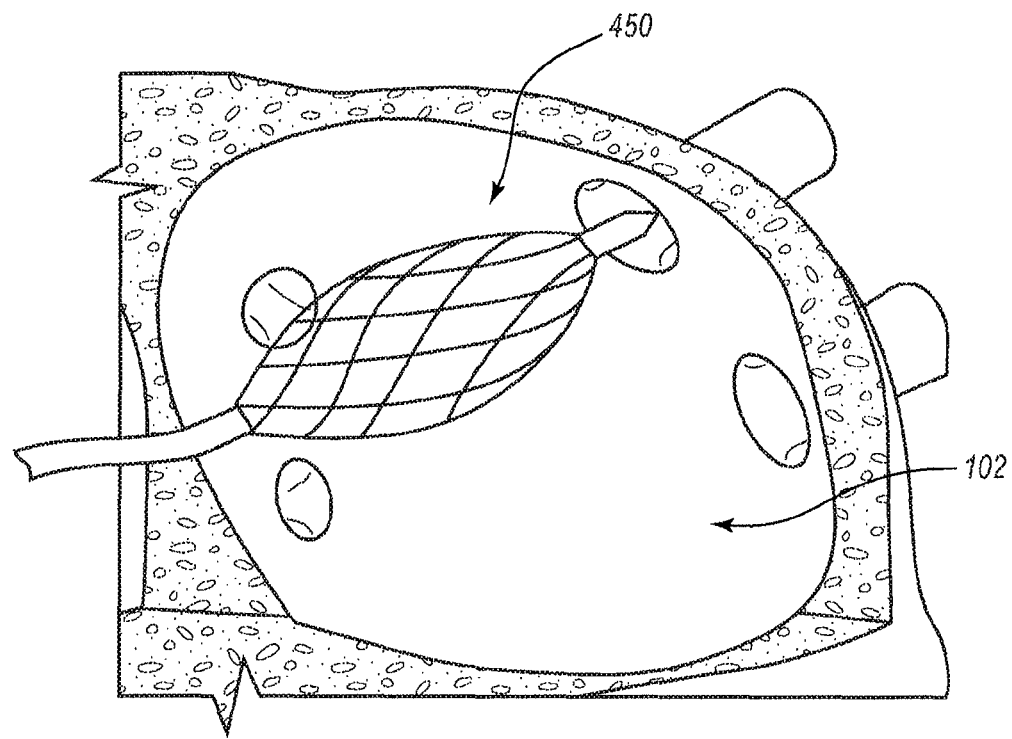
FIG. 25A is a schematic cross-sectional view of a portion of another embodiment of a system for identifying one or more atrial drivers, wherein the system includes a multi-sensor array that is shown in a constricted or non-deployed state.
Figure 25B:
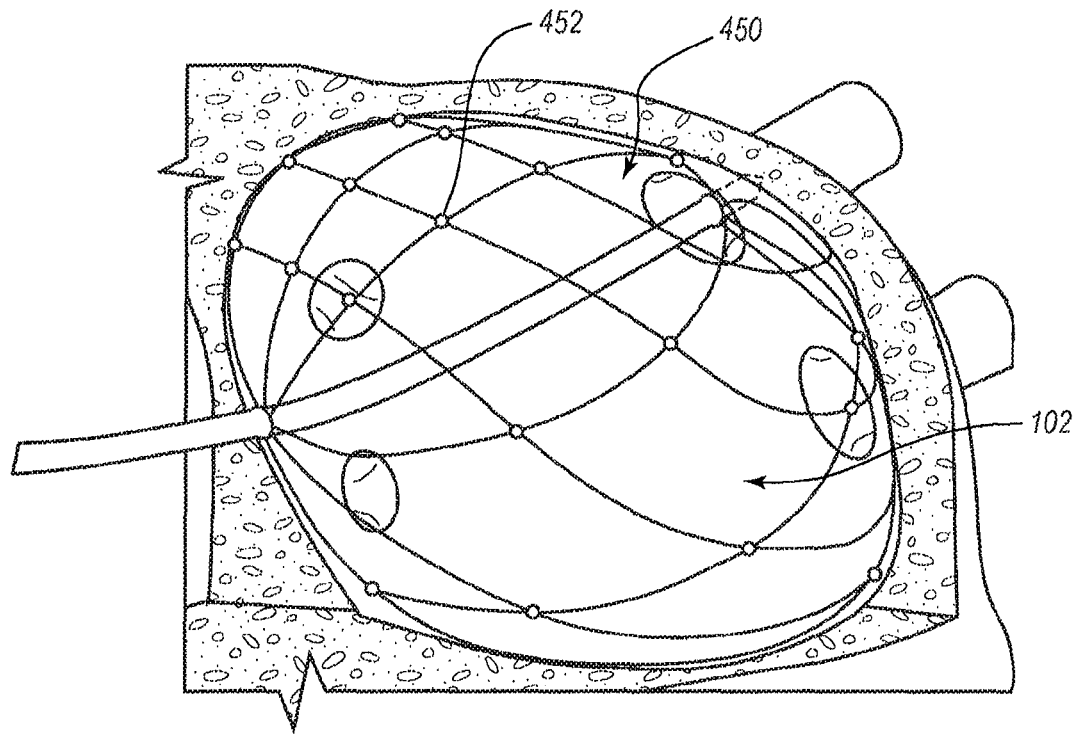
FIG. 25B is another schematic cross-sectional view of the portion of the system shown in FIG. 25A, wherein the multi-sensor array is in an expanded or deployed state such that sensors thereof are in contact with the atrial wall.

In other or further embodiments, a sensor system, such as one or more of the sensor arrays depicted in FIGS. 25A and 25B, may be positioned at the interior of the left atrium 102 and/or the right atrium 104, and the sensor system may include multiple sensors that are placed in contact with the inner atrial walls. The sensors may be configured to detect electrical signals conducted along the wall of the cardiac substrate over time (e.g., electrogram waveforms) at the portions of the atrial wall with which they are in contact.

In still other or further embodiments, electrical signals corresponding with a various portions of the cardiac substrate, such as the plurality of positions 180, 181, 182, 183, 184, 185 of FIG. 9, may be obtained via a sensor system having one or more sensors positioned at an exterior surface of the heart and/or protruding into a wall of the heart. For example, in some embodiments, one or more sensors may be positioned within the body of the patient and/or external to chambers of the heart.

Figure 26:
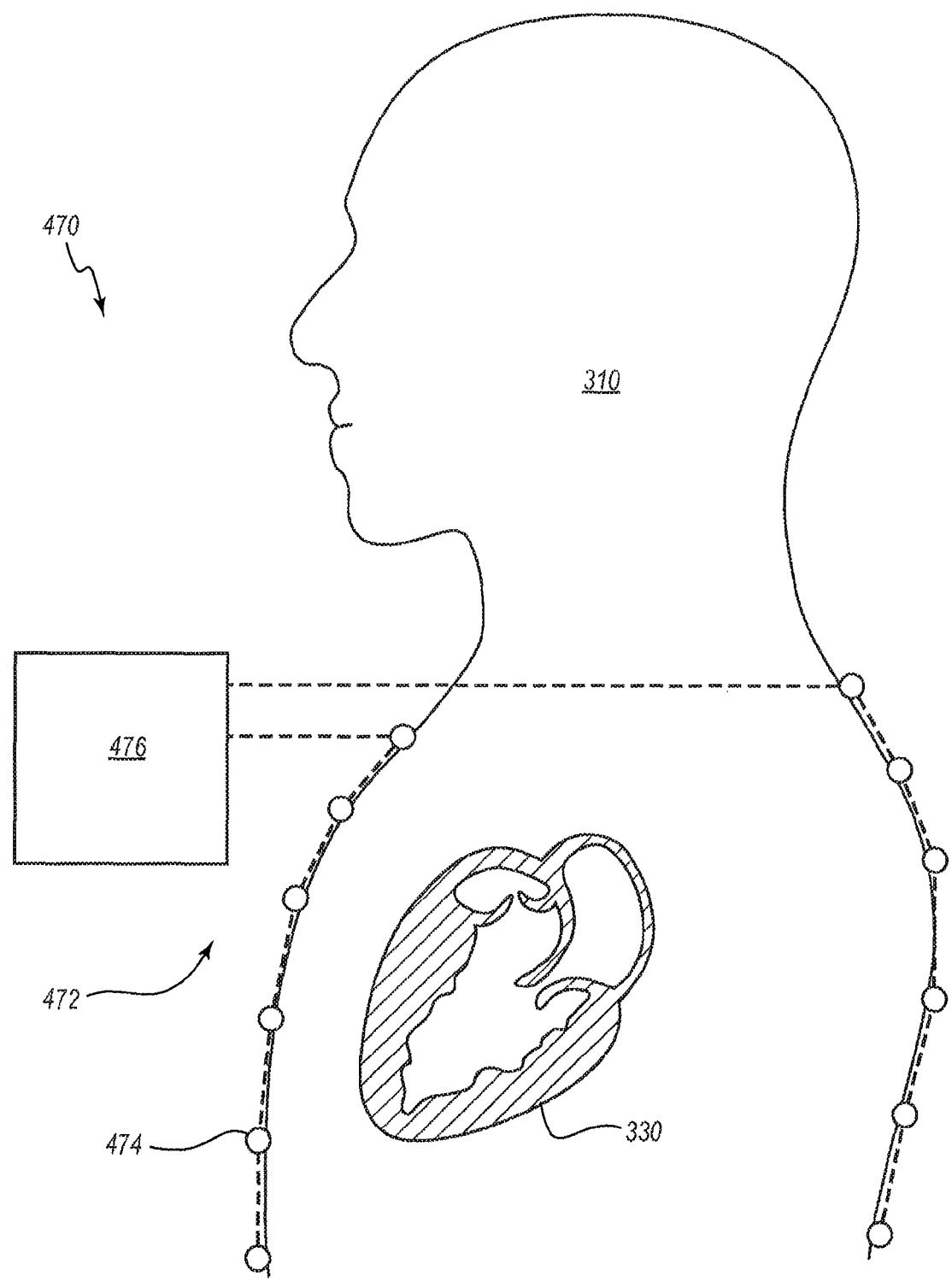
FIG. 26 is a schematic cross-sectional view of a portion of another embodiment of a system for identifying one or more atrial drivers, wherein the system includes a multi-sensor array that is positioned at an exterior of the patient.
Figure 27A:
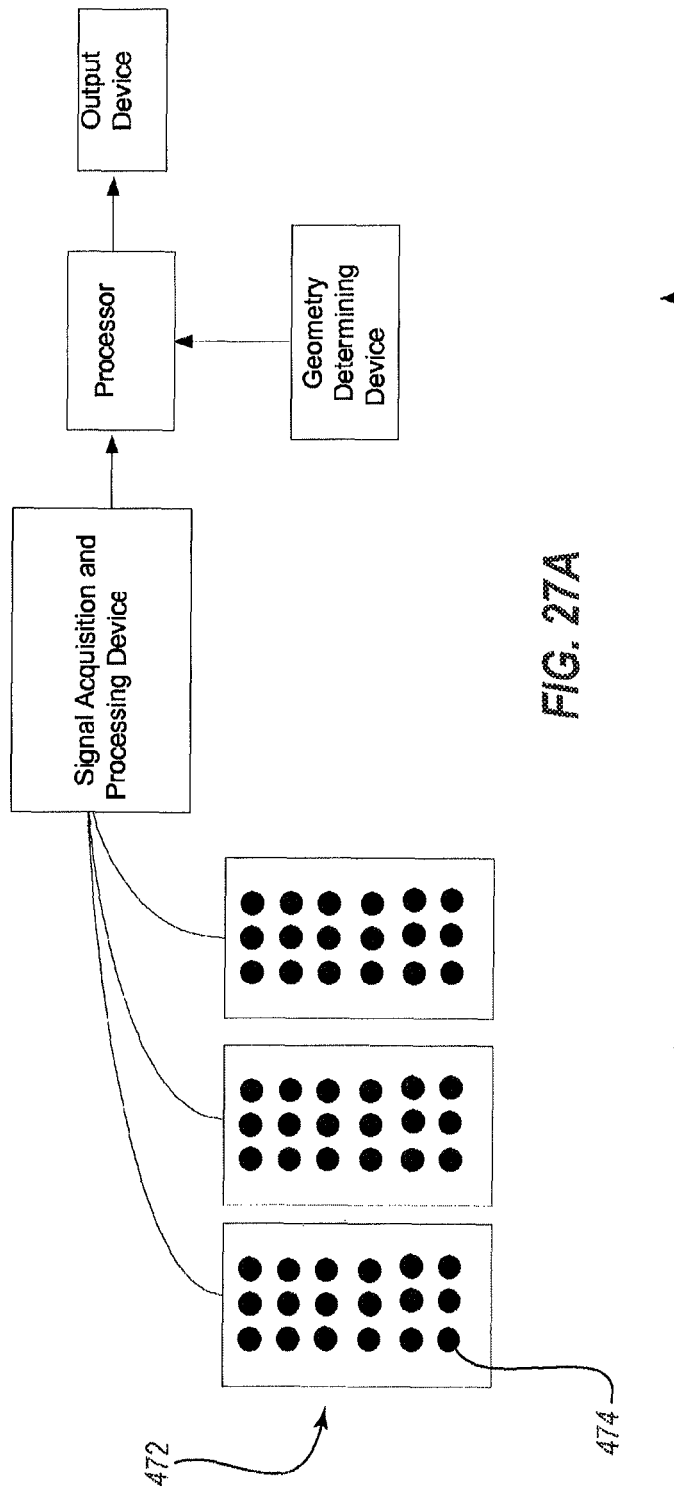
FIGS. 27A-27D depict illustrative instrumentation and methods for obtaining trace electrograms associated with the heart.
Figure 27C:
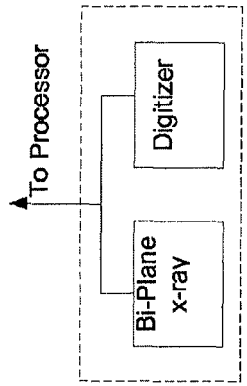
Figure 27B:
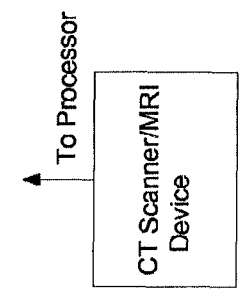
Figure 27D:
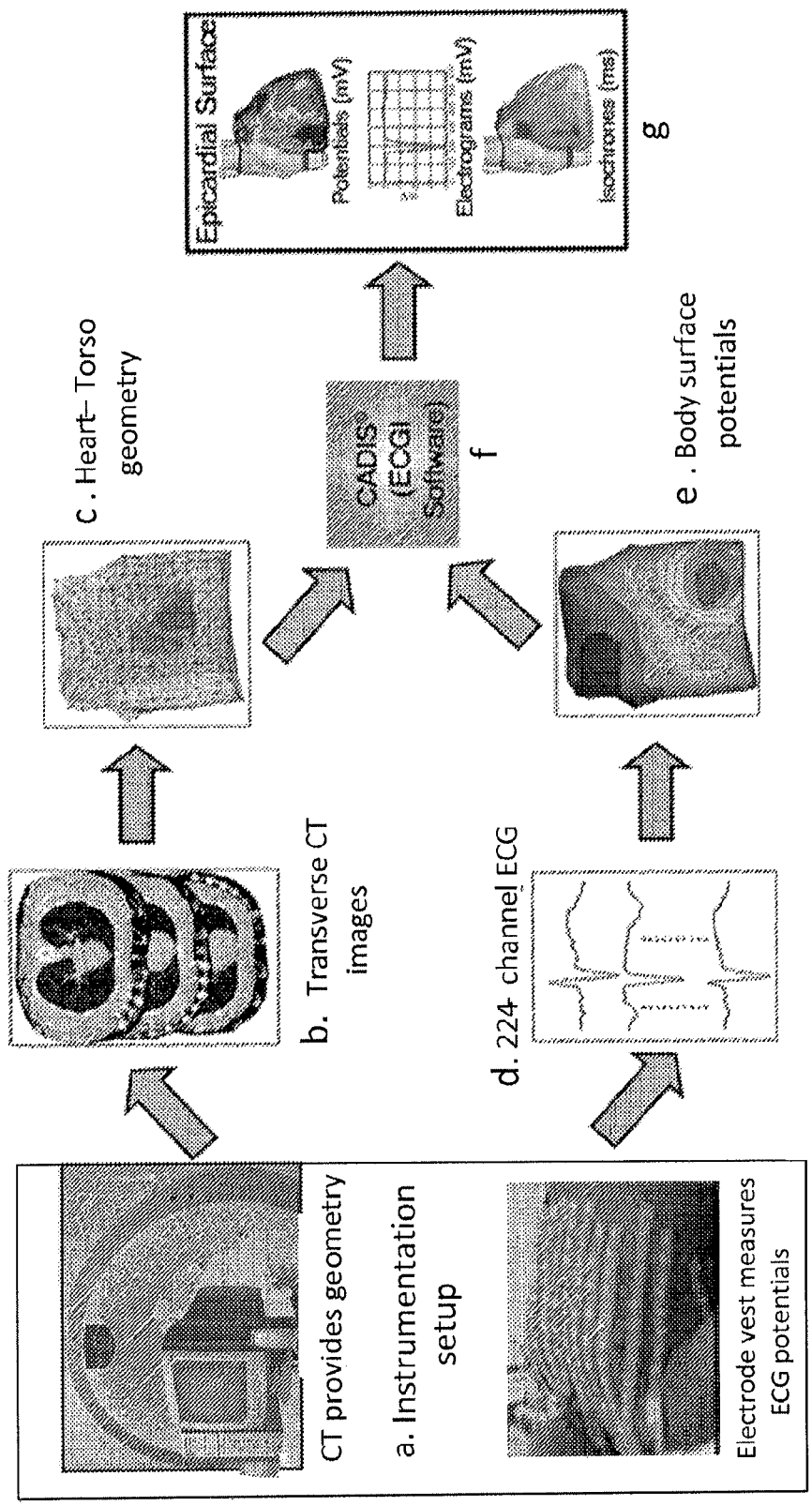

In other or further embodiments, electrical signals corresponding with a various portions of the cardiac substrate, such as the plurality of positions 180, 181, 182, 183, 184, 185 of FIG. 9, may be obtained via a sensor system positioned at an exterior of the patient, such as at the skin surface of the patient. One illustrative example of such a sensor system is depicted in FIG. 26. The sensor system may include skin electrodes or any other suitable sensor device or devices, and data collection via the sensors can include body surface mapping.

Figure 39:
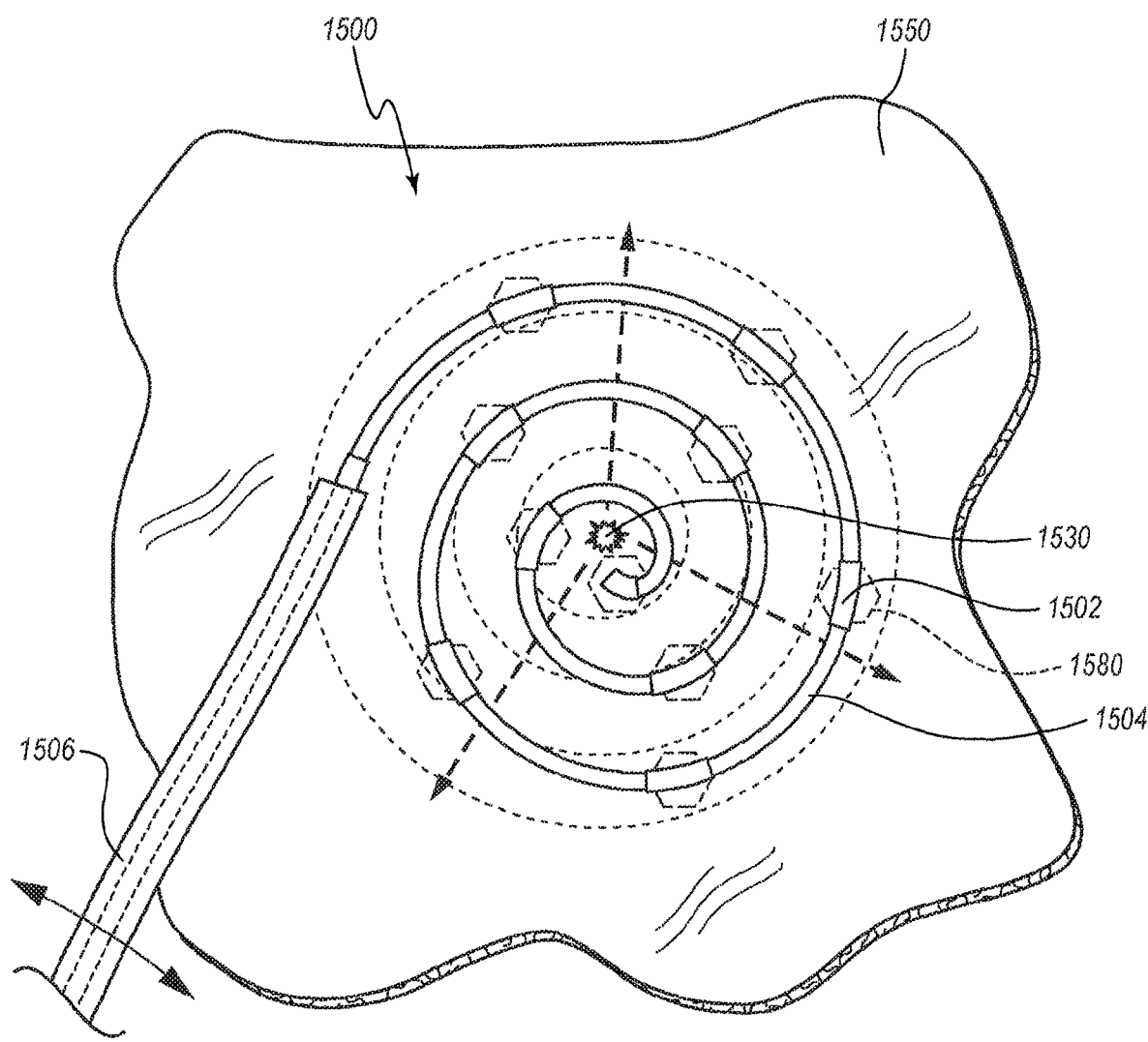
FIG. 39 is a plan view of an embodiment of a sensor assembly that includes multiple contact sensors that can extend along a cardiac substrate in at least two orthogonal directions, or stated otherwise, in at least two dimensions, to define at least a two-dimensional sensing area, wherein the sensor assembly is depicted in operation adjacent to a cardiac wall.
Figure 40:
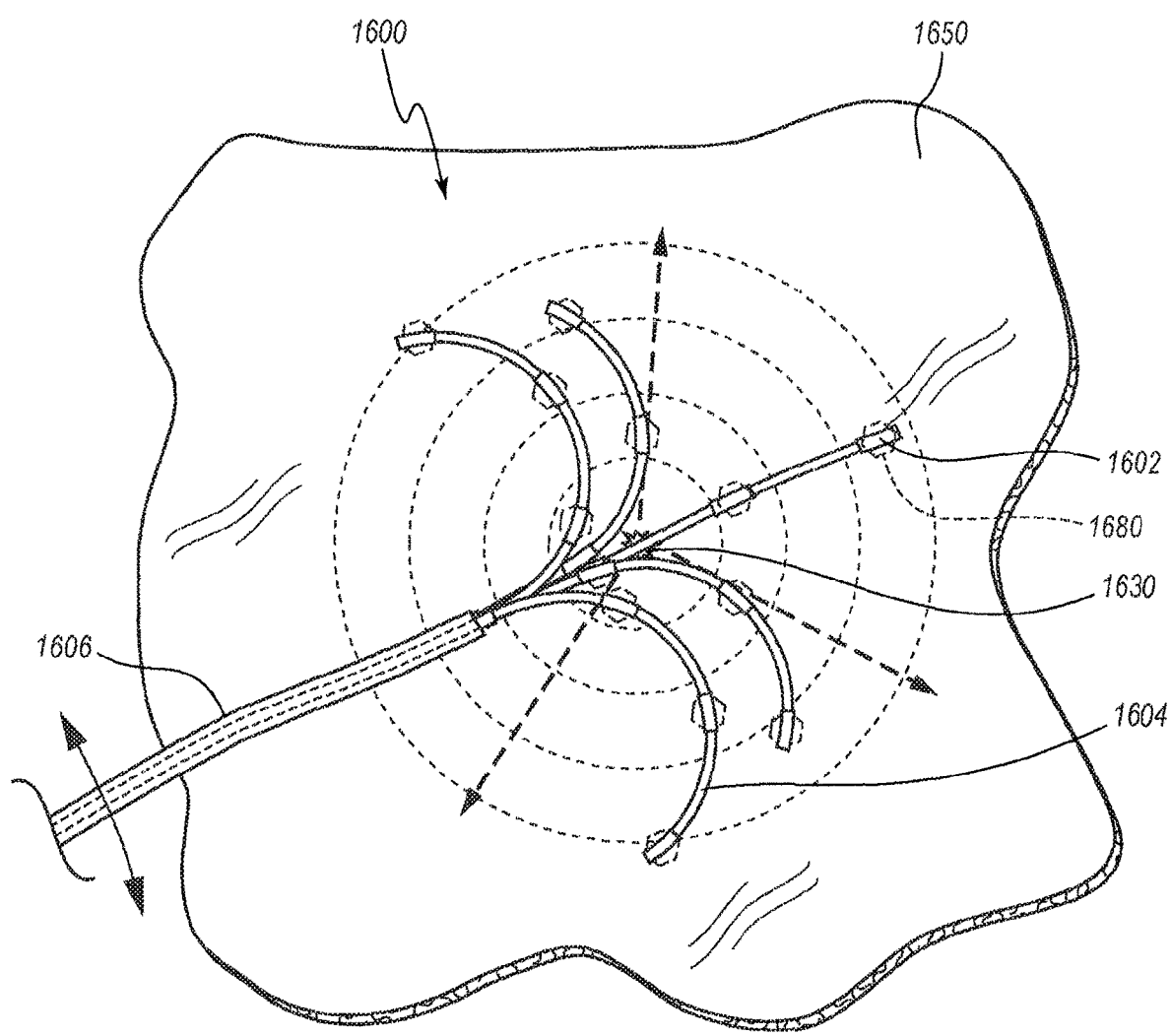
FIG. 40 is a plan view of another embodiment of a sensor assembly that includes multiple contact sensors that can extend along a cardiac substrate in at least two orthogonal directions, or stated otherwise, in at least two dimensions, to define at least a two-dimensional sensing area, wherein the sensor assembly is depicted in operation adjacent to a cardiac wall
Figure 43:
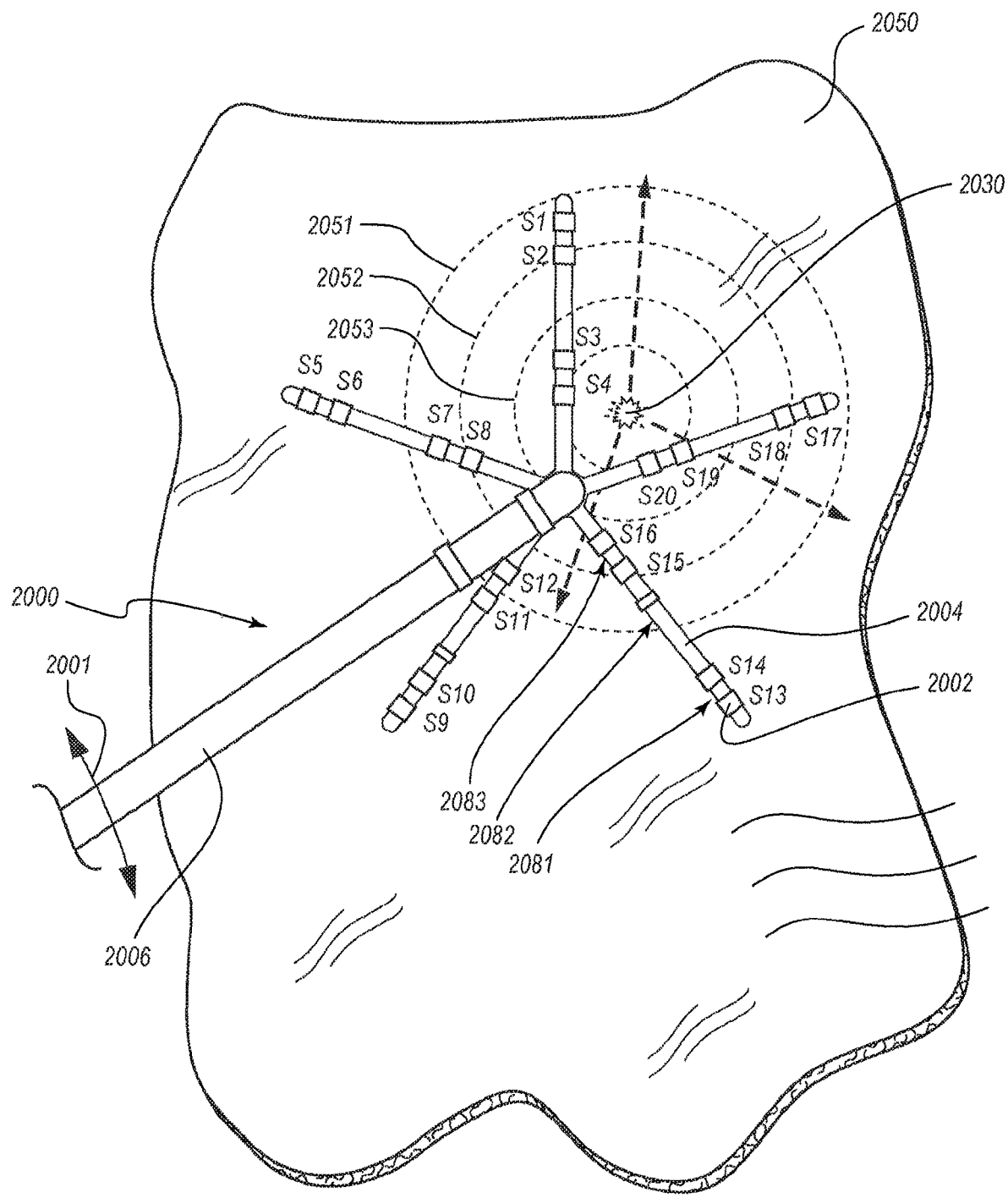
FIG. 43 is a plan view of an embodiment of a sensor assembly in the process of gathering electrograms from a portion of an atrial wall, wherein a driver is within a sensing region of the sensor assembly.

In still further instances, more localized sensing may be achieved via sensors such as those depicted in FIGS. 39, 40, and 43. For example, in various instances, a sensor may be positioned at the end of a catheter (e.g., a steering catheter), which may be positioned within an atrium adjacent to the cardiac wall. In some instances, the sensor may be held in place for a time sufficient to observe and/or obtain a suitable reading of the electrical activity of the portion of the heart against which the sensor is pressed (e.g., a fraction of a second, several seconds, a minute or less), and the sensor may then be swept or otherwise relocated to other portions of the heart.

As can be appreciated from the foregoing, any suitable sensor system, which may include one or more sensing devices, can be used to obtain electrical signals that are associated with various positions on the heart, such as the positions 180, 181, 182, 183, 184, 185 on the left atrium 102, as shown in FIG. 9. The electrical signals may correspond with or otherwise be representative of electrical signals conducted along the wall of the cardiac substrate over time (e.g., electrogram waveforms). However, in some embodiments, the electrical signals may include data from which electrogram waveforms can be determined. Stated otherwise, the electrical signals may include electrogram waveform information, and the electrogram waveforms may be determined from this information. In various embodiments, suitable sensor systems for obtaining electrogram waveform information include one or more of a sensor array balloon, a basket mapping catheter and/or any other type of mapping catheter, and an expandable mesh catheter (each of which may be positioned within the heart of the patient) and skin electrodes (which may be positioned at an exterior of the patient).

Figure 10:
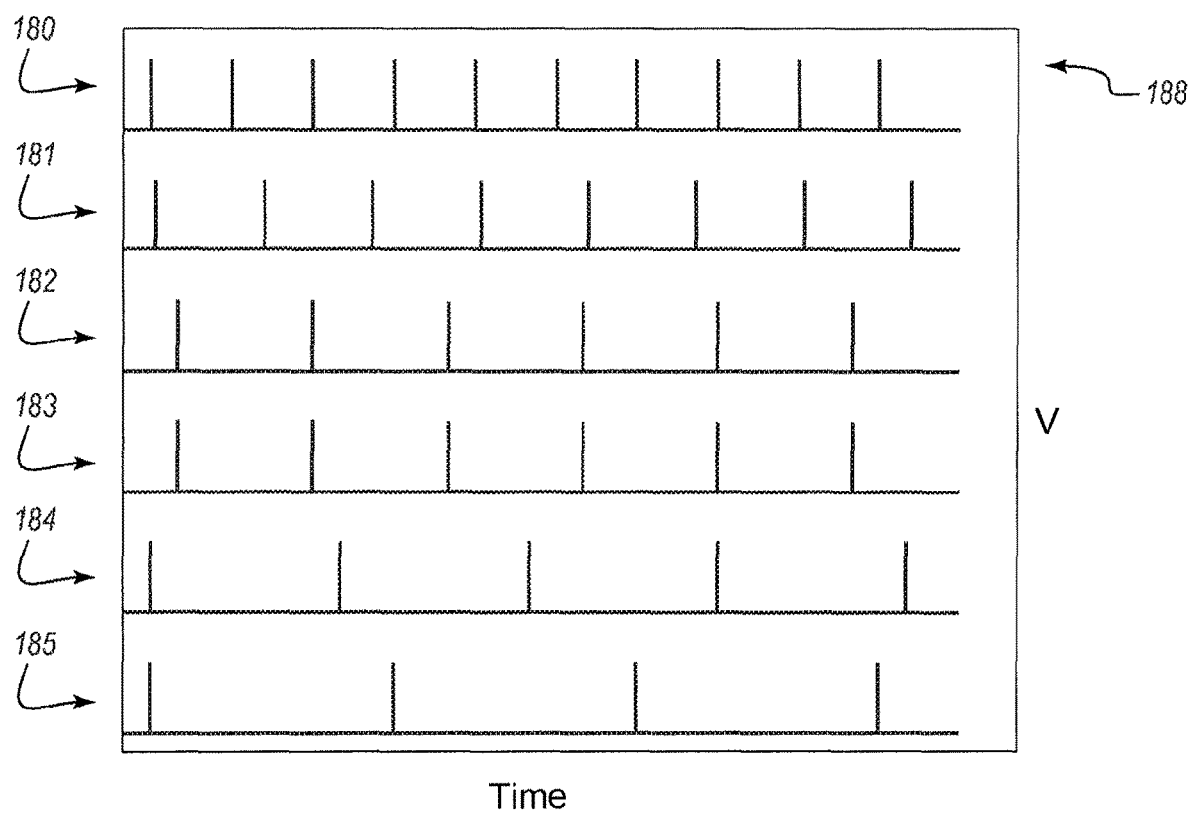
FIG. 10 is a plot illustrating the electrical signal waveforms detected at each of the regions identified in FIG. 9, wherein it can be seen that the different waveforms have different frequencies.

FIG. 10 is a plot 188 illustrating the electrical signal waveforms detected at each of the regions 180, 181, 182, 183, 184, 185 identified in FIG. 9. The different waveforms can have different frequencies. In the illustrated embodiment, all of the waveforms are generally stable, with regular periodicities. It can be visually ascertained that the waveform associated with the position 180 has the highest frequency (shortest period), and thus, of all of the regions 180, 181, 182, 183, 184, 185, the region 180 may be the closest to, or most likely to correspond with, a driver.

As previously noted, all of the waveforms in FIG. 10 are generally stable or periodic. In other instances, one or more of the waveforms may be complex and/or irregular. In some methods for determining a location of a driver, the complex and/or irregular waveforms can be eliminated or discounted as potential driver positions.

Any suitable method for analyzing and/or ranking waveforms may be used to identify one or more driver positions. For example, in some embodiments, waveforms can be ranked, as to their likelihood of corresponding to a driver position, based on their complexity (or lack thereof) and/or their frequency. Some methods rank the waveforms based on both a complexity score and/or frequency. In some embodiments, complexity may be determined via Fourier analysis (e.g., Fast Fourier Transform (FFT) analysis). A complexity score may be assigned based on the number of and/or some other property related to the constituent waves of the complex waveform. In some embodiments, high complexity and low frequency yield low rankings, whereas low complexity and high frequency yield high rankings. Rankings may be achieved via a weighting algorithm. For example, high frequencies and/or low complexities may be weighted higher than low frequencies and/or high complexities.

In other or further embodiments, one or more other factors may be incorporated into the ranking of potential driver sites. For example, in some instances, it may be assumed that multiple driver sites are present if there are multiple positions that yield high rankings, and if these positions are spaced from each other. This assumption may be even stronger if there are lower-ranked positions that are physically situated between the highly ranked positions. For example, the lower-ranked positions may have more complex waveforms than those associated with the highly ranked positions. By way of illustration, with reference again to FIG. 7, the positions 171 and 175 may be more likely to be at or near drivers (i.e., the drivers 135, 134, respectively), since these positions 171, 175 yield regular waveforms with relatively high frequencies. In some ranking or sorting algorithms, the likelihood that one or more of the positions 171, 175 may be at or near drivers may be augmented by the fact that the position 170 is situated between them and yields a complex waveform (as depicted in FIG. 8). Accordingly, in some embodiments, a ranking algorithm may assign additional weight to potential driver positions if lower-ranked areas are physically situated between the driver positions. In other or further embodiments, waveform amplitude may be used as a parameter in the ranking criteria. However, in some instances and/or for some sensing systems, amplitude may be a less useful ranking criteria as amplitude can be affected by poor electrical contact with the heart tissue. In various embodiments, one or more, two or more, or three or more of waveform unity, frequency, amplitude, and position (e.g., the position on the heart with which the waveform is associated) may be used as parameters in the ranking criteria. As discussed further below, other waveform criteria may also be used to rank signals as to their proximity to a driver and/or to determine whether signals are likely to have originated from the same or different drivers. For example, in some embodiments, a shape of the waveform, such as whether a slope thereof is initially positive or negative, the sharpness and/or number of peaks or valleys, etc., can be used to distinguish signals that originate from different drivers.

Any suitable algorithms may be used to rank the waveforms and their associated positions for likelihood of association with a driver. In some embodiments, the algorithms may be implemented by a practitioner, such as by visually observing or reviewing electrograms. The electrograms, for example, may be provided side-by-side on a display, and the practitioner might observe one or more properties of the waveforms to determine that a position on the heart associated with one or more of the waveforms is in proximity to a driver. In other or further embodiments, the algorithms may be implemented by a computer and/or dedicated hardware. In general, at least some portions of the subject matter disclosed herein may be described herein in terms of various functional components and processing steps. A skilled artisan will appreciate that such components and steps may be implemented as any number of hardware or software components or combination thereof configured to perform the specified functions. For example, an exemplary embodiment may employ various graphical user interfaces, software components, and database functionality.

For the sake of brevity, conventional techniques for computing, data entry, data storage, networking, and/or the like may not be described in detail herein. Furthermore, the connecting lines shown in various figures contained herein (e.g., FIG. 15) are intended to represent exemplary functional relationships and/or communicative, logical, and/or physical couplings between various elements. A skilled artisan will appreciate, however, that many alternative or additional functional relationships or physical connections may be present in a practical implementation of a system or method for treating AF.

Additionally, principles of the present disclosure may be reflected in a computer program product on a computer-readable storage medium having computer-readable program code means embodied in the storage medium. Any suitable tangible, nontransitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture including implementing means which implement the function specified. The computer program instructions may also be loaded onto a computer or other programmable data processing apparatus to cause a series of operational steps to be performed on the computer or other programmable apparatus to produce a computer-implemented process, such that the instructions which execute on the computer or other programmable apparatus provide steps for implementing the functions specified.

Figure 11:
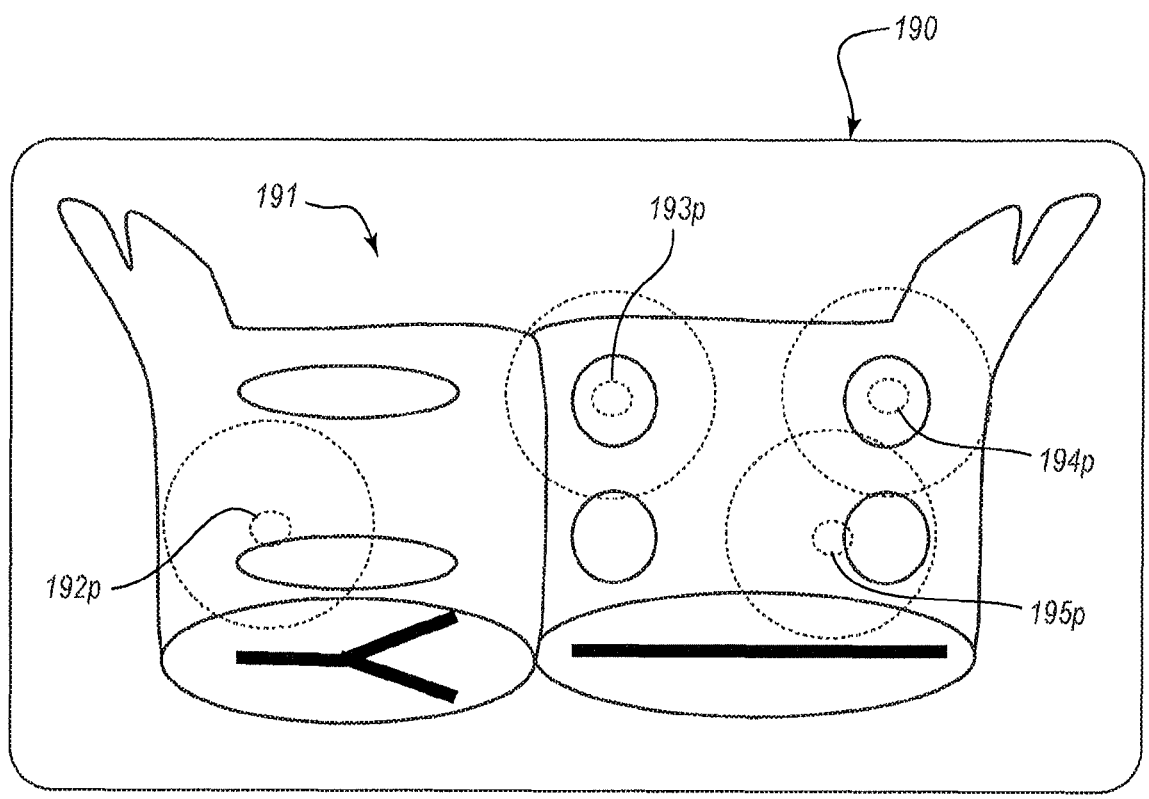
FIG. 11 is a schematic representation illustrating the location mapping of atrial drivers found by ranking electrical signals based on their uniformity and frequency.

FIG. 11 is a schematic representation illustrating the location mapping of atrial drivers found by ranking electrical signals based on their uniformity and frequency. In some embodiments, FIG. 11 may correspond with a display 190 on which a representative image 191 of the heart is displayed to a practitioner. The representative image 191 may simulate a 3-dimensional model of the heart, or a portion thereof. For example, 3-dimensional mapping may be performed. In some embodiments, the potential driver positions 192$p$, 193$p$, 194$p$, 195$p$ may be shown on the display 190. In some embodiments, the rank or weight of each driver position 192$p$, 193$p$, 194$p$, 195$p$ may also be shown, such as by color, grayscale, or any other suitable visual indicator. In some embodiments, the representative image 191 may be multicolored, with the color scale corresponding to driver ranking or likelihood of driver position. For example, the image 191 may comprise an isochronal map of at least a portion of the heart. As colored, the representative image 191 may provide a 4-dimensional map of the heart, with the three physical dimensions being overlaid with one or more colors representative of the fourth dimension (such as driver ranking, likelihood of driver position, signal frequency, etc.). In some embodiments, the coloring may be determined by one or more of waveform stability and frequency for a given position on the heart. Accordingly, a practitioner may be able to readily identify the positions that are likely associated with drivers, such as by looking for one or more "hot spots" on the image 191 and/or one or more positions that are flagged as being potential driver positions. In further embodiments, the waveforms generated at multiple positions may also be shown on the display 190 (e.g., in a manner similar to that illustrated in FIG. 24). In some embodiments, a practitioner may edit the image 191, such as by adding a desired color, symbol, and/or other indicator at one or more positions on the image 191 to indicate any desired property, such as likelihood of being (or being near) a driver. In other or further embodiments, a computer program or other machine-implemented algorithm may automatically assign one or more colors, symbols, and/or other indicators to the image 191.

In some embodiments, atrial electrograms (such as shown in FIGS. 10 and 24) can be collected in real time and an isochronal mapping of the heart based on the electrograms (such as shown in FIG. 11) can be provided. For example, the image 191 may be provided on a screen that is observable to a practitioner. As further discussed below, in some embodiments, the mapping is achieved via non-contact sensors within the heart. In other embodiments, the mapping may be achieve via contact sensors, certain of which may be moved relative to the surface of the heart. Any other suitable method for mapping the heart and/or obtaining the image 191 is contemplated. In some arrangements, rapid collection of high density electrograms from the left and right atria is possible. Sorting or ranking algorithms can be used on the electrograms, such as discussed above. Signals can be assessed based on stability—for example, non-stable electrograms may be omitted or discounted, whereas stable electrograms (e.g., those with regular atrial-beat-to-atrial-beat ["A-A"] intervals) may be compared. Local A-A intervals may be assessed and compared. One or more targets may be identified for ablation based on the most rapid (highest frequency) stable signal or signals.

As can be appreciated from FIG. 11, in some embodiments, multiple AF drivers can be identified simultaneously. For example, the algorithms used to analyze and rank, sort, characterize, weight, or otherwise assign value to waveforms can do so in a way that accounts for the possibility that multiple drivers may be present. In FIG. 11, four potential driver positions 192p, 193p, 194p, 195p have been identified.

FIG. 12 is a schematic representation illustrating an atrial driver isolation procedure to electrically isolate three of the actual atrial drivers 193a, 194a, 195a, which are representatively shown in FIG. 11, so as to prevent undesired signals from these drivers from propagating along the atrial wall. Ablation paths 120, 122 may be similar to those shown in FIG. 2. For example, standard PVI procedures may be employed. The actual driver 192a, however, can be addressed in a manner different from what is shown with respect to the driver 131 in FIG. 4. For example, in many instances of prior art techniques, the additional paths 140, 142 and/or 144 of FIG. 4 may be formed in other procedures because an exact location of the drivers 131, 132, 133, 134, 135, 136, 137 and/or 138 could not be determined. However, by determining the exact or approximate position of the actual driver 192a, focal ablation at, on, or near the driver 192a is possible, as shown in FIG. 13.

FIG. 13 is a schematic representation illustrating an atrial driver isolation procedure to electrically isolate two of the atrial drivers 194a, 195a shown in FIG. 11 in a manner slightly different than that shown in FIG. 12, and further showing a focal ablation procedure to locally isolate the atrial driver 192a (of FIG. 12). In FIG. 13, the atrial path 120 is the same as shown in FIG. 12. However, a different ablation path 123 may be formed to isolate the drivers 194a, 195a. The path 123 may be smaller (or larger) than the path 122 and more focused, or informed, to ensure that the drivers 194a, 195a are isolated within the PVI ablation path. This can reduce the amount of scarring of the heart wall. The focal ablation 125 can also result in much less damage to the heart than would be possible if the location of the driver 192a were unknown. As can be appreciated from FIG. 13, electrical isolation of the driver 192a via ablation can in some instances involve direct ablation of the driver itself, rather than encircling the driver with scar tissue.

Figure 14A:
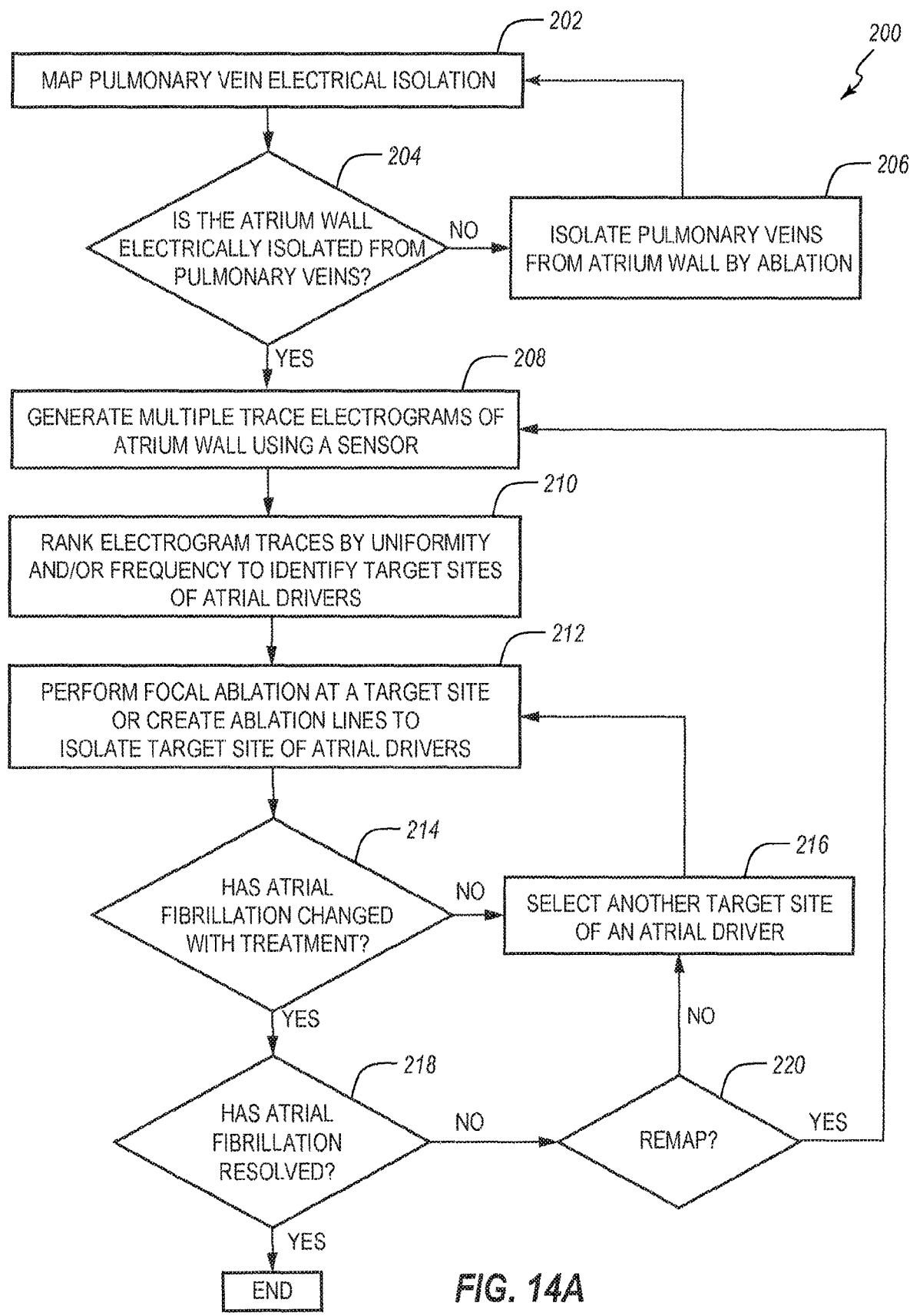
FIG. 14A is a flowchart depicting an illustrative method of treating atrial fibrillation.
Figure 14B:
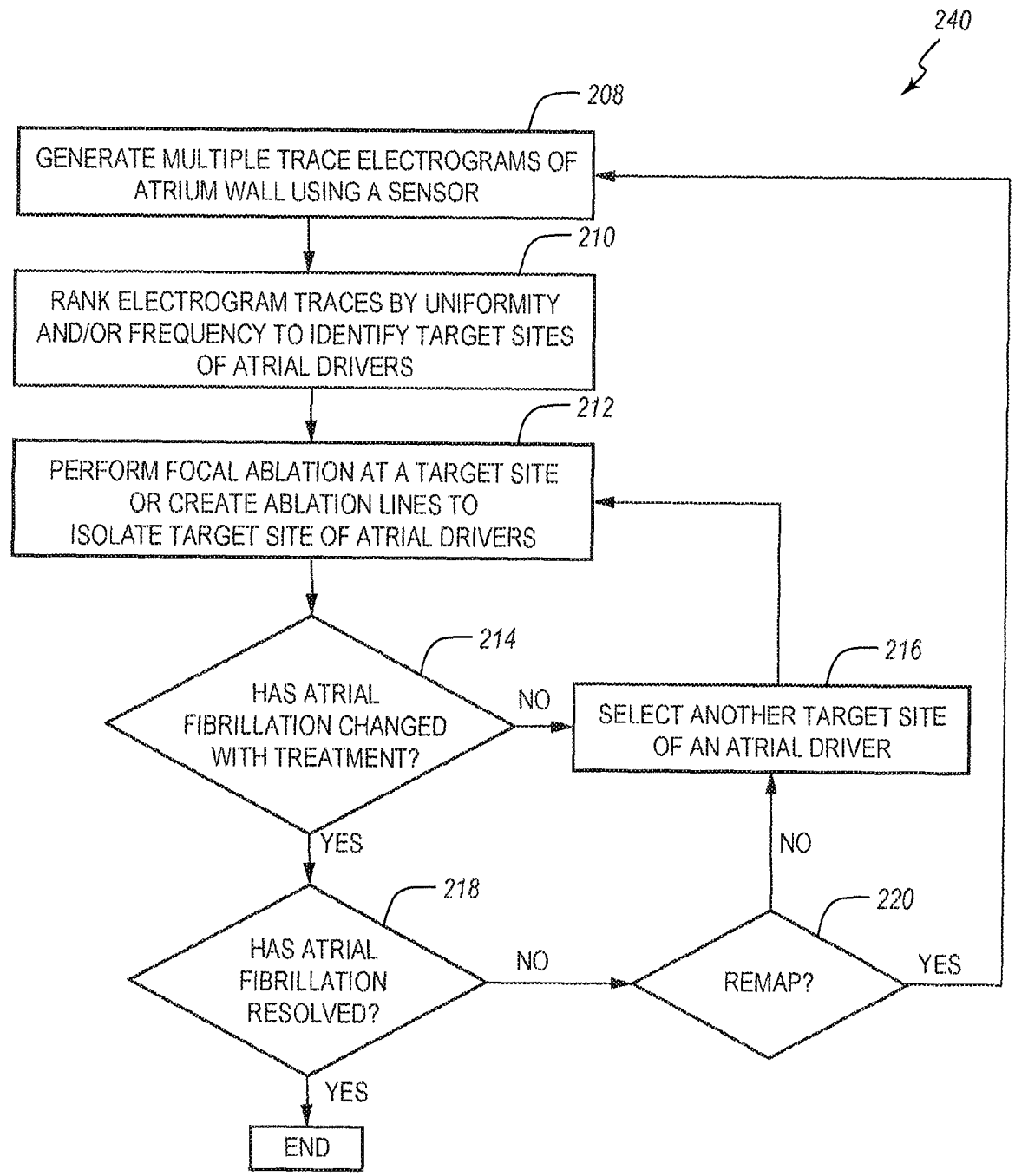
FIG. 14B is a flowchart depicting another illustrative method of treating atrial fibrillation.
Figure 14C:
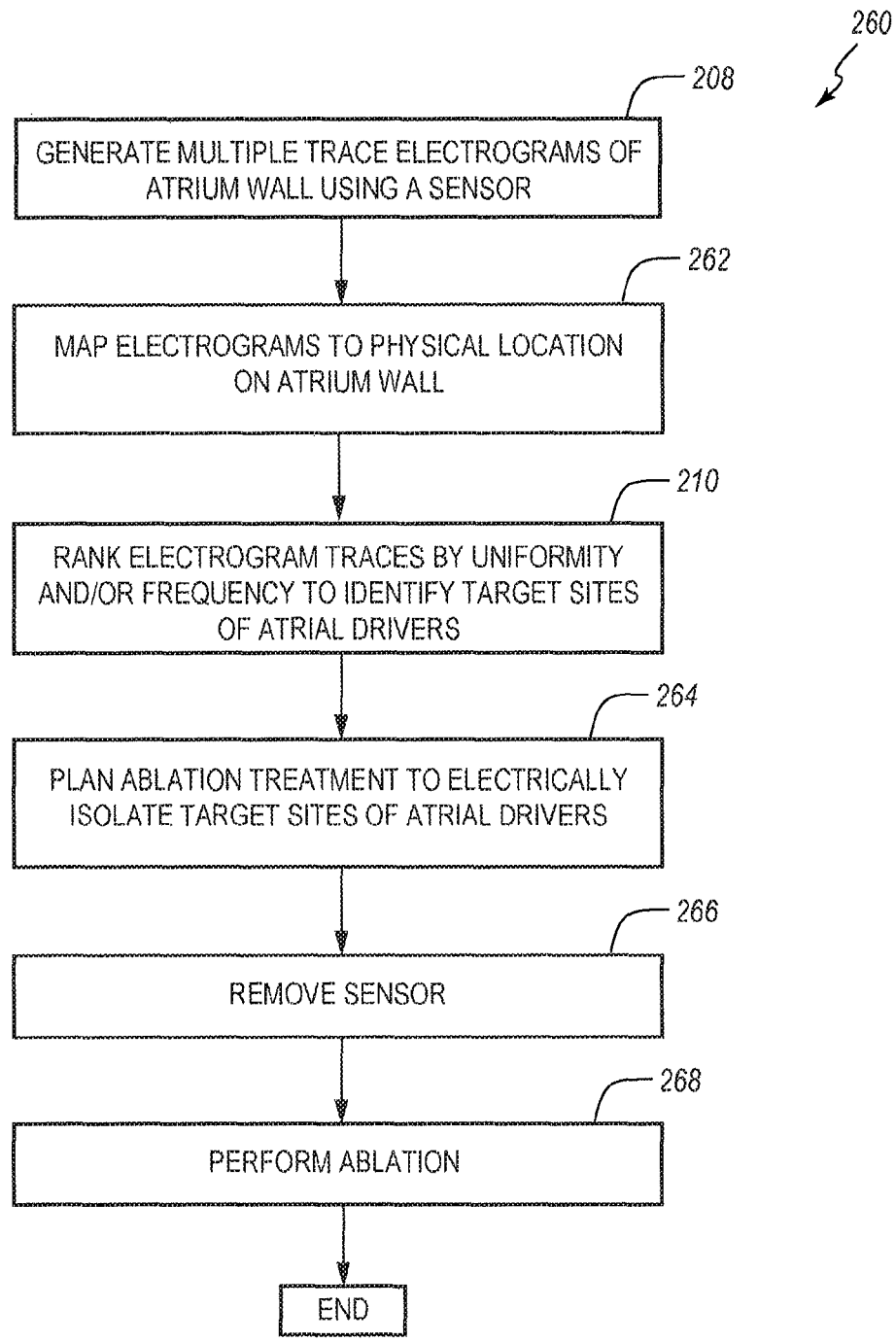
FIG. 14C is a flowchart depicting yet another illustrative method of treating atrial fibrillation.

FIGS. 14A-14C are flowcharts depicting illustrative methods 200, 240, 260 of treating atrial fibrillation. Some of the stages shown in each chart may be performed by a practitioner; others may be performed via devices and/or systems described herein. For example, in some instances, at least some of the steps may be performed via a computing device. In still further embodiments, at least some of the steps may be automated. Accordingly, any suitable subset of the stages shown in any of FIGS. 14A-14C can stand alone as a separate or independent method. Moreover, any suitable order of the depicted stages is contemplated.

With reference to FIG. 14A, the method 200 includes a stage 202 at which at least a portion of the heart is mapped to determine the electrical isolation of one or more pulmonary veins. At decision block 204, it is determined from the mapping whether the one or more pulmonary veins are electrically isolated from the atrium wall. If not, then the method proceeds to stage 206 at which the pulmonary veins are isolated from the atrium wall via ablation. If they are isolated, then the method proceeds to stage 208. At stage 208, multiple trace electrograms of the atrium wall are generated using a sensor, or stated otherwise, via any suitable sensor system. Examples of suitable sensor systems are discussed above with respect to FIG. 9, and further examples are discussed below with respect to FIGS. 15-26, 39, 40, and 43. In many embodiments, the sensor system is positioned within the heart of the patient to obtain the data used in the electrograms, although other or further sensor systems may employ detection devices that are situated at an exterior of the patient. At stage 210, the electrogram traces are ranked according to their uniformity (regularity, lack of complexity, etc.) and/or their frequency. As a result of stage 210, the position(s) on the heart that are associated with the highest ranking electragram trace(s) can be identified. These identified positions are the target sites at which drivers are likely to be (or be near). In other or further methods, the ranking can be based on other or further criteria, such as previously discussed. The identification may include tagging, marking, coloring, or otherwise altering an image of the heart, such as the image 191 discussed above.

At stage 212, focal ablation is performed at a target site, or ablation lines are created to isolate the target site associated with an atrial driver. At decision block 214, it is determined whether atrial fibrillation has changed with the treatment thus far. If not (or if it has changed, but there are still atrial fibrillation issues), then the procedure loops back to stage 212. If so, then the procedure proceeds to decision block 218, at which it is determined whether atrial fibrillation has been fully resolved. If not, then the procedure proceeds to decision block 220 at which it is determined whether a remapping event should take place. If not, then the procedure loops back to stage 216. If so, then the procedure loops back to stage 208. If the atrial fibrillation has been fully resolved, then the procedure is at an end.

FIG. 14B is a flowchart depicting another illustrative method 240 of treating atrial fibrillation. The method 240 closely resembles the method 200. However, the stages 202, 206, and the decision block 204 are omitted. Accordingly, the method 240 proceeds without isolating the pulmonary veins and/or verifying that the pulmonary veins are electrically isolated. In some instances, the method 240 can successfully resolve AF without isolating the pulmonary veins. The method 240 can identify and electrically isolate only the drivers that are the source of the AF. Otherwise, the stages and decision blocks 208, 210, 212, 214, 216, 218 of the method 240 can proceed in the same manner as discussed above with respect to the method 200.

FIG. 14C is a flowchart depicting another illustrative method 260 of treating atrial fibrillation. At stage 208, multiple trace electrograms of the atrium wall are generated using a sensor (or sensor system—e.g., any suitable sensor system, such as those discussed above and below). At stage 262, each electrogram is mapped to a physical location on the atrium wall, such as by generating or modeling a 3-D representation of the atrium wall. Each electrogram may be associated with specific locations on a model or image of the atrium wall thus generated. At stage 210, the electrogram traces are ranked according to their uniformity (regularity/lack of complexity/etc.) and/or their frequency. As a result of stage 210, the position(s) on the heart that are associated with the highest ranking electragram trace(s) can be identified. These identified positions are the target sites at which drivers are likely to be (or be near). In other or further methods, the ranking can be based on other or further criteria, such as previously discussed. In some embodiments, a representation of some property of the electrogram is assigned to the 3-D model. For example, each electrogram may be represented by a color, grayscale shade, or other suitable visual indicator corresponding with a property of the electrogram, such as its frequency, stability, and/or uniformity, or its ranking or weighting as a potential driver location (which may be calculated or evaluated in any suitable manner, such as discussed above). Stage 210 can include overlaying the 3-D map with a representation of a fourth dimension. At stage 264, an ablation treatment is planned to electrically isolate the target sites. The ablation treatment may include directly ablating and/or encircling with ablated tissue one or more of the atrial drivers.

In some instances, stage 264 may be omitted, or it may be automatic. For example, in some embodiments, the ranking at stage 210 may include assigning various threshold values to potential ablation sites. For example, a likelihood that a position on the atrium wall is at or near a driver may be assigned a color. At stage 210, two or more, three or more, or four or more colors may be used to rank various positions on the atrium wall within a like number of probability ranges. For example, three colors may be used to identify highly likely, moderately likely, or unlikely driver positions (e.g., yellow, blue, red, respectively). In certain of such procedures, the stage 264 may be omitted, or it may be automatic. For example, the ablation treatment plan at stage 264 may merely be to perform focal ablation at each position that is marked in the "highly likely" color (e.g., yellow).

At stage 266, the sensor is removed from the patient. At stage 268, the ablation is performed.

FIGS. 15-22 illustrate a non-limiting embodiment of a system 305, and non-limiting embodiments of components thereof, that can be used in, with, or as one or more of the methods and systems previously discussed. The system 305 can include a non-contacting sensor array that is configured to be positioned within the heart and to obtain measurements at positions that are spaced from the wall the heart.

Figure 15:
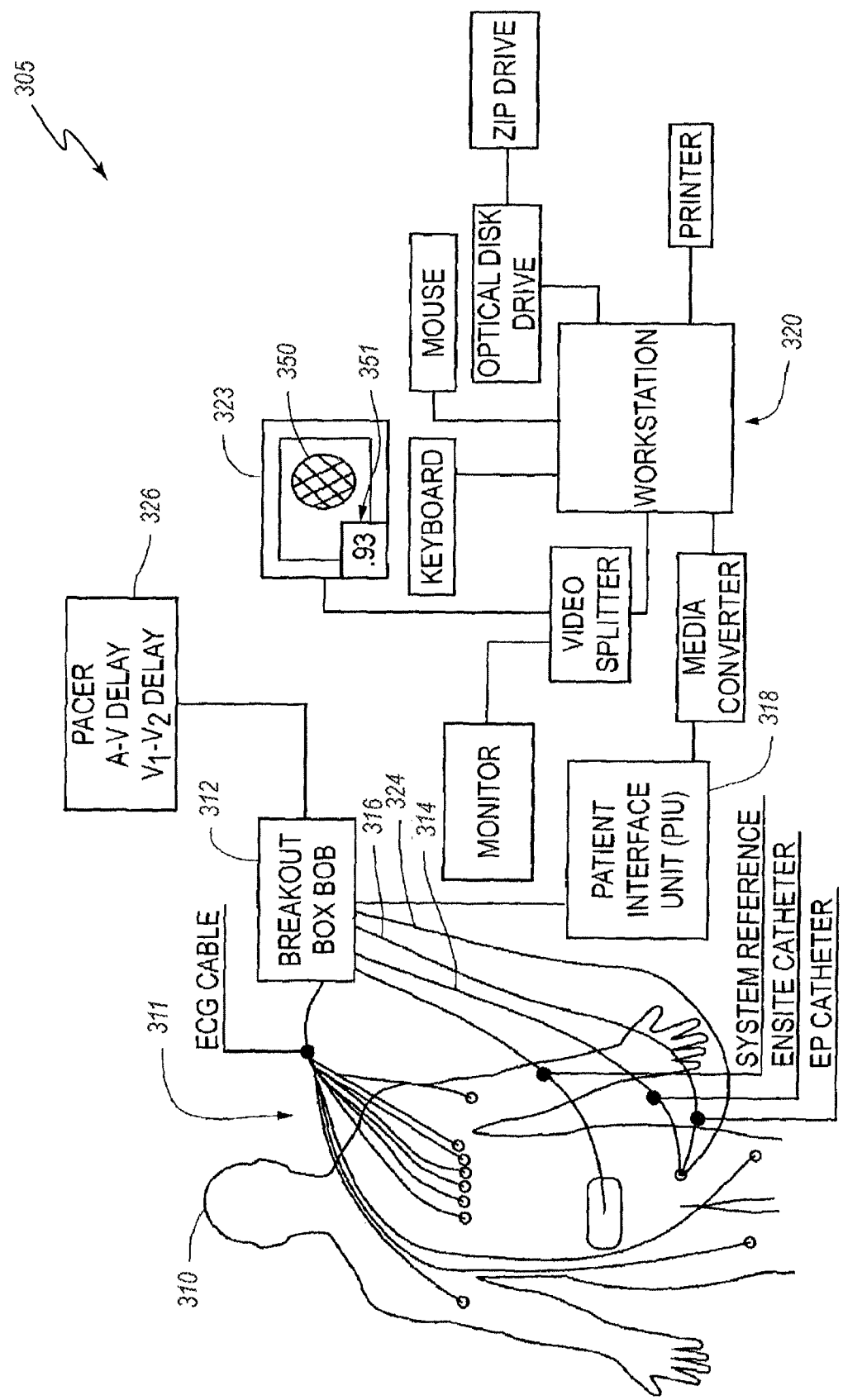
FIG. 15 is a schematic diagram of an embodiment of a system that can be used to identify one or more atrial drivers.

FIG. 15 is a schematic diagram of the system 305, which can be used identifying one or more atrial drivers. The system 305 may be referred to as an electrophysiology mapping system. In some embodiments, the system 305 may comprise the EnSite® system available from St. Jude Medical of St. Paul, Minn. In some embodiments, the EnSite® system presents electrophysiologic data on a static geometry of the heart, and it should be recognized that certain heart information (e.g., EP activation) is available on a single beat basis. Further examples of systems that may be used are provided in U.S. Pat. Nos. 6,978,168; 7,187,973; and 7,189,208, the entire contents of which are hereby incorporated by reference herein. Certain of these patents provide details for receiving cardiac signals (e.g., electrogram) that represent electrical signal transmission along the cardiac wall. Stated otherwise, details are provided for mapping multiple points of electrogram data to physical regions on the cardiac substrate, which can be accomplished via sensors such as described below.

In the illustrated system 305, a patient 310 is undergoing a minimally invasive ablation procedure. The initial stages of the procedure involve mapping the heart and obtaining trace electrograms, as described hereafter. A specialized catheter 314, which in some arrangements may be a branded EnSite Array™ catheter, is coupled to a breakout box 312. A conventional electrophysiology catheter 316 may also be introduced into the patient while a variety of surface electrodes 311 are used to monitor cardiac activity during the procedure. The breakout box 312 permits the ECG cables and EP system to be coupled to additional hardware, which is not shown in this figure. The patient interface unit 318 couples the catheter 314 to a workstation computer 320 and its related peripherals. The workstation operates under the control of a software program, which provides a substantial amount of information to the attending physician.

Figure 19:
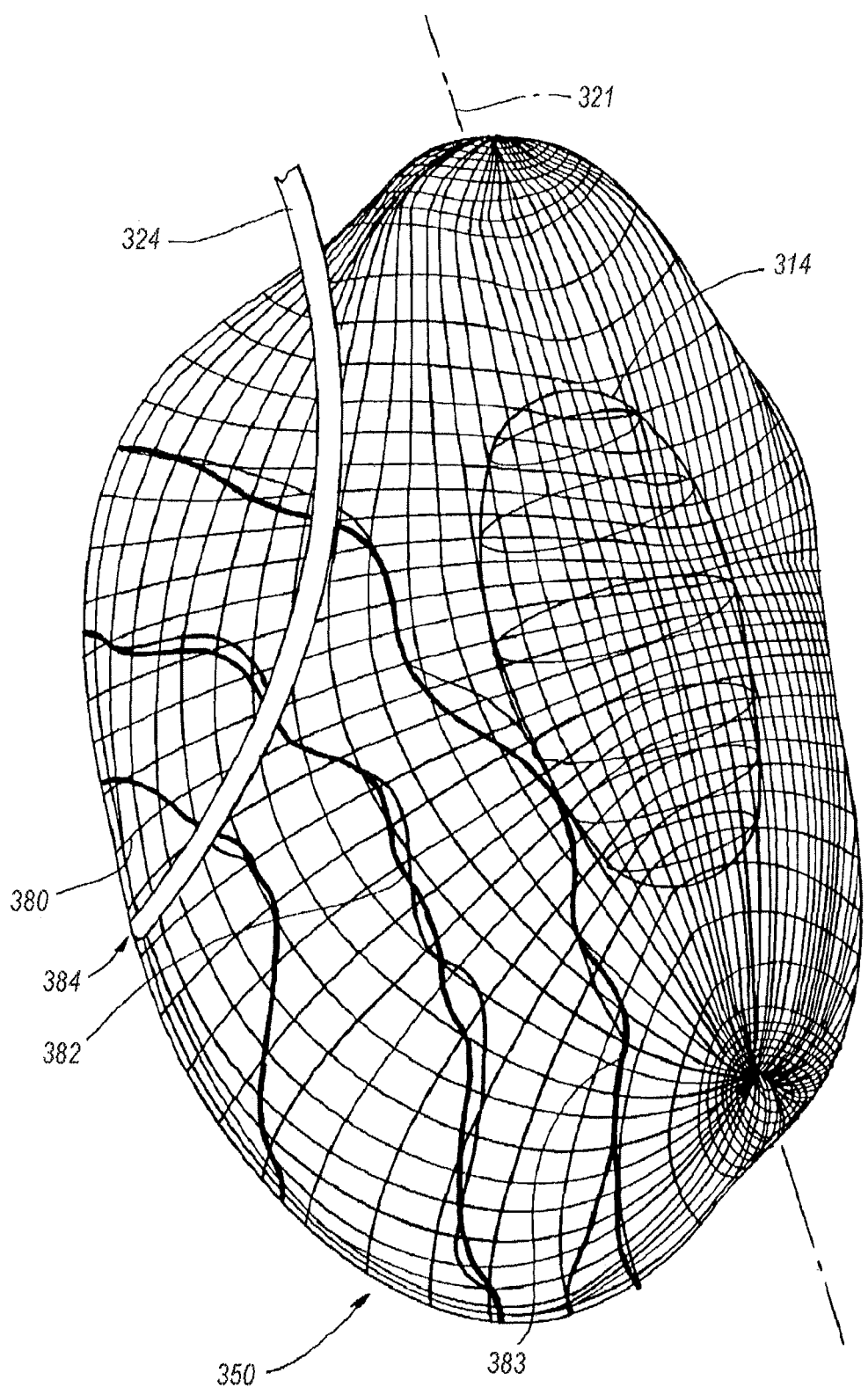
FIG. 19 is a diagram of an illustrative output display from the system of FIG. 15.

In use, the physician will see a map image similar to that shown in FIG. 19 on a monitor 323. A computed index 351 may also been shown to the physician as indicated by index value "0.93" seen on the monitor 323, although in other instances the computed index 351 may not be shown. In other or further instances, trace electrograms may be shown on the monitor 323 (such as depicted in FIG. 24). In general, the physician is able to visualize the intracardiac cavity 332 containing the catheter 314, as seen in FIG. 19, on the monitor 323, which may be in color. Color can be used to reduce the clutter in the image. Expressed or displayed on this wire frame geometry image 350 are maps and other electrophysiology information derived from the catheter 314. In some procedures, a patient is also provided with one or more pacing catheters 324 which are coupled to a temporary pacer 326 through the breakout box 312. The temporary pacer 326 allows the physician to make measurements while varying the A-V delay and the V-V delay time. Pacing rate may be varied to ensure capture.

Turning to FIG. 16, the heart 330 is shown schematically with a right ventricle 332 containing the catheter 314 and a conventional EP catheter 316 as well as the pacemaker lead 324. In brief, software running on the workstation 320 in FIG. 15 can create an electrophysiological map of the heart during a single heartbeat as follows. In operation current sourced from a pair of electrodes (electrode 340 and 342) and injected into the heart chamber 332. A roving catheter, shown as EP catheter 316, is located on the endocardial surface 331 toward the exterior of the heart this catheter may be moved widely and may be placed on the interior heart surface along the septum is shown by reference numeral 333. The injected current is detected through the electrode 344 on the EP catheter 316. This location is determined and as the catheter is moved about the chamber, complete chamber geometry can be built up by noting the sequential positions of the electrode 344. Incorporated references describe this process in more detail, but for purposes of this disclosure, a convex hull modeling technique is used to build a statically displayed interior geometry of the heart chamber by selecting certain locations developed from the electrode motion. The convex hull model of the interior chamber of the heart can be smoothed and a representative wire grid displayed to the physician. Such a wire grid is shown in FIG. 19 as element 350.

The catheter 314 also carries an array of passive electrode sites, which may also be referred to a sensors, typified by electrode site 346. These electrodes are arrayed around the geometric access of the balloon 347. At any given instant some of these electrode sites are pointed toward the exterior surface wall 331 and the septal wall 333. By computing the inverse solution, the electrophysiologic potentials passing along these surfaces can be measured within one beat. Reference may be had to U.S. Pat. Nos. 5,297,549; 5,311,866; 6,240,307 and 5,553,611 for further discussion of the inverse solution and the creation of the electrophysiologic map. Each of these references is incorporated in its entirety in the present application.

In some systems, the depolarization wavefront is displayed on a representative geometric surface such as the grid surface 350 of FIG. 19. The workstation 320 animates this electrophysiology data and the propagation of the electrical wavefront along the interior surfaces of the heart can be monitored. Wavefronts 380, 382, and 383 are sequence movements of the stimulus from pacing site 384 seen in FIG. 19.

Figure 20:
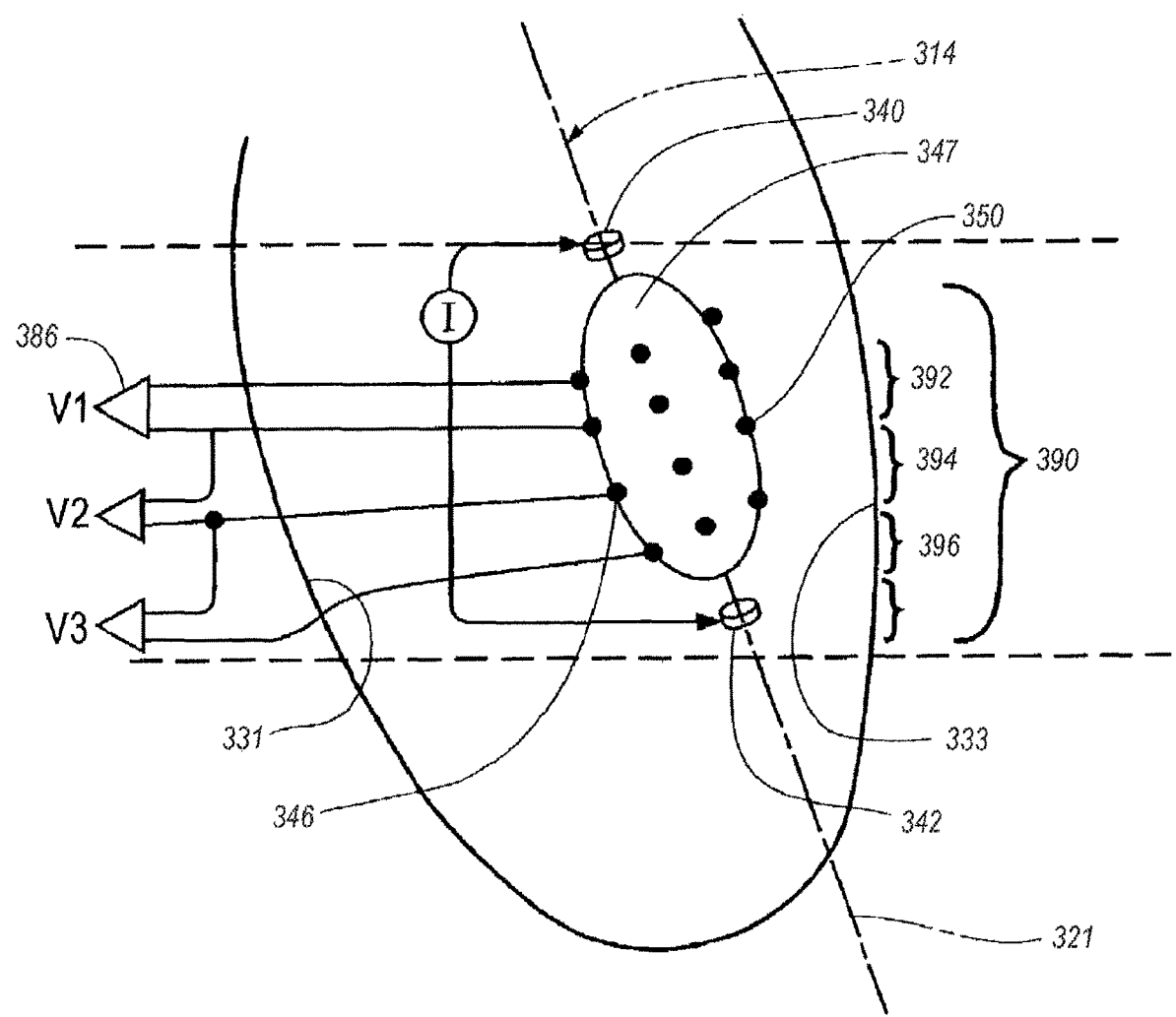
FIG. 20 is an equivalent circuit of a measurement made by the system of FIG. 15.

FIG. 20 shows an equivalent circuit implementation to facilitate a description of conduction volumetry measurements made from a catheter 314. Returning to the geometry of the array on the catheter 314 the interior of the balloon 347 is non-conductive which provides a limited field of view for each of the electrode sites on the surface of the balloon. In essence each electrode responds only to electrical activity bounded by the heart wall, which is directly opposite the electrode site. For example, an electrode such as electrode 346 sees electrical activity and conductance data bounded by the wall 331 and is blind to electrical activity on wall 333. In a similar fashion, an electrode such as electrode 350 sees only electrical activity occurring on wall surface 333. By monitoring the voltages on the array electrodes during the pulse, or more particularly measuring the resistance between adjacent columnar pairs of electrodes as indicated by exemplary difference amplifier 386 it is possible to compute the volume of a partial slice 388 of the chamber volume best seen in FIG. 21. It is important to note that the volume measurement is segmented into several local volumes typified by volume 388.

Figure 21:
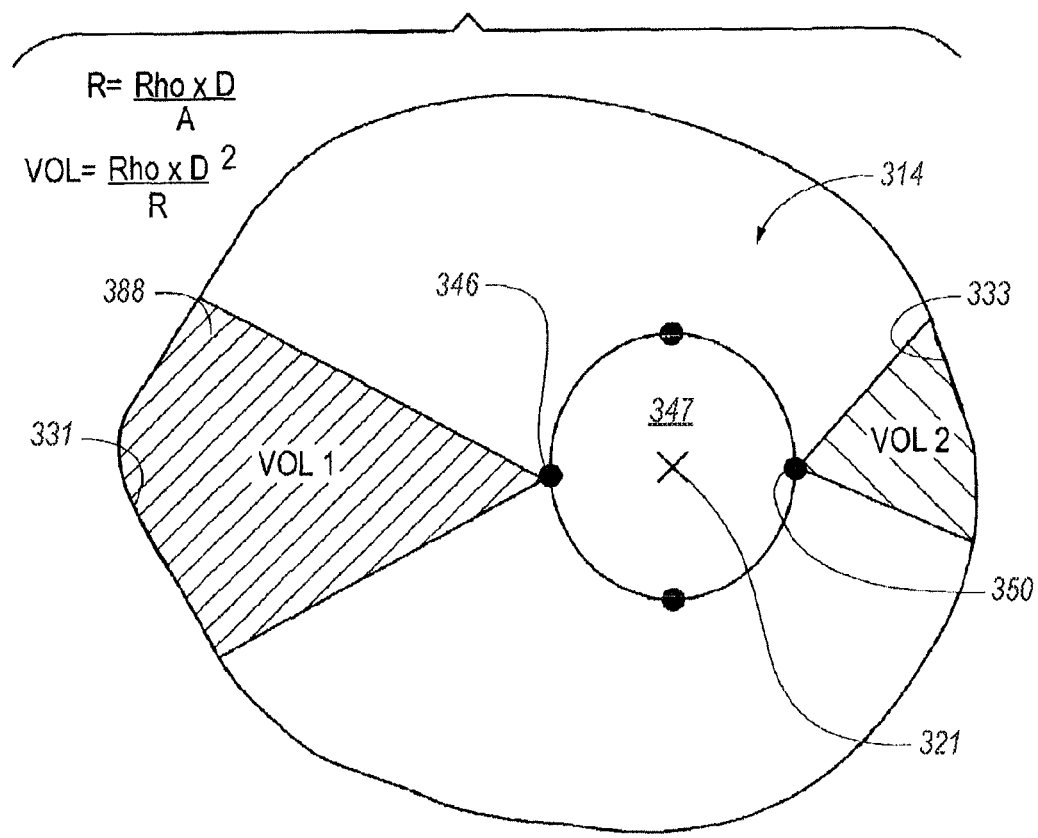
FIG. 21 is a diagram of a measurement made by the system of FIG. 15.

FIG. 21 shows a slice of chamber volume computed by measuring the difference in resistance between electrodes adjacent along the axis 321. This view shows that the volume segments are non-overlapping and extend along the axis 321. The conductance term R is the resistance measured at electrodes in the passive array. This value is directly available to the software in the program, and Rho is the conductance of the blood in ohms-centimeters. D represents the distance between adjacent electrode sites in the passive array along the axis 321. This value is known from the geometry of the catheter 314. The preferred conduction volumetry algorithms can be computed very fast and the volume changes throughout a single beat of the heart may be tracked. The measurement of chamber volume is most accurate at the mid volume level indicated in FIG. 20 at reference 390. It is preferred but not required to sum or stack the independent volume measurements to create "columnar values" centered on the axis 321. This is achieved by adding volumes 392 through 396 to create a column volume 390 located near the septum. A similar process is repeated to create a column volume near the wall 331 as shown as a slice 388 in FIG. 21 as well as elsewhere around the chamber.

Without being bound by theory, it is believed that the most effective heartbeat will involve the simultaneous and progressive activation of all of the muscle tissue, which should result in a self similar reduction in the measured volume among all of the volume segments measured.

Figure 22:
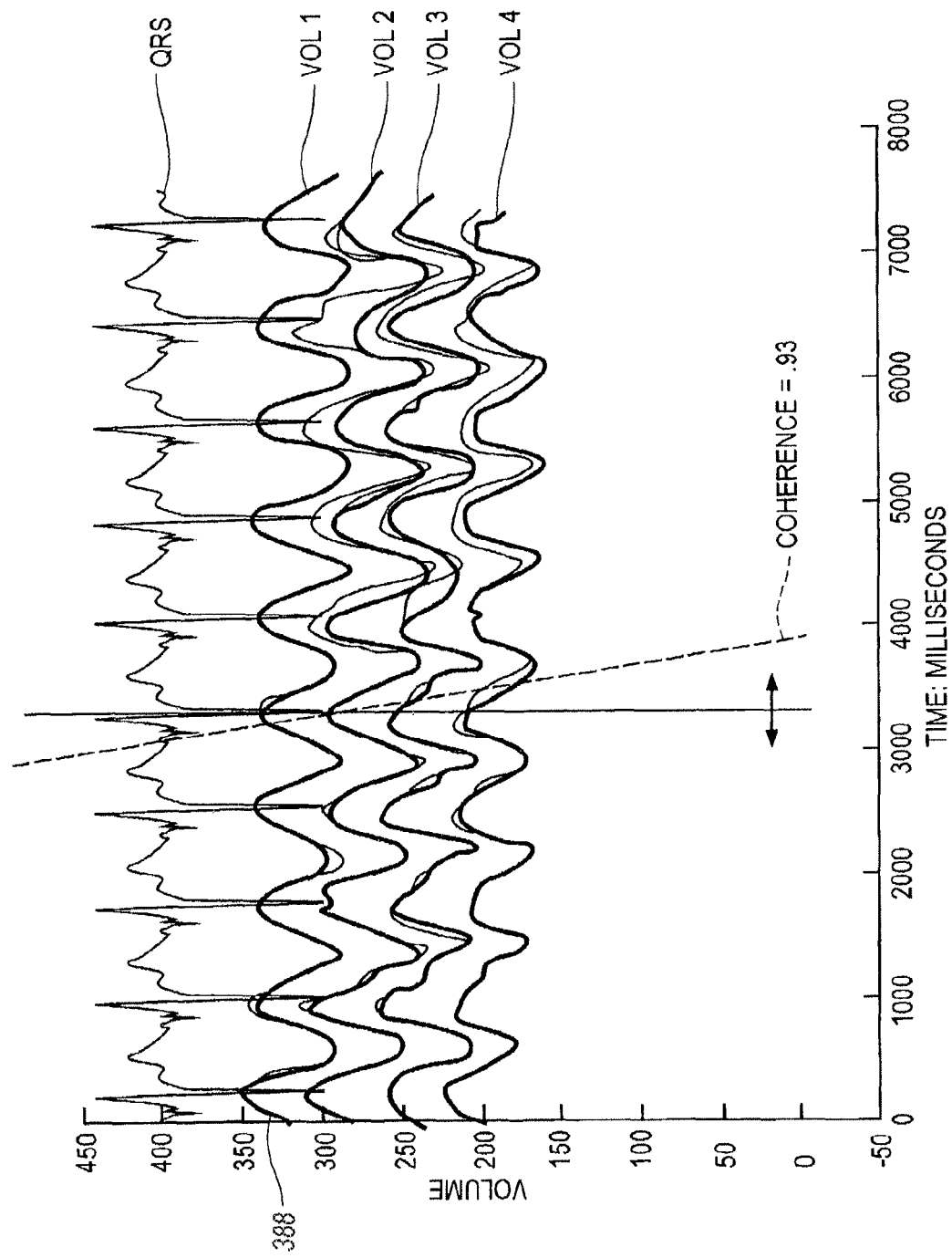
FIG. 22 is a display representing the "coherence" measure and the index of hemodynamic performance as determined by the system of FIG. 15.

FIG. 22 is a display of four representative volume segments of the heart chamber displayed as a function of time. Eight volumes may used effectively in some arrangements. Segment 388 may correspond to the antero-lateral volume while the other traces represent other volumes such as the septal; antero-septal; anterior; antero-lateral; lateral or other volumes defined around axis 321. A suitable way to compare the self-similarity of the volume waveforms is to cross correlate them statistically. By cross correlation of the values of the segment volumes over time one can compute a number that represents the similarity relationship of the various waveforms to each other.

The system 305 may be used for generating trace electrograms. For example, in some embodiments the system 305 is not used in placement of a pacing lead, but rather is used primarily to generate data that is used in identifying atrial drivers. For example, in some embodiments, the contraction efficiency is not calculated or otherwise determined over the course of a procedure.

Figure 23:
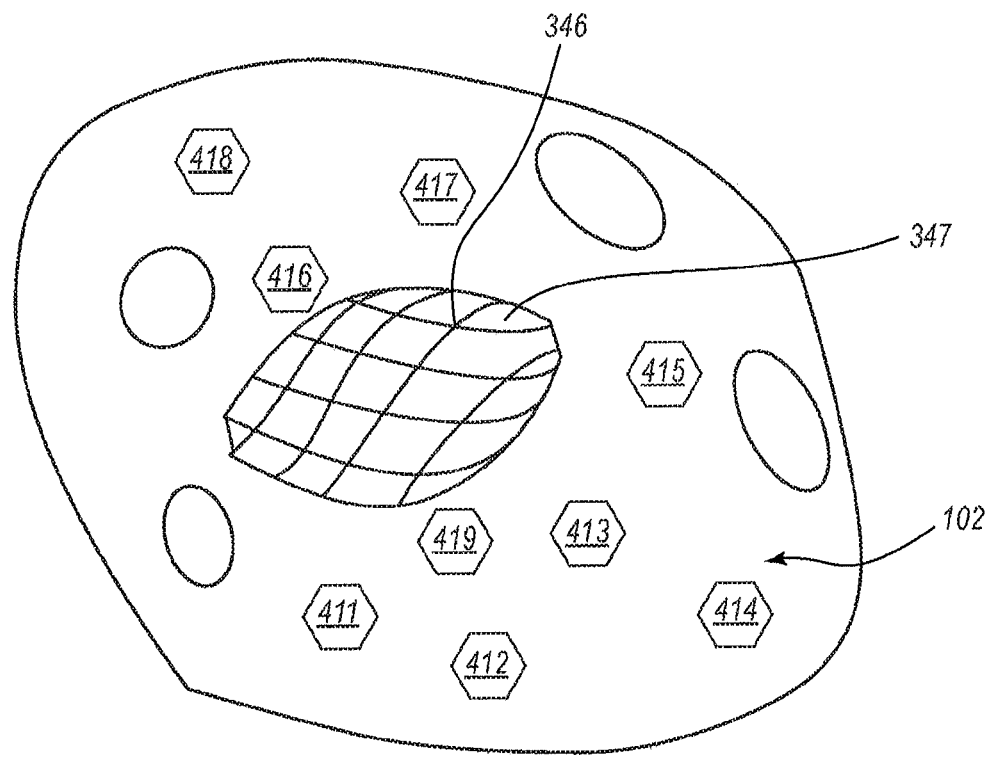
FIG. 23 is a schematic representation of a non-contact sensor collecting cardiac signals from multiple regions or volumes and interpolating the signals to locations on the cardiac substrate or atrial wall.

As shown in FIGS. 16-19, the catheter 314 may be used in mapping the right and left atria. As shown in FIG. 23, the catheter 14 is inserted into the left atrium 102, and the balloon 347 and sensors 346 are deployed. The sensors 346 are capable of obtaining information from which trace electrograms can be generated. For example, the trace electrograms shown in FIG. 24 can correspond with the positions 411, 412, 413, 414, 415, 416, 417, 418, 419 on the atrial wall shown in FIG. 23. These trace electrograms can be used in manners such as described above.

FIG. 25A is a schematic cross-sectional view of a portion of another embodiment of a system for identifying one or more atrial drivers, wherein the system includes a multi-sensor array 450 that is shown in a constricted or non-deployed state within the left atrium 102.

FIG. 25B is another schematic cross-sectional view of the portion of the system shown in FIG. 25A, wherein the multi-sensor array 450 is in an expanded or deployed state such that sensors 452 thereof are in contact with the atrial wall. Each sensor 452 may be configured to detect electrical properties of the atrial wall, from which a trace electrogram can be generated. Accordingly, a trace electrogram can be generated for each portion of the wall that a sensor 452 contacts. Further algorithms may be possible for generating trace electrograms associated with positions of the atrial wall that are between the sensors 452. Any of the foregoing electrograms thus generated can be employed in any of the methods described above.

FIG. 26 is a schematic cross-sectional view of a portion of another embodiment of a system 470 for identifying one or more atrial drivers. The system 470 includes a sensor system 472, which includes a plurality of sensor devices 474 that are positioned at an exterior of the patient 310. In particular, in the illustrated embodiment, the sensor devices 474 are skin electrodes. Any suitable number and/or arrangement of skin electrodes may be used, and these may be situated in an array. The sensor system 472 can further include, or be coupled with, a processor 476, which can store and/or process data received from the sensor devices 474. Information received from the sensor devices 474 can be used in any suitable manner to generate trace electrograms associated with positions of the atrial wall of the heart 330. For example, suitable methods for obtaining trace electrograms associated with the heart, based on information from the surface of the body (e.g., from body surface mapping), are disclosed in U.S. Pat. Nos. 7,016,719 and 7,983,743, the entire contents of which are hereby incorporated by reference herein. Schematic diagrams and flow charts associated with some suitable methods, which are discussed in U.S. Pat. No. 7,983,743, are provided in FIGS. 27A-27D. In some embodiments, a geometry determining device, such as a CT scanner, is used to determine the geometry of the heart 330 and/or the patient's torso. This information can be combined with the electrical signal information obtained via the sensor system 472 to map the atrial wall of the heart 330, as well as obtain trace electrograms. The electrograms thus obtained can be employed in any of the methods described above.

It will be understood by those having skill in the art that changes may be made to the details of the above-described embodiments without departing from the underlying principles presented herein. For example, any suitable combination of various embodiments, or the features thereof, is contemplated.

Figure 28:
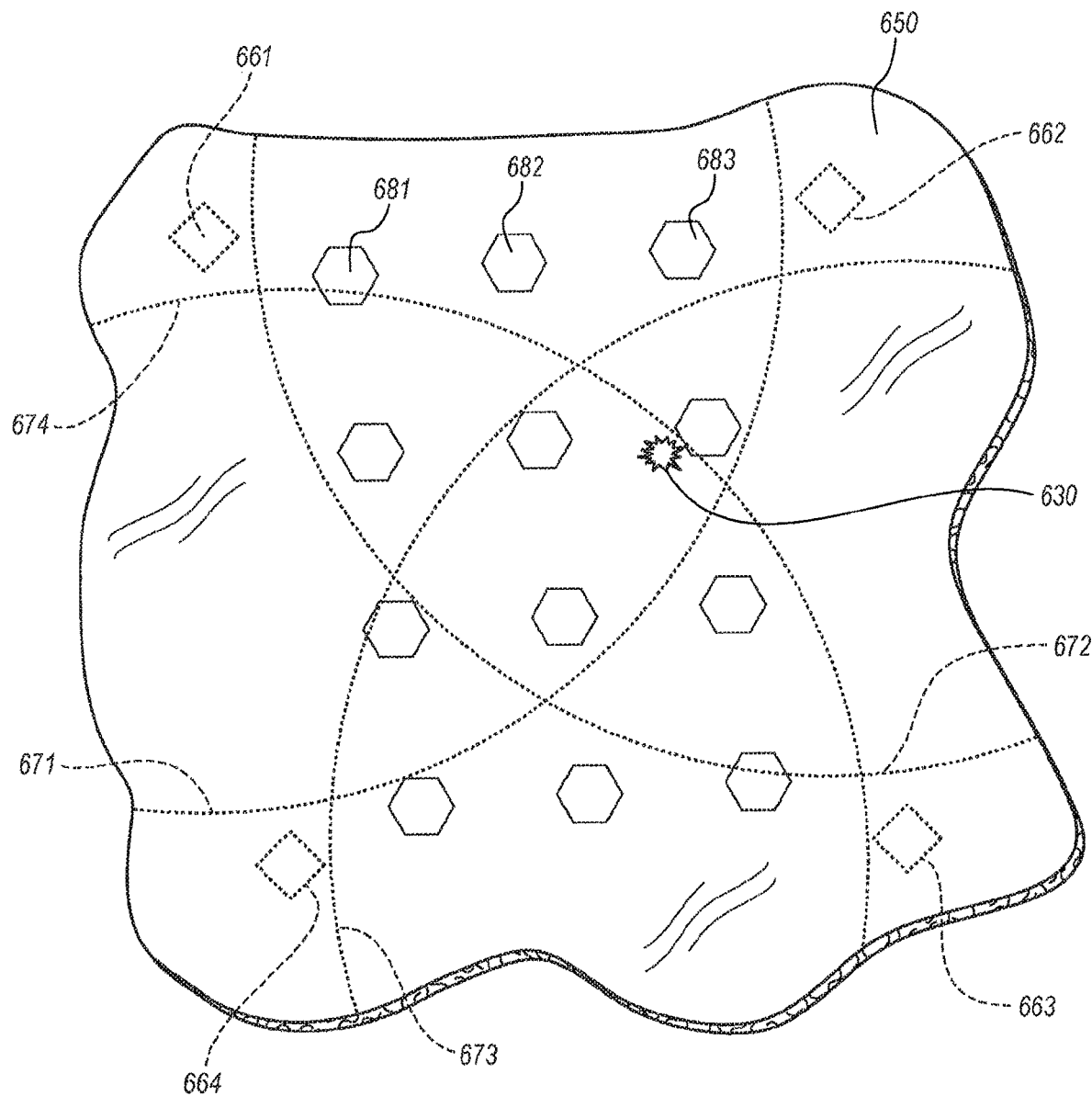
FIG. 28 is a schematic representation of an illustrative method by which a non-contact sensor collects cardiac signals from multiple regions of the cardiac substrate or atrial wall.

FIG. 28 is a schematic representation of an illustrative method by which a non-contact sensor collects cardiac signals from multiple regions of the cardiac substrate or atrial wall. In particular, a non-contact sensing system in which a sensor array is inserted within a chamber of the heart but does not contact the wall of the heart, such as the system depicted in and described with respect to FIGS. 15-24, can be used in the method. A portion of the atrial wall 650 is shown. The sensor array (e.g., the balloon or basket with multiple sensors, such as that used in the EnSite® array) can project potentials to the atrial wall 650 in a manner such as shown in FIG. 21. Each sensor may project the potentials over an area 671, 672, 673, 674 of the atrial wall 650, such that each area 671, 672, 673, 674 represents a sensed wall region. A center point of each projected potential is shown at the diamonds 661, 662, 663, 664, which may also be referred to as the projected potentials. As can be seen in FIG. 28, the projected potentials may overlap one another. The sensor potentials can be the average of the wall potential sensed through a blood volume, such as depicted in FIG. 21.

The projected potentials can be used to estimate the actual potentials at the atrial wall 650. Various positions at which potential estimations may be provided are depicted as hexagons, such as the estimated potential regions 681, 682, 683, etc. For each position, the estimated potential may be obtained by interpolating the projected potentials 671, 672, 673, 674.

Electrocardiograms of the wall region 650 may be obtained from the interpolated or estimated potentials 681, 682, 683, etc. The electrocardiograms may be evaluated, processed, manipulated, or used in any suitable manner to identify a location of a driver 630. Methods for using such electrocardiograms to identify the positions of the drivers 630 are discussed above (e.g., in FIGS. 14A-14C) and below. Following is the discussion of another method for identifying the position of a driver 630 and treating AF.

Figure 29:
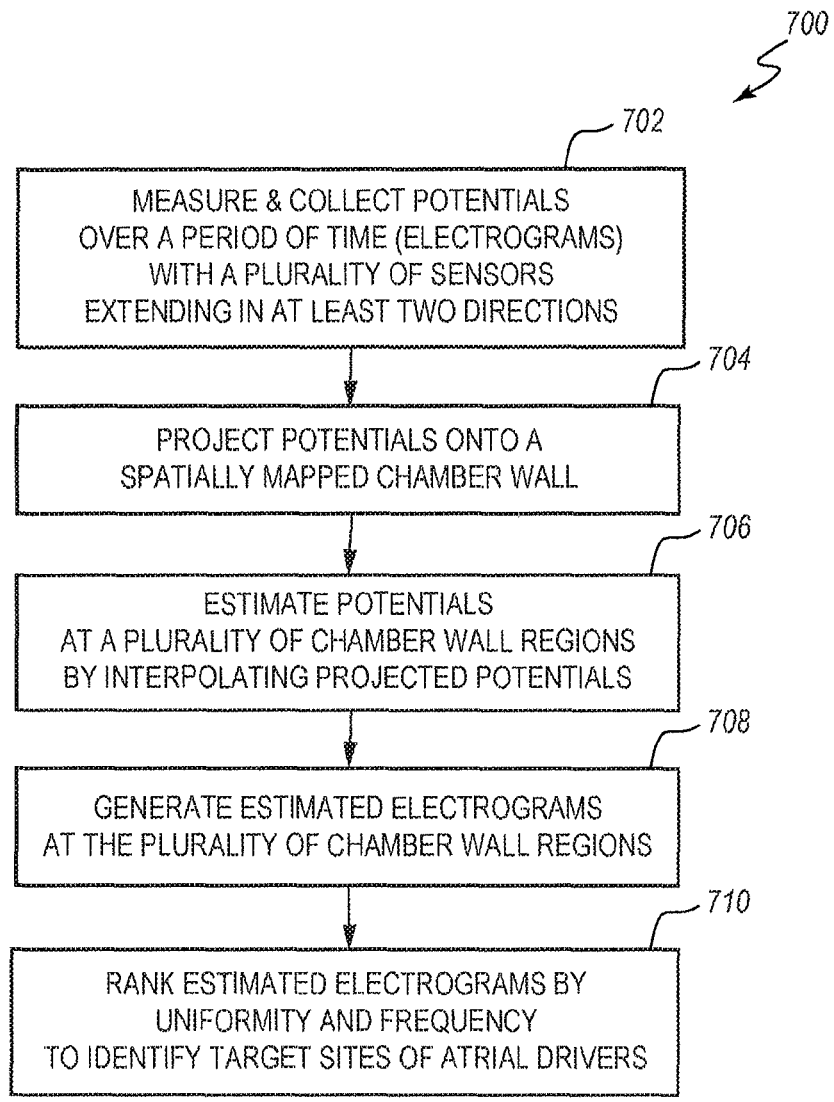
FIG. 29 is a flowchart depicting an illustrative method of treating atrial fibrillation.

FIG. 29 is a flowchart depicting a method of treating AF. At stage 702, potentials of the wall region 650 are measured and collected over a period of time (e.g., in the form of one or more electrocardiograms). The measurements may be made via a plurality of sensors that extend in at least two dimensions. For example, as shown in FIG. 21, the illustrated sensor array can include four sensors that are coplanar. In some embodiments, the sensors may be extend in three dimensions.

At stage 704, potentials are projected onto the wall 650. The wall 650 may be spatially mapped. At stage 706, potentials at a plurality of chamber wall regions (e.g., the regions 681, 682, 683) are estimated by interpolating projected potentials. At stage 708, electrograms are estimated at the plurality of chamber wall regions. At stage 710, the estimated electrograms are ranked to identify target sites of atrial drivers. Suitable ranking algorithms are discussed above, and can include weighting of the electrograms based on their uniformity and/or frequency. Other ranking factors may include amplitude, wave shape, etc. The target sites thus identified may subsequently be targeted and ablated (e.g., focal ablation).

Figure 30:
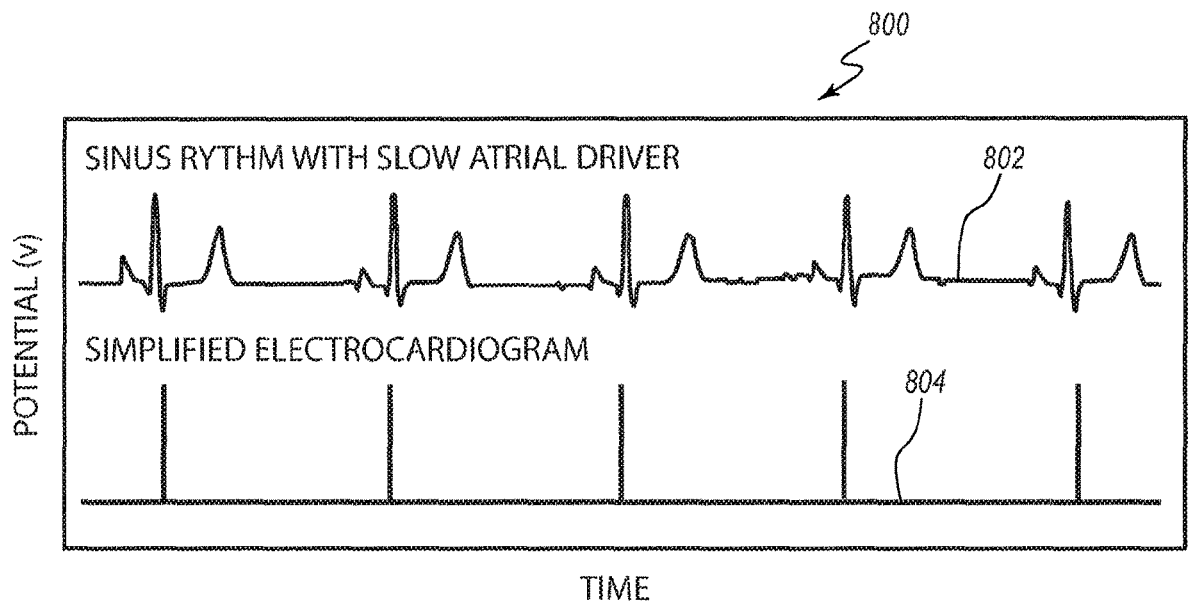
FIG. 30 is a plot depicting an electrocardiogram of a patient who has a sinus rhythm with intermittent suppression by a repetitive slow atrial driver, along with a simplified electrocardiogram in which only the major voltage peaks are represented.

FIG. 30 is a plot 800 depicting an electrocardiogram of a patient who has a normal sinus rhythm and a simplified representation of the electrocardiogram. In particular, the upper curve 802 depicts a trace electrocardiogram that may be obtained in any suitable manner, including any of the various methodologies disclosed herein, whether by non-contact or contact sensors within the heart or other sensors outside of the heart (e.g., at the skin of a patient). In some embodiments, sensors such as described above with respect to 23, 25A, 25B, and 26 may be used. In other or further embodiments, sensors such as described below with respect to FIGS. 39, 40, and 43 may be used.

The lower curve 804 depicts a simplified version of the electrocardiogram, wherein only the major voltage peaks are represented. Such simplified versions of waveforms will be used in additional plots hereafter. Accordingly, it should be understood that in many instances, although plots merely showing discrete peaks may be illustrated in some of the drawings, the plots in fact have more complicated waveforms when measured by any of a variety of types of sensing equipment.

Figure 31:
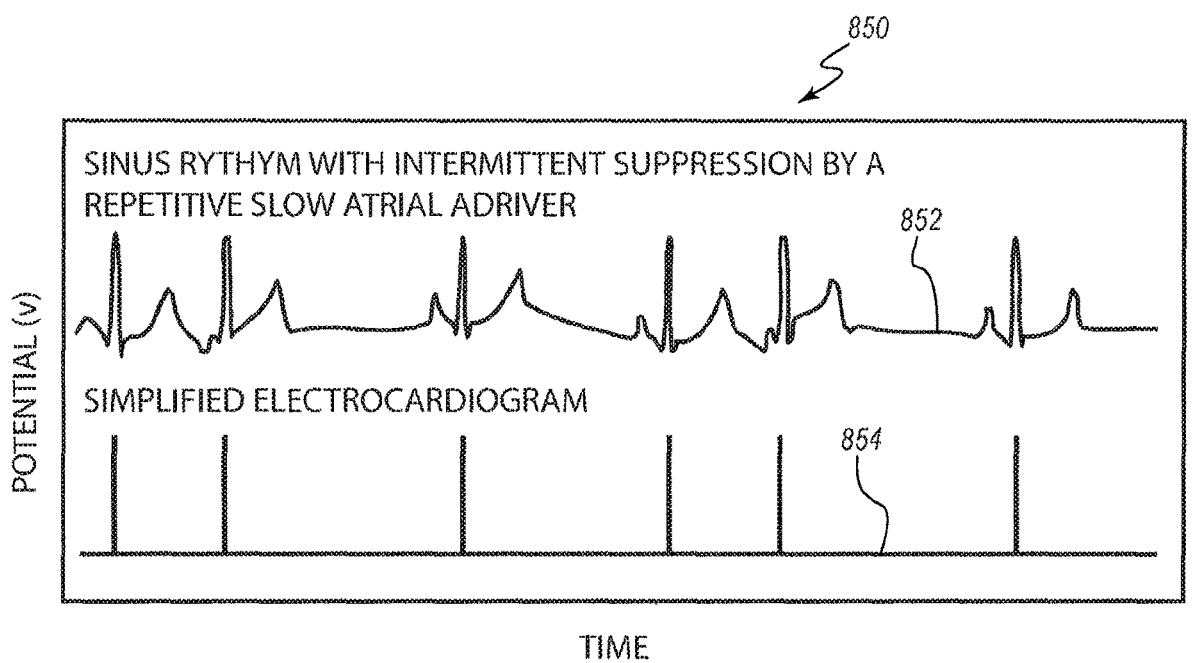
FIG. 31 is a plot depicting an example of a sinus rhythm electrocardiogram, along with a simplified electrocardiogram in which only the major voltage peaks are represented.

FIG. 31 is a plot 850 depicting an electrocardiogram of a sinus rhythm with intermittent suppression by a repetitive slow atrial driver. The upper curve 852 shows the voltage readout as a function of time as it may actually be perceived by a sensor, whereas the lower curve 854 is a simplified version of the electrocardiogram in which only the major voltage peaks are represented, such as discussed above.

FIG. 32A is a schematic representation of a portion of a cardiac substrate 950, or atrium wall, having a primary atrial driver 931 that generates a regular series of wavefronts 951, 952, 953, 954, 955, 956 of electrical impulses that propagate toward a secondary atrial driver 932, which may also be referred to as a bystander driver that is suppressed. The secondary driver 932 may be suppressed by dominant signals received from the primary driver 931 in the same way that occasional primary driver signals may be suppressed by neighboring drivers (which is discussed below with respect to FIGS. 34A and 34B). The secondary driver 932 is depicted in FIG. 32A as not generating any wavefronts that propagate toward the primary driver 931 due to suppression from the primary driver 931. The primary driver 931 can be a rapid, repetitive focal point or focal region of the cardiac substrate that initiates the electrical wavefronts. Without being limited by theory, primary drivers 931 may be found at or embodied in pulmonary veins, extra pulmonary veins, ectopic sites, scar borders, ganglions, and/or anatomic boundaries.

Any suitable sensor or sensor array may be used to detect electrical signals at the region 980, which is depicted as a hexagon, although the detection region need not in actuality be hexagonal. In FIG. 32A, the region 980 is concentric with the primary driver 931 for ease in the present discussion. Similar concentric arrangements are also disclosed in subsequent drawings. Accordingly, a sensor may be positioned to detect a wavefront as it is generated or soon after it is generated. Such an arrangement can simplify the present discussion and analysis. However, it should be understood that in various methods of detecting drivers, the sensors may be positioned at a distance from the drivers, but algorithms such as discussed herein can be used to locate the driver based on information gathered from multiple sensors. Accordingly, some sensors that can obtain electrical data from multiple portions of the atrial wall simultaneously can be useful in identifying the location of drivers.

FIG. 32B is a schematic plot 990 illustrating the electrical signals (point-based assessment of an electrical wave), or waveforms, detected at the region 980 of the cardiac substrate. The signals wavefronts 951, 952, 953, 954, 955, 956 are represented as discrete pulses of voltage. In the illustrated embodiment, the wavefronts 951, 952, 953, 954, 955, 956 have a predictable, repeated period and a consistent amplitude. The presence of the primary driver 931 at or near the region 980 could be readily determined from a plot such as the plot 990. For example, in a method of treating AF, such as those described above and below, the electrogram associated with the plot 990 could be evaluated relative to electrograms obtained from neighboring regions to determine that the region 980 is at or near a driver (i.e., the driver 931). The regularity, frequency, and/or other properties of the wavefronts 951, 952, 953, 954, 955, 956, as compared with the same properties of wavefronts obtained from neighboring regions, can be used in identifying the region 980 as a likely candidate for the location of a primary driver.

FIG. 33A is a schematic representation of another portion of a cardiac substrate 1050 having a primary atrial driver 1031 that generates a regular series of wavefronts 1051, 1052, 1053, 1054, 1055 of electrical impulses that propagate toward a secondary atrial driver 1032. In the illustrated arrangement, the secondary atrial driver 1032 is stable and likewise generates a regular series of wavefronts 1071, 1072, 1073 of electrical impulses that propagate toward the primary atrial driver 1031. In the illustrated embodiment, the secondary driver 1032 is oriented near a boundary 1060, such as an anatomical boundary, damaged tissue, non-conducting cardiac tissue, and/or a scar. In this scenario, both drivers 1031, 1032 persist due to the boundary 1060. That is, the boundary 1060 does not allow the more rapidly firing primary driver 1031 to suppress the slower secondary driver 1032. Accordingly, although a frequency of the wavefronts produced by the secondary atrial driver is lower than a frequency of the wavefronts produced by the primary atrial driver, the boundary 1060 between the two drivers 1031, 1032 allows the secondary driver 1032 to not be suppressed by the wavefronts 1051, 1052, 1053, 1054, 1055 and thus generate its own wavefronts 1071, 1072, 1073. In other scenarios, the distance between the primary driver 1031 and secondary driver 1032, the organization of the propagating waves initiated by the secondary driver 1032, and/or the frequency and amplitude of the secondary wavefronts may prevent the secondary wavefronts from suppressing the primary driver 1031.

FIG. 33B is a schematic plot 1090 illustrating the electrical signals (e.g., waveforms) detected at a region 1080 of the cardiac substrate 1050 designated by a hexagon in FIG. 33A. The plot 1090 illustrates that the signals generated by each of the primary and secondary drivers 1031, 1032 are regular and have a predictable, repeated period. Moreover, neither set of waveforms 1051, 1052, 1053, 1054, 1055; 1071, 1072, 1073 produced by either driver suppresses operation of the other driver 1032, 1031.

FIG. 34A is a schematic representation of another portion of a cardiac substrate 1150 having a primary atrial driver 1131 that generates a regular series of wavefronts 1152, 1153, 1154, 1156, 1157 of electrical impulses that propagate toward a secondary atrial driver 1132. The secondary atrial driver 1132 is stable and likewise generates a regular series of wavefronts 1171, 1172, 1173, 1174, 1175, 1176 of electrical impulses that propagate toward the primary atrial driver 1131. A frequency of the wavefronts produced by the secondary atrial driver 1132 is lower than a frequency of the wavefronts produced by the primary atrial driver 1131. Certain electrical wavefronts of the secondary driver 1132 can occasionally suppress wavefront generation by the primary driver 1131, typically at predictable intervals. In particular, in the illustrated embodiment, every third wavefront produced by the secondary atrial driver 1132 suppresses what would be every fourth wavefront (i.e., 1151, 1155) of the primary driver 1131. In this scenario, there is irregularity of the rapid primary driver 1131 due to intermittent suppression from the secondary driver 1132 at a lower frequency that penetrates the primary driver 1131 due to penetration of the secondary wavefronts into the region of the primary driver 1131 at times shortly after electrical tissue recovery in the region of the primary driver 1131.

Without being limited by theory, suppression, such as just discussed, is a natural phenomenon of cardiac tissue. The tissue can conduct an electrical signal, but then it is transiently dormant while it acquires an inward charge. Accordingly, in situations such as described above with respect to FIG. 34A, whether an electrical signal from the primary driver 1131 or from the secondary driver 1132 will be propagated by the cardiac tissue in the region of the primary driver 1131 can result from whichever waveform hits that region first. Typically, a fast primary driver 1131 will send signals out so quickly that it will suppress all tissue around it. However, in some instances, if the primary driver 1131 does not generate wavefronts quickly enough, another neighboring region can be released from its dormant state and conduct its own electrical signal. If that region starts a wavefront and it reaches the first region just as the first region recovers and begins the process of starting its own wavefront, the first region (e.g., the region of the primary driver 1131) will be suppressed before it can activate its own wavefront. Wavefronts from neighboring, regular drivers can have the same suppressive effects.

For slow drivers, suppression can be common. For example, for some drivers, the sinus node/pacemaker cells may only initiate an impulse every approximately 0.6 to 1.0 seconds, on average. Since cardiac tissue generally recovers within about 150 to about 200 milliseconds, any beat that begins at about 210 to about 600 milliseconds after the sinus beat will get into the sinus node and suppress it so it does not give off the next beat. This phenomenon is depicted in FIG. 31.

In the context of abnormal tissues, driver regions that generate or conduct impulses at high frequencies (e.g., with a period of less than about 150 milliseconds) may be difficult to suppress, even transiently. Without being bound by theory, this is a reason that certain methods of treating AF discussed herein (e.g., the methods in FIGS. 14A-14C) can include steps, stages, and/or algorithms for identifying drivers by regions that have a dominant and/or rapid signal frequency (e.g., algorithms in which uniformity and/or frequency value are weighted, with higher uniformity and higher frequencies indicating stronger likelihood of driver presence). Given that the heart has anatomic boundaries, random triggers that try to send off their own signals at different frequencies, and varied distances between drivers, in some instances, signals from a dominant driver may occasionally be suppressed. Accordingly, additional methods of treating AF can include more or different steps, stages, and/or algorithms for identifying dominant drivers where occasional suppression is present.

FIG. 34B is a schematic plot 1190 illustrating the electrical signals (e.g., waveforms) detected at a region 1180 of the cardiac substrate 1150 designated by a hexagon in FIG. 34A. The plot 1190 demonstrates the periodic suppression of primary wavefronts due to activity of the stable secondary driver. For example, where wavefronts 1151, 1155 from the primary driver 1131 would be expected, only smaller wavefronts from the secondary driver 1132 are present. As discussed further below, certain methods for identifying primary or dominant drivers can take into account such occasional wavefront suppression.

FIG. 35A is a schematic representation of another portion of a cardiac substrate 1250 having a primary atrial driver 1231 that generates a regular series of wavefronts 1252, 1253, 1254, 1256 of electrical impulses that propagate toward a secondary atrial driver 1232. The secondary atrial driver 1232 functions intermittently, and thus the two operational modes of the secondary driver are designated by alternative scenarios (as indicated by the recitation "OR"). In the first or upper alternative, the secondary atrial driver 1232 is dormant, and thus the primary atrial driver 1231 is permitted to generate its electrical wavefronts at a persistent regular frequency. In the second or lower alternative, however, the secondary atrial driver 1232 is temporarily active and generates irregular wavefronts 1271, 1272 that temporarily suppress generation of a wavefront by the primary driver 1231. This intermittent suppression is depicted in the upper alternative by intermittent broken lines where wavefronts 1251, 1255 would be expected. Also, the secondary driver 1232 may be temporarily suppressed by incoming wavefronts initiated by the primary driver 1231 causing the initiation of wavefronts from the secondary driver to be muted. If a period of time between wavefronts initiated by the primary driver occurs, the secondary driver may initiate a wavefront towards the primary driver 1231.

FIG. 35B is a schematic plot illustrating the electrical signals (e.g., waveforms) detected at a region 1280 of the cardiac substrate 1250 designated by a hexagon in FIG. 35A. The periodic suppression of the primary wavefronts 1251, 1255 due to activity of the intermittent secondary driver 1232 is indicated by occasional signals that vary in strength and/or time (e.g., the signals may be slightly earlier than would otherwise be expected, which may result in suppression) from the otherwise regular pattern of signals from the primary driver 1231.

Figure 36:
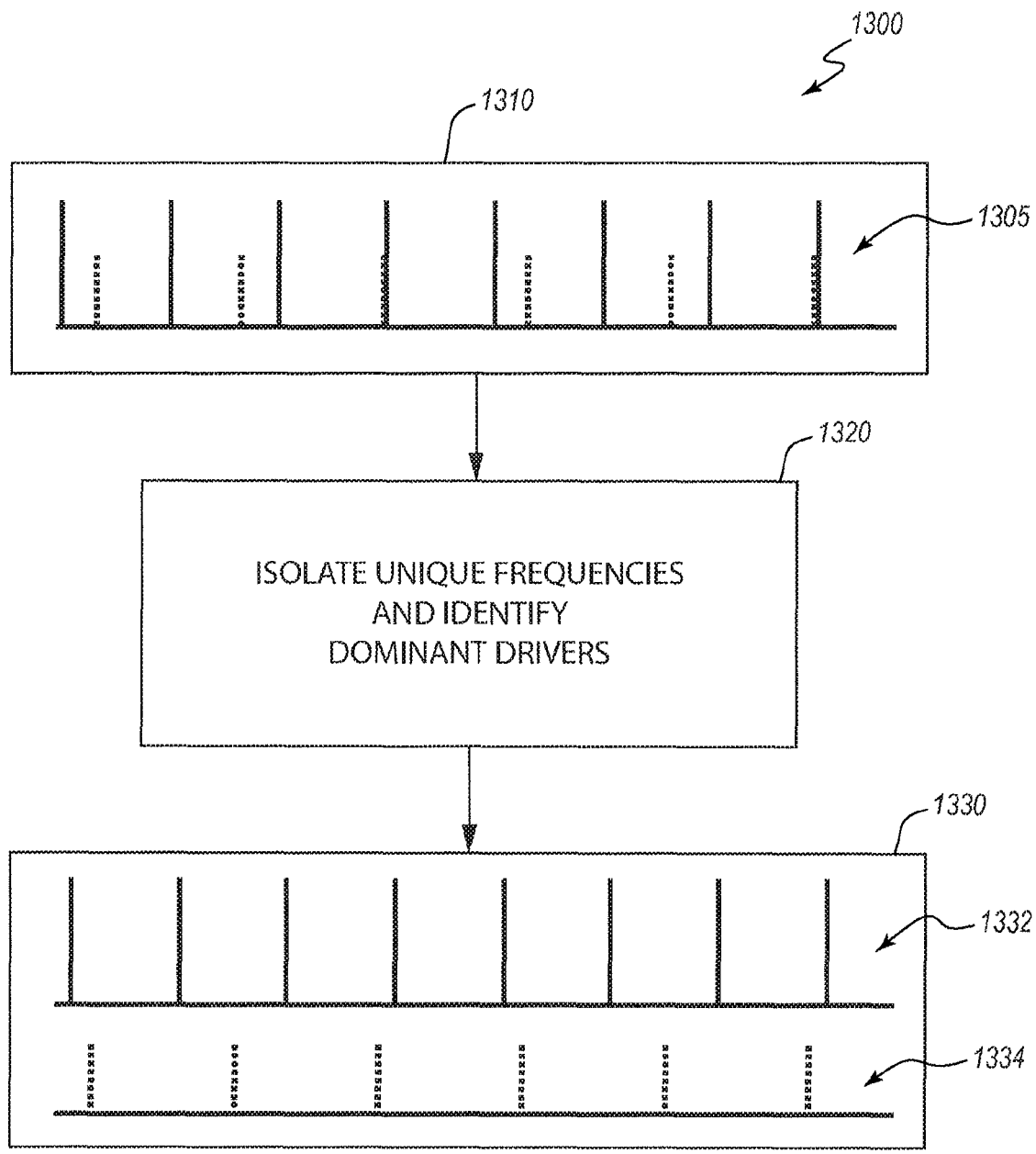
FIG. 36 is a schematic depiction of a portion of an illustrative method for identifying drivers from a trace electrocardiogram, wherein unique frequencies are isolated to identify dominant drivers.

FIG. 36 is a schematic illustration of a portion of a method 1300 for identifying multiple drivers from a trace electrocardiogram. The method 1300 can include obtaining the trace electrocardiogram 1305 in any suitable manner, which is depicted at stage 1310. The electrocardiogram 1305 may be obtained, for example, via any of the sensors and sensor systems described herein, including contact sensors, non-contact sensors, and/or sensors positioned at an exterior of a patient. At stage 1320, unique frequencies from the electrocardiogram 1305 are isolated and dominant drivers are identified. Although these activities are depicted as occurring in a single step in FIG. 36, in some embodiments, the isolation of unique frequencies and the identification of dominant drivers may be carried out in distinct steps. Isolation of the dominant frequencies may be performed in any suitable manner, such as, for example, via a Fourrier transform and/or any other suitable algorithm. Identification of dominant drivers may involve identifying a specific region on a three-dimensional map of the heart that is responsible for a dominant frequency. Mapping of the heart and correlation of a signal source to a specific region of the resultant map may be performed in any suitable manner, such as, for example, any methodology discussed above. One or more portions of the isolation and/or identification steps may be performed via a computer or computer program. FIG. 36 includes a schematic plot 1330, which may be a byproduct of and/or an intermediate result of stage 1320. In particular, the plot 1330 shows provides a visual representation of two unique frequencies, depicted as an upper segment 1332 and a lower segment 1334, that have been isolated from the electrocardiogram 1305. In some instances, the upper segment 1334, with its higher frequency and greater amplitude, may be identified as (or identified as being associated with or being at or near) a primary driver.

Figure 37:
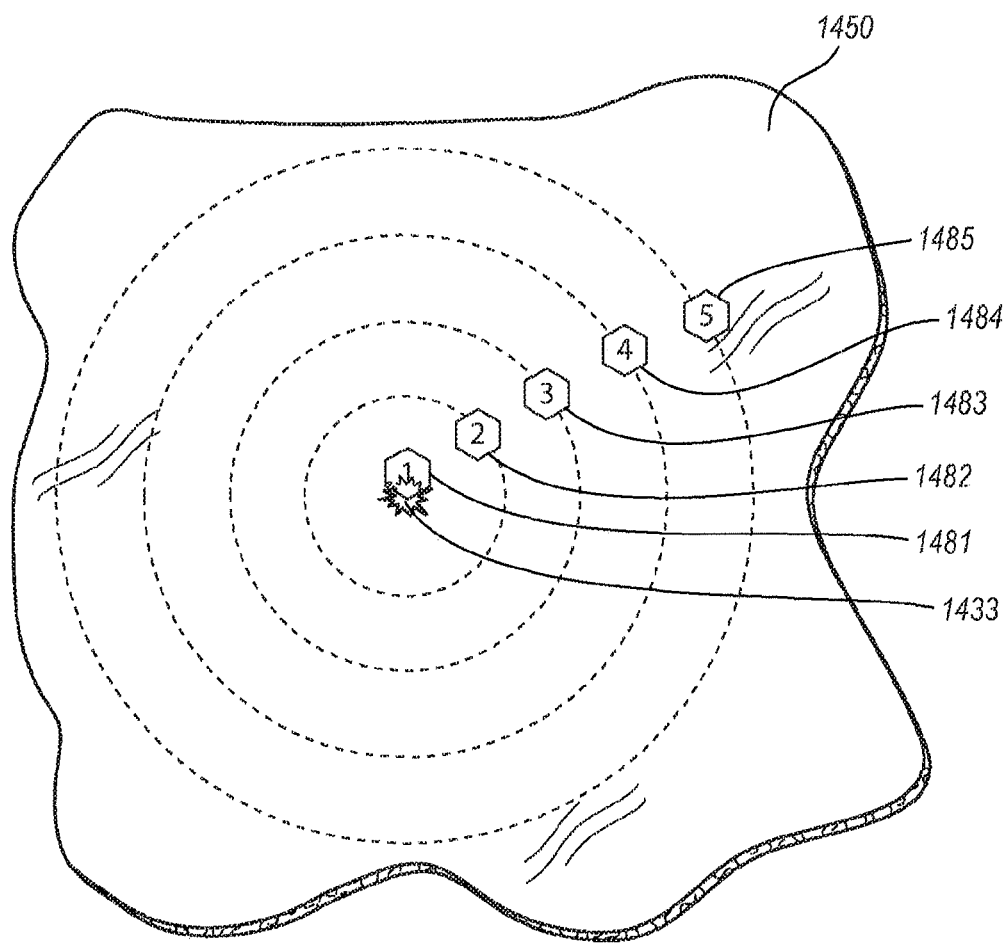
FIG. 37 is a schematic representation of another portion of a cardiac substrate having an atrial driver that is spaced from a series of five different sensors by varying amounts, wherein each sensor is represented by a numbered hexagon.

FIG. 37 is a schematic representation of another portion of a cardiac substrate 1450 having an atrial driver 1433 that is spaced from a series of five different sensors 1481, 1482, 1483, 1484, 1485 (or sensed regions, such as the regions 681, 682, 683 in FIG. 28) by varying amounts. Each sensor or sensed region is schematically represented by a numbered hexagon, although the region sensed may not, in fact, be hexagonal. Moreover, it may be desirable merely to sense at various distances from the driver 1433, and not necessarily in a straight line. The distances are represented by broken-lined concentric circles. Accordingly, although in the illustrated arrangement, the sensors 1481, 1482, 1483, 1484, 1485 are arranged in a straight line, the signals sensed thereby that originate at the driver 1433 will generally be the same at any point along the circle associated with that sensor. However, signals that originate at positions that are spaced from the driver 1433 will appear at different times along each circle. As can be appreciated from the foregoing, in order to locate an atrial driver 1433, particularly where the position of the atrial driver 1433 is not known from the outset, it can be advantageous to have sensors so as to cover a multi-dimensional surface of the wall 1450, rather than merely a one-dimensional line along the wall 1450. For example, a series of sensors may desirably be placed on the wall in two dimensions, such that they cover an area when viewed in a plan view. In further embodiments, the sensors may further follow a three-dimensional contour of the wall 1450. Non-contact sensors such as described above can obtain measurements in three-dimensions in this manner. Contact sensors such as shown in FIGS. 25A and 25B may also provide such three-dimensional data. Additional contact sensors that are suitable for obtaining such measurements are described below with respect to FIGS. 39, 40, and 43.

Figure 38A:
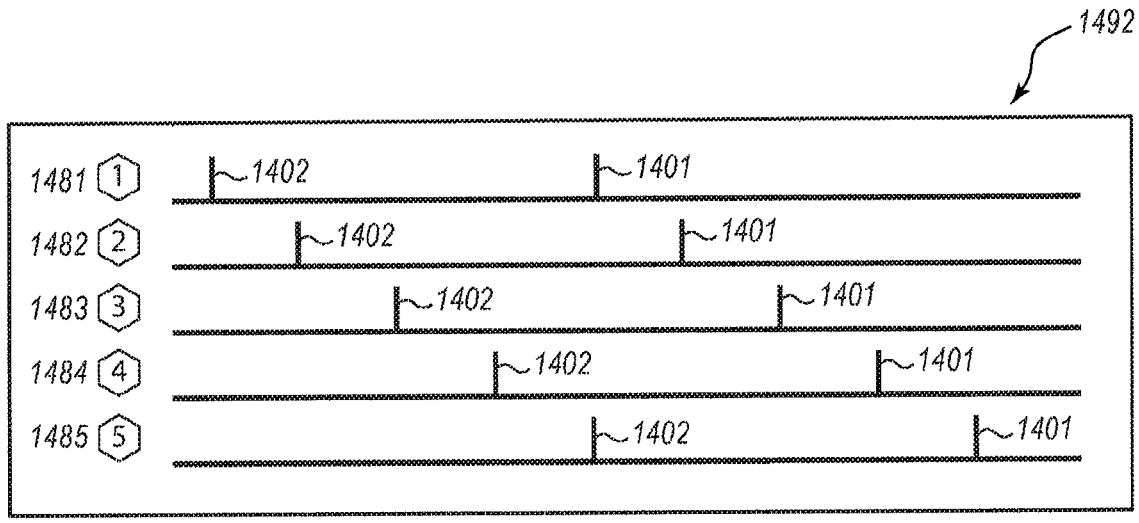
FIG. 38A is a schematic plot illustrating the electrical signals (e.g., waveforms) that may be detected by each of the sensors shown in FIG. 37 when the atrial driver is a primary driver from which wavefronts regularly propagate outwardly.

FIG. 38A is a schematic plot 1492 illustrating the electrical signals (e.g., waveforms) that may be detected by each of the sensors 1481, 1482, 1483, 1484, 1485 when the atrial driver 1433 is a primary driver from which wavefronts regularly propagate outwardly. For example, a signal or wavefront 1401 may first be detected by the sensor 1481, then by the sensor 1482, then by the sensor 1483, then by the sensor 1484, and finally by the sensor 1485. The wavefront 1401 thus may clearly propagate in a direction away from the driver 1433. The same is also true of a subsequently generated wavefront 1402.

Figure 38B:
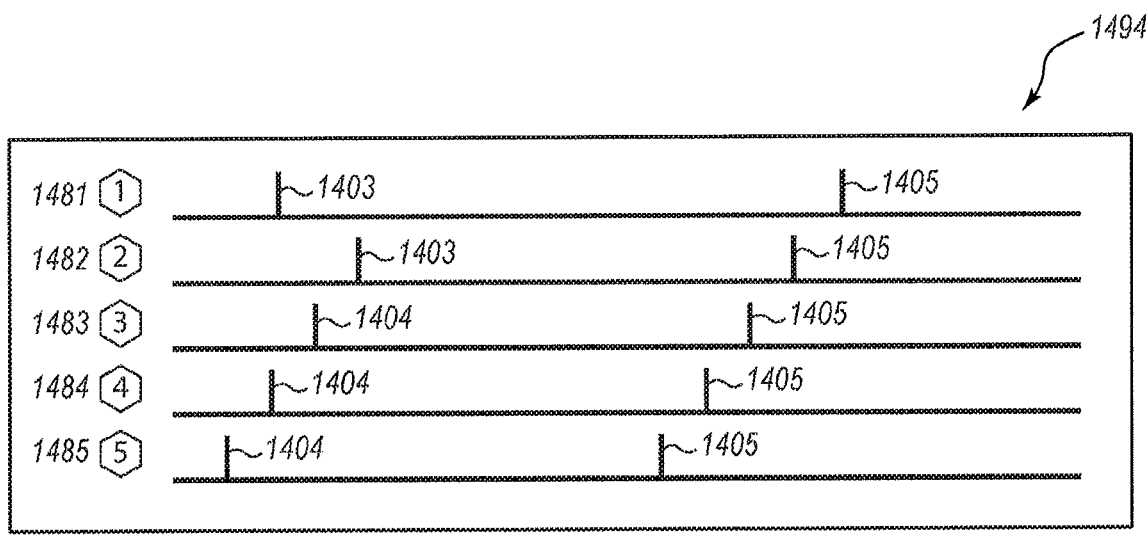
FIG. 38B is a schematic plot illustrating the electrical signals (e.g., waveforms) that may be detected by each of the sensors shown in FIG. 37 when the atrial driver is a secondary driver that has a lower frequency than a neighboring driver (e.g., a neighboring primary driver) and/or that generates wavefronts intermittently, such that wavefronts are shown initially propagating outwardly relative to the innermost sensor, but thereafter wavefronts are shown propagating inwardly toward the innermost sensor.

FIG. 38B is a schematic plot 1494 illustrating the electrical signals (e.g., waveforms) that may be detected by each of the sensors 1481, 1482, 1483, 1484, 1485 when the atrial driver 1433 is instead a secondary driver that has a lower frequency than a neighboring driver (e.g., a neighboring primary driver) and/or that generates wavefronts intermittently. Accordingly, the secondary driver 1433 may be subject to signal suppression, such as discussed above. Due to the secondary, or less dominant nature of the atrial driver 1433 (as may result, for example, from the driver 1433 having a lower frequency), wavefronts may generally propagate toward the secondary driver 1433, rather than away from it. For example, in the illustrated plot 1494, the driver 1433 may occasionally generate a wavefront, such as the wavefront 1403. This wavefront 1403 may start to propagate outwardly from the driver 1433, as shown by the later detection of the wavefront 1403 by the sensor 1482. However, by the time the wavefront 1403 reaches the position of the third sensor 1483, a different wavefront 1404 from some other source (e.g., a neighboring primary driver) may have already triggered the cardiac tissue in regions external to the circle associated with the sensor 1482. Indeed, the wavefront 1404 was previously sensed by the sensor 1484, and was sensed prior to that by the sensor 1485. Accordingly, the sensors 1485, 1484, 1483 are shown as having detected the wavefront 1404 propagating toward the driver 1433. The wavefront 1404 does not further trigger the cardiac tissue in the regions about the sensors 1482 and 1481 in the illustrated arrangement, however, since the wavefront 1403 has already triggered the cardiac tissue and it has not yet recovered.

Moreover, before the slower-operating driver 1433 is able to generate another wavefront of its own, it is triggered by another wavefront 1405 that originated elsewhere (e.g., at the neighboring primary driver). This wavefront 1405 is shown in the plot 1494 as propagating toward the driver 1433, given that wavefront 1405 was first detected by the outermost sensor 1485, and was then detected by the progressively more inwardly positioned sensors 1484, 1483, 1482, and then 1481.

In view of the foregoing, it may be said that the driver 1433 occasionally initiates wavefronts that propagate outwardly. However, wavefronts predominantly propagate inwardly toward the driver. The property of wavefronts generally propagating outwardly from primary drivers and propagating inwardly toward secondary drivers may be used in locating primary drivers, such as in the methods described below with respect to FIGS. 41 and 42.

FIG. 39 is a plan view of an embodiment of a sensor assembly 1500 that may be useful in obtaining measurements regarding wavefront propagation, among other wavefront and/or waveform properties. The sensor assembly 1500 can include an array of sensors 1502 that extend in at least two orthogonal directions, or two dimensions (e.g., in the X- and Y-directions of the illustrated planar view). The sensors 1502 may extend in a third direction as well (e.g., in the Z-direction into/out of the page, in the illustrated view) to readily conform to a three-dimensional contour of a heart wall 1550. Each sensor 1502 may be capable of detecting electrical potentials of a region 1580 of the heat wall 1550. The sensors 1502 may define a multi-dimensional (2-dimensional or 3-dimensional) sensing area. In some embodiments, the sensor assembly 1500 may operate in a unipolar mode, e.g., in which each sensor 1502 detects a potential relative to a common voltage. In other or further embodiments, the sensor assembly 1500 may operate in a bipolar mode, e.g., in which potential differences between adjacent sets of sensors 1502 are detected.

In the illustrated embodiment, the sensor assembly 1500 includes a positioning catheter 1506 that can be used to dynamically change a position of the sensor array. In some applications, the sensor 1500 is positioned on the substrate 1550 for a period of time that atrial fibrillation is observed (e.g., over multiple heart beats), and in further applications, electrogram data can be acquired simultaneously with near field and/or far field electrogram data. Methodologies, such as those disclosed above and below, can be used to identify potential atrial drivers and portions of the sensed area can be recorded or identified as potential treatment targets. The sensor 1500 may then be relocated to a new portion of the substrate 1550. In some embodiments, the sensor assembly 1500 can provide a more detailed view of a smaller portion of the cardiac wall 1550 than may be obtained with certain embodiments of the sensor depicted in FIGS. 25A-25B.

The sensor assembly 1500 can further include a support structure 1504, such as a wire or narrower catheter, to which the sensors 1502 are mounted. In the illustrated embodiment, the support structure 1504 defines a single branch that is spiraled. In some embodiments, the support structure 1504 may be resiliently flexible, and may have a springing action. For example, in the illustrated embodiment, the support structure 1504 may be capable of concave or convex deformations relative to a center point of the spiral, which may aid in following a contour of the heart wall. As previously mentioned, the sensor array may be particularly useful in detecting the direction of propagation of wavefronts relative to a driver 1530, as depicted by the broken arrows.

In some embodiments, the sensor assembly 1500 can comprise a Reflexion HD™ High Density Mapping Catheter, which is available from St. Jude Medical of Little Canada, Minn.

FIG. 40 is a plan view of another embodiment of a sensor assembly 1600 that includes multiple contact sensors 1602 that can extend along a cardiac substrate 1650 in at least two orthogonal directions, or stated otherwise, in at least two dimensions, to define at least a two-dimensional sensing area. Like the sensor assembly 1500, the sensor assembly 1600 may also be configured to extend in three dimensions to follow a contour of the heart wall 1650. In various embodiments, the sensor assembly 1600 may be operated in a unipolar and/or in a bipolar mode.

Each sensor 1602 of the assembly 1600 may be capable of detecting electrical potentials of a region 1680 of the heat wall 1650. The sensors 1602 may define a multi-dimensional (2-dimensional or 3-dimensional) sensing area. In the illustrated embodiment, the sensor assembly 1600 includes a positioning catheter 1606 that can be used to dynamically change a position of the sensor array. In some embodiments, the sensor assembly 1600 can provide a more detailed view of a smaller portion of the cardiac wall 1650 than may be obtained with certain embodiments of the sensor depicted in FIGS. 25A-25B. The sensor assembly 1600 can further include a support structure 1604, such as one or more wires or narrower catheters, to which the sensors 1602 are mounted. In the illustrated embodiment, the support structure 1604 defines five branches that extend from a distal end of the positioning catheter 1606. In some embodiments, the support structures 1604 may be resiliently flexible, and may have a springing action. The sensor array may be particularly useful in detecting the direction of propagation of wavefronts relative to a driver 1630, as depicted by the broken arrows.

In some embodiments, the sensor assembly 1600 can comprise a PentaRay® NAV Catheter, which is available from Biosense Webster® of Diamond Bar, Calif.

Figure 41:
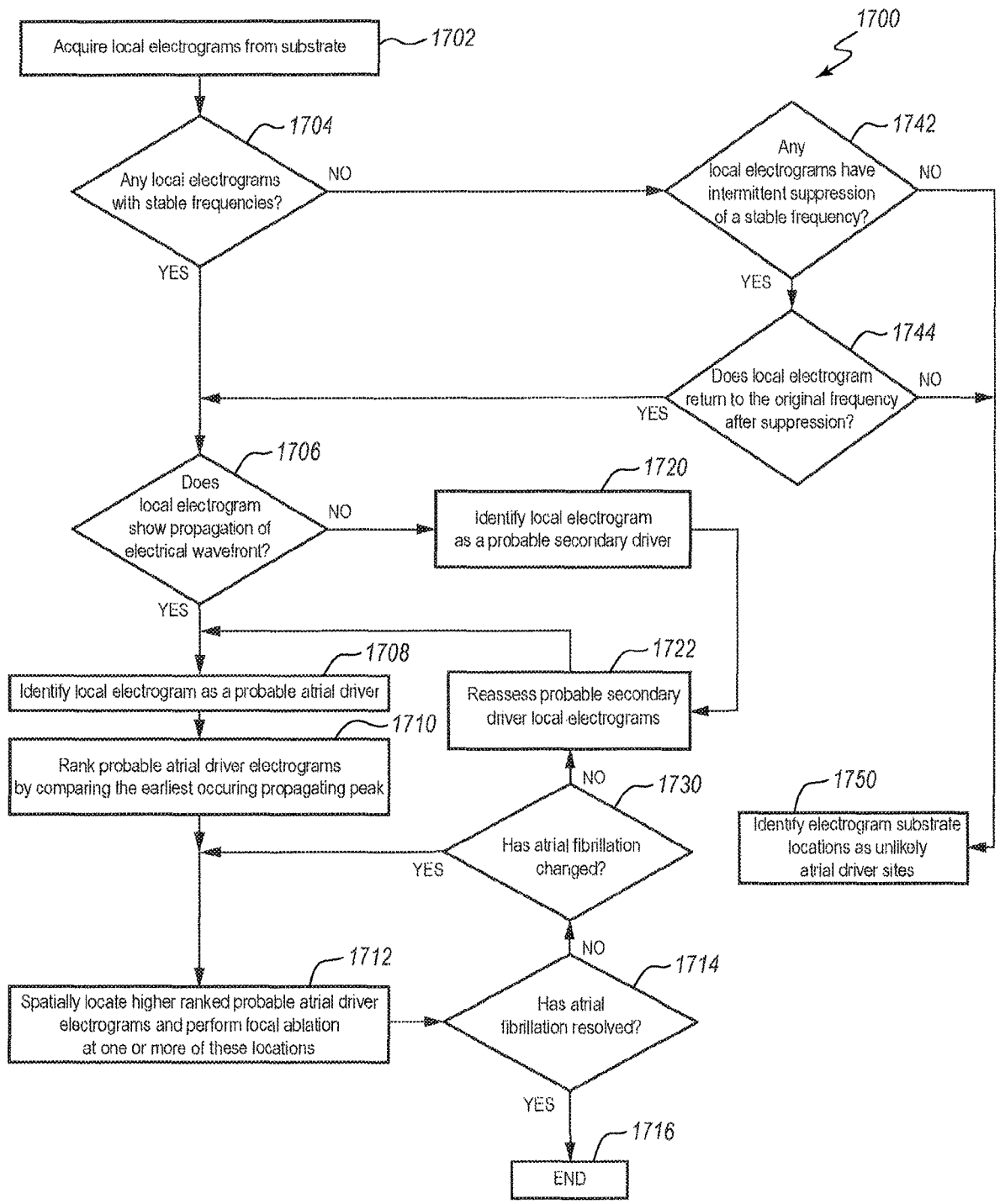
FIG. 41 is a flowchart depicting an illustrative method of treating atrial fibrillation.

FIG. 41 is a flowchart depicting a method of treating atrial fibrillation 1700. The method can exploit the properties of drivers discussed herein to aid in identifying probable or actual positions of those drivers and subsequently ablating (e.g., focal ablating) the drivers.

At stage 1702, local electrograms are acquired from a cardiac substrate. The local electrograms may be acquired in any suitable manner, such as discussed herein. For example, in some embodiments, non-contact sensor arrays may be used. In other embodiments, sensor arrays (e.g., as provided by the sensor assemblies 1500, 1600) may be used.

At stage 1704, it is determined whether any local electrograms have stable frequencies. If the determination is affirmative, the method continues on to stage 1706, if not, the process progresses to stage 1742.

At stage 1706, it is determined whether the local electrogram, or a series of local electrograms (e.g., such as described above with respect to FIGS. 38A and 38B) show a propagation of an electrical wavefront. In particular, it is determined whether an electrical wavefront is shown predominantly propagating in a single outward direction, or outwardly from a region. If the determination is affirmative, then the process continues to stage 1708. If, however, the determination is negative, or if the wavefronts predominantly propagate in a direction toward a given region, then the process continues to stage 1720. The determination at stage 1706 may include comparison of different electrograms. For example, all electrograms may be compared with one another, and physical locations of the heart that are associated with each electrogram may be taken into consideration to determine in what direction an electrical wavefront propagates.

At stage 1708, a local electrogram is identified as a probable atrial driver. Stated otherwise, a position of the heart wall that is responsible for generation of the electrogram having the properties that led to the arrival at stage 1708 is identified as a position at which a primary driver is likely to be located. For example, a three-dimensional image or model of the heart (e.g., the image 191 discussed above) may be marked with a color or other indicator to identify the potential driver.

At stage 1710, the probable atrial driver electrograms are ranked to determine which electrogram is most likely to be associated with an atrial driver. In some ranking algorithms, an electrogram is more likely to be associated with an atrial driver if a propagating signal, or peak voltage, occurred there earlier than it did in other electrograms. Stated otherwise, in some processes, early occurrences of a propagating peak are given a greater weight in a weighting algorithm, or are otherwise assigned higher likelihood that an atrial driver is associated with the electrogram. The position of earliest occurrence can yield the most likely position of the driver, in some algorithms.

Other factors may be evaluated instead of, or in addition to, peak propagation at this stage. For example, frequency, stability, waveform shape, and/or other wave properties, such as those discussed above, may be evaluated. In some instances, the positions at which drivers are potentially located that have the highest frequencies are ranked and identified as the most best candidates for ablation.

In some instances, a further stage may occur after stage 1710 in which one or more rankings are mapped to a representation of the heart. For example, a three-dimensional image or model of the heart may be marked with a color or other indicator to identify a potential driver, or target site for ablation. If multiple drivers are identified, with one driver having a higher frequency and one or more further drivers having a lower frequency, such that the higher frequency driver may have a higher likelihood of being a primary driver, the marking or identification may proceed in a manner to distinguish the various drivers from one another. For example, the higher frequency driver may be marked with a color or otherwise identified in a manner that signifies that the position on the heart is likely a driver and is thus a good candidate for ablation, and the one or more lower frequency positions may be identified as less likely positions at which a primary driver is located. Even where only a single potential driver is identified, a similar identification may take place. For example, in some instances, it may be determined that any potential driver having a frequency that is above a threshold value (e.g., having a period of no greater than 100 milliseconds, in some instances) is a good candidate for ablation and thus may be identified accordingly (e.g., by marking a three-dimensional map with a specific color or other indicator). Other thresholds may also be determined. For example, potential positions that exhibit periods at or below a lower threshold may be identified as good driver candidates, positions that exhibit periods between the lower threshold and an upper threshold may be identified as fair driver candidates, and positions that exhibit periods at or above the upper threshold may be identified as poor driver candidates. Other ranking values and identification systems are also contemplated.

At stage 1712, the highest and/or higher ranked probable atrial driver electrograms are located and focal ablation is performed at one or more of the locations. The location may be determined from a map of the heart, which may be directly correlated to the various positions from which the electrograms are gathered, in manners such as discussed above.

At stage 1714, it is determined whether atrial fibrillation has been resolved. If so, then the method is at an end at stage 1716. If not, the method proceeds to stage 1730 to determine whether the atrial fibrillation, though not resolved, has at least changed. If there has been a change, then the method loops back to stage 1712 again. However, if there has been no change, then the method proceeds to stage 1722. In some instances, after an evaluation is made at stage 1714, reconsideration may be made in the setting of isopenaline (isoprotenenol, or "Isuprel").

Reference is again made to stage 1720, the completion of which also results in progression to the stage 1722. At stage 1720, if the decision at stage 1706 is negative, then the local electrogram is identified as a probably secondary driver. Reassessment of whether a probable secondary driver is in fact a primary driver occurs at stage 1722. If it is determined that what was originally considered to be a secondary driver may in fact be a primary driver, then the method can loop back again to stage 1708.

Referring again to stage 1704, if no local electrograms demonstrate stable frequencies, then the method can proceed to stage 1742, at which it is determined whether any local electrograms have intermittent suppression of a stable frequency, or stated otherwise, whether the electrogram would have a stable frequency, but for the existence of intermittent suppression of expected signals or wavefronts at the otherwise stable frequency. If such suppression is or appears to be present (e.g., suppression such as shown in FIG. 34B or 35B), then the method proceeds to stage 1744. If not, then the method proceeds to stage 1750, at which the electrogram substrate locations are identified as unlikely atrial driver sites. The identification can include the marking of a three-dimensional model of the heart in manners such as discussed above.

At stage 1744, it is determined whether the local electrogram returns to the original, regular frequency after suppression. If so, then the method cycles back to stage 1706. If not, then the method cycles back to stage 1750. After arriving at stage 1750, a sensor may be repositioned to a new area of the heart wall (e.g., for some contact sensors), or a new sensing region may be identified (e.g., for other, larger-area contact sensors and/or non-contact sensors that sense over a large region). The method 1700 may then be repeated at the new region of the heart.

The method 1700 can be repeated as treatment progresses. For instance, as an atrial driver location is treated by ablating the cardiac tissue associated with the targeted site, newly acquired sensor data can be acquired and then used to assess the substrate for other probable atrial driver targets.

As with other methods herein, one or more of the stages may be performed by a computer or other specialized equipment. For example, any suitable program that implements algorithms such as described herein is contemplated. Moreover, any suitable subset of stages may constitute a separation method. By way of example, some methods may comprise stages 1702, 1704, 1706, and 1708; further methods may additionally comprise stage 1710; and further methods still may additionally comprise stage 1712. Some methods may comprise stages 1702, 1704, 1742, 1744, 1706, 1708, and/or 1710; and further methods may additionally comprise stage 1712.

Figure 42:
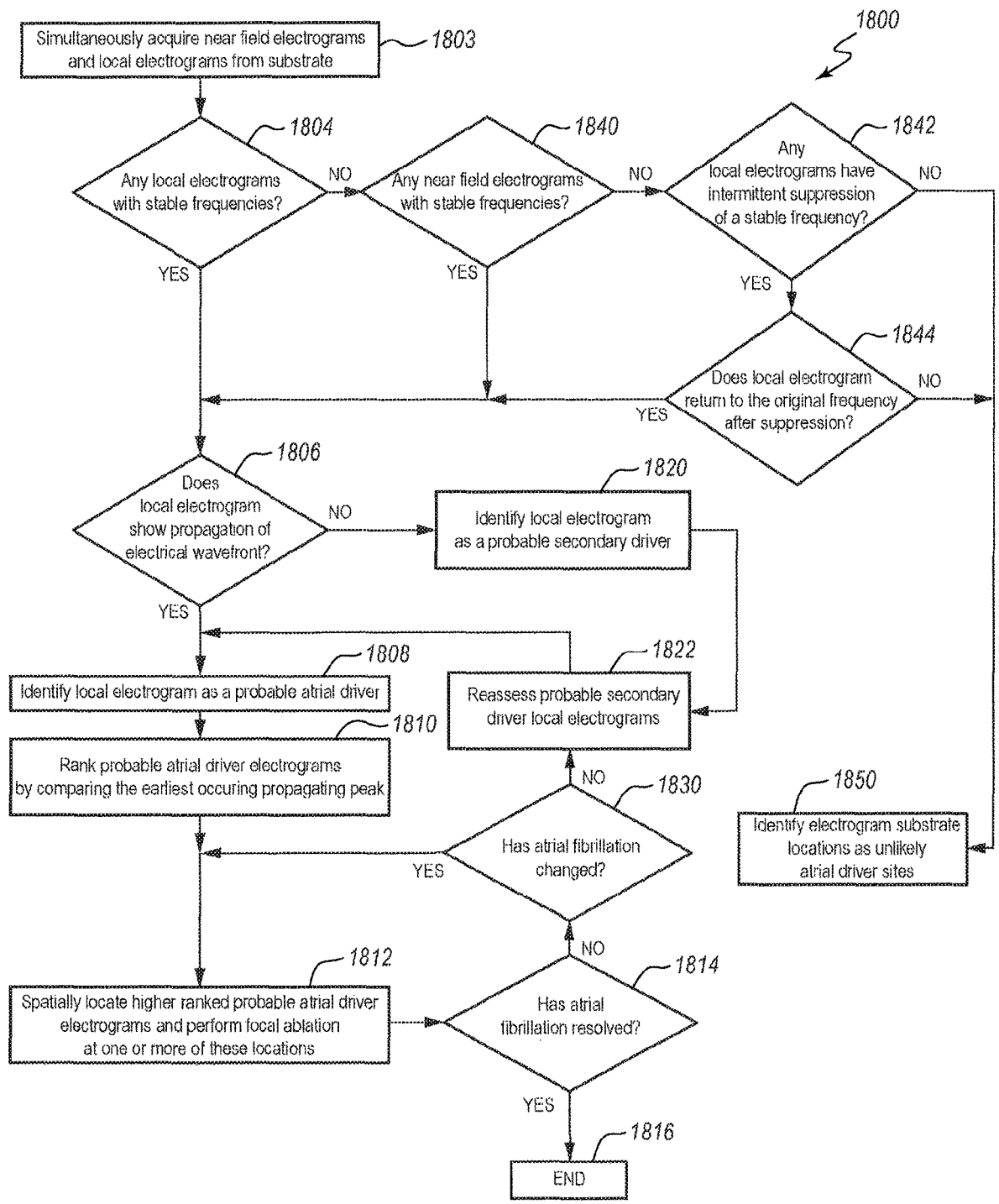
FIG. 42 is a flowchart depicting another illustrative method of treating atrial fibrillation.

FIG. 42 is a flowchart depicting another method of treating atrial fibrillation. The method closely resembles the method 1800. In particular, the stages 1804, 1806, 1808, 1810, 1812, 1814, 1820, 1822, 1830, 1842, 1844, and 1850 can be the same as the stages 1804, 1706, 1708, 1710, 1712, 1714, 1720, 1722, 1730, 1742, 1744, and 1750. However, the method further includes the stages 1803 and 1840. Any suitable subset of the foregoing steps is also contemplated.

The step 1803 resembles the step 1702 discussed above, but further includes acquisition of near field electrograms from the substrate. The collection of the near field and local electrograms can be simultaneous or substantially simultaneous, and may be performed in any suitable manner. The term "near field electrogram" is meant in its ordinary sense.

The method proceeds from stage 1804 to stage 1840 if it is determined that no local electrograms have stable frequencies. If this is the case, then it is determined whether any near field electrograms have stable frequencies. If so, then the method proceeds to stage 1806. If not, then the method proceeds to stage 1842. Accordingly, the stage 1840 can provide another indication that stable frequencies exist relative to a region of the heart.

Either of the methods 1700, 1800 can be combined with other methods disclosed herein to identify and/or isolate drivers. For example, in some methods that include at least some of the stages of the methods 1700, 1800 can further include some or all of the stage of the methods 200, 240, 260, 700. For example, ranking algorithms that weigh the frequency, regularity (or stability), etc. of electrograms, wavefronts, and/or wavefront patterns may be used before, after, or otherwise in conjunction with any suitable stage or stages of the methods 1700, 1800. By way of illustrative example, the stages 702, 704, 706, and 708 of the method 700 may be performed in conjunction with the stages 1702, 1803 of the methods 1700, 1800, and the stage 710 may be performed in conjunction with (e.g., before, after, or simultaneously with) the stage 1710, 1810 of the methods 1700, 1800.

FIG. 43 is a plan view of an embodiment of a sensor assembly 2000 in the process of gathering electrograms from a portion of an atrial wall 2050, wherein a driver 2030 is within a sensing region of the sensor assembly 2050. The sensor assembly 2000 can be of any suitable variety. In the illustrated embodiment, the sensor assembly 2000 includes five separate individual support structures or branches 2004 that radiate from a distal end of a catheter 2006. In certain embodiments, the branches 2004 can be flexible so as to be able to readily move into contact with the atrial wall 2050. Accordingly, although the branches 2004 are consistently illustrated in the drawings as being equally spaced from one another in FIG. 43 and in subsequent drawings, the branches 2004 need not necessarily assume such a symmetrical configuration, in some embodiments. For example, in some arrangements, some or all of the branches 2004 may be closer to each other and/or some or all of the branches 2004 may be spaced further apart from each other than what is depicted in the illustrative drawings. In some embodiments, the sensor assembly 2000 can be configured to detect or otherwise provide information regarding the relative orientations of the branches 2004 such that information regarding the direction in which each branch is pointed and/or the location of each sensor 2002 is known. In some embodiments, the sensor assembly 2000, the sensor assembly 2000 can comprise a PentaRay® NAV Catheter.

Each branch 2004 of the sensor assembly can include a plurality of sensors 2002. Only one of the sensors 2002 is identified by the reference numeral "2002," but each of the sensors is identified in the drawings by its sensor number—S1, S2, S3, S4, S5, S6, S7, S8, S9, S10, S11, S12, S13, S14, S15, S16, S17, S18, S19, S20. In some instances, the sensor assembly 2000 may operate in a unipolar mode in which each of the sensors 2002 detects a potential relative to a common reference voltage. In other instances, the sensor assembly 2000 may operate in a bipolar mode in which sets of adjacent sensors 2002 measure relative potential differences between the sensors. For example, in the illustrated embodiment, when the sensor assembly is operating in the bipolar mode, potential differences between adjacent sets of sensors that are positioned along the same branch are measured. Thus, for example, potential differences between the sensors S13 and S14, between S14 and S15, and between S15 and S16 may be obtained along one branch, and each set of adjacent sensors may thus observe the electrical activity of specific regions 2081, 2082, 2083, respectively, of the atrial wall 2050.

The positioning catheter 2006 may be used to move the distal head of the sensor assembly 2000 to a desired location along the atrial wall 2050. This is depicted by the arrow 2001. In some procedures, the sensor assembly 2000 may be used to map and/or measure electrical activity along a large portion of the atrial wall 2050. In some instances, a substantial portion of the atrial wall 2050 may be observed or measured during the course of a procedure.

In some procedures, the distal head of the sensor assembly 2000 may be moved to a desired position and one or more of the branches 2004 may be moved into electrical contact with the atrial wall 2050. The sensor assembly 2000 may then be held in place for a sufficient time to take a desired set of measurements. In various instances, the sensor assembly 2000 may be held substantially stationary relative to the atrial wall for a period of up to about 200, 400, 600, or 800 milliseconds. In other instances, an observation period may be one or more seconds, or may last for up to one, two, or three heartbeats. In some instances, the sensor assembly 2000 may be held in place for up to a minute as measurements are gathered. After a desired set of data is obtained, the sensor assembly 2000 may be moved to another portion of the atrial wall 2050.

FIG. 43 represents a situation in which a driver 2030 is within a sensing region of the sensor assembly 2000 during an observation event. The driver 2030 regularly propagates wavefronts 2051, 2052, 2053 outwardly in manners such as discussed above. Electrograms obtained by the sensors 2004 may be used to determine the approximate and/or exact location of the driver 2030, as discussed hereafter.

Figure 44A:
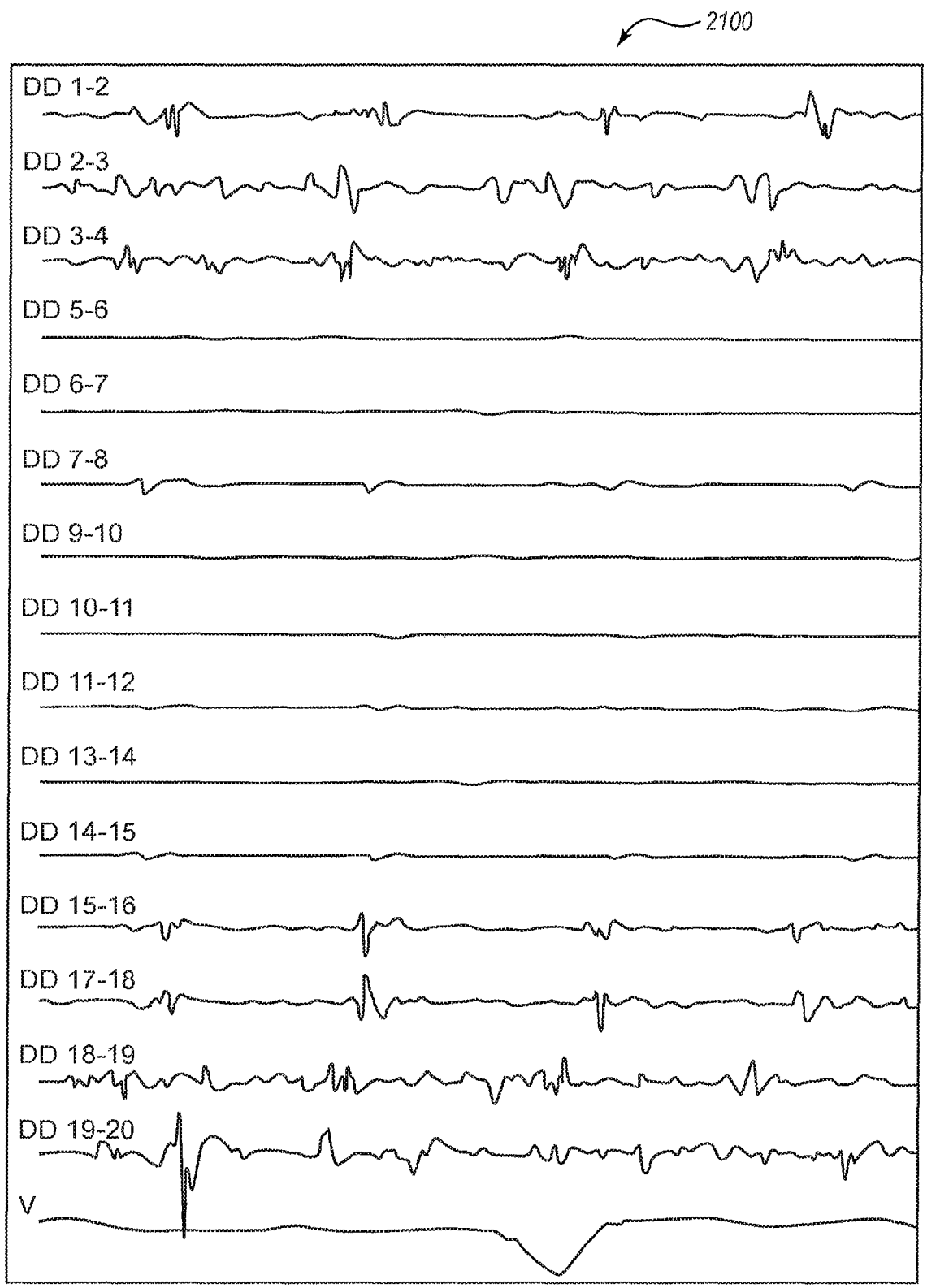
FIG. 44A is a plot that includes electrograms gathered via the sensor assembly and that also shows a base signal of the heart.

FIG. 44A is a plot 2100 that includes electrograms gathered via the sensor assembly 2000 and that also shows a base signal 2102 of the heart. The electrogram obtained via the sensors S1 and S2 is designated DD 1-2, the electrogram obtained via the sensors S2 and S3 is designated DD 2-3, and so on. In the illustrated plot, the electrograms are arranged in ascending order of the sensor number. However, as can be seen in FIG. 44A, such an ordering of the electrograms does not necessarily or always readily reveal a pattern, such as wavefront propagation. It thus may be desirable to rank, sort, rearrange, or otherwise evaluate the electrograms and obtain information that may be used to determine an approximate or exact location of the driver 2030.

In some embodiments, a program implemented by a general purpose computer or dedicated hardware may evaluate and/or rank the electrograms based on one or more properties, such as, for example, waveform unity, frequency, amplitude, shape (e.g., slope, initial direction—whether positive or negative, sharpness, number of peaks or valleys, etc.). Timing may also be a key property used in ranking or sorting the electrograms, and in some instances, earlier presence of a wavefront will receive a higher ranking.

Figure 44B:
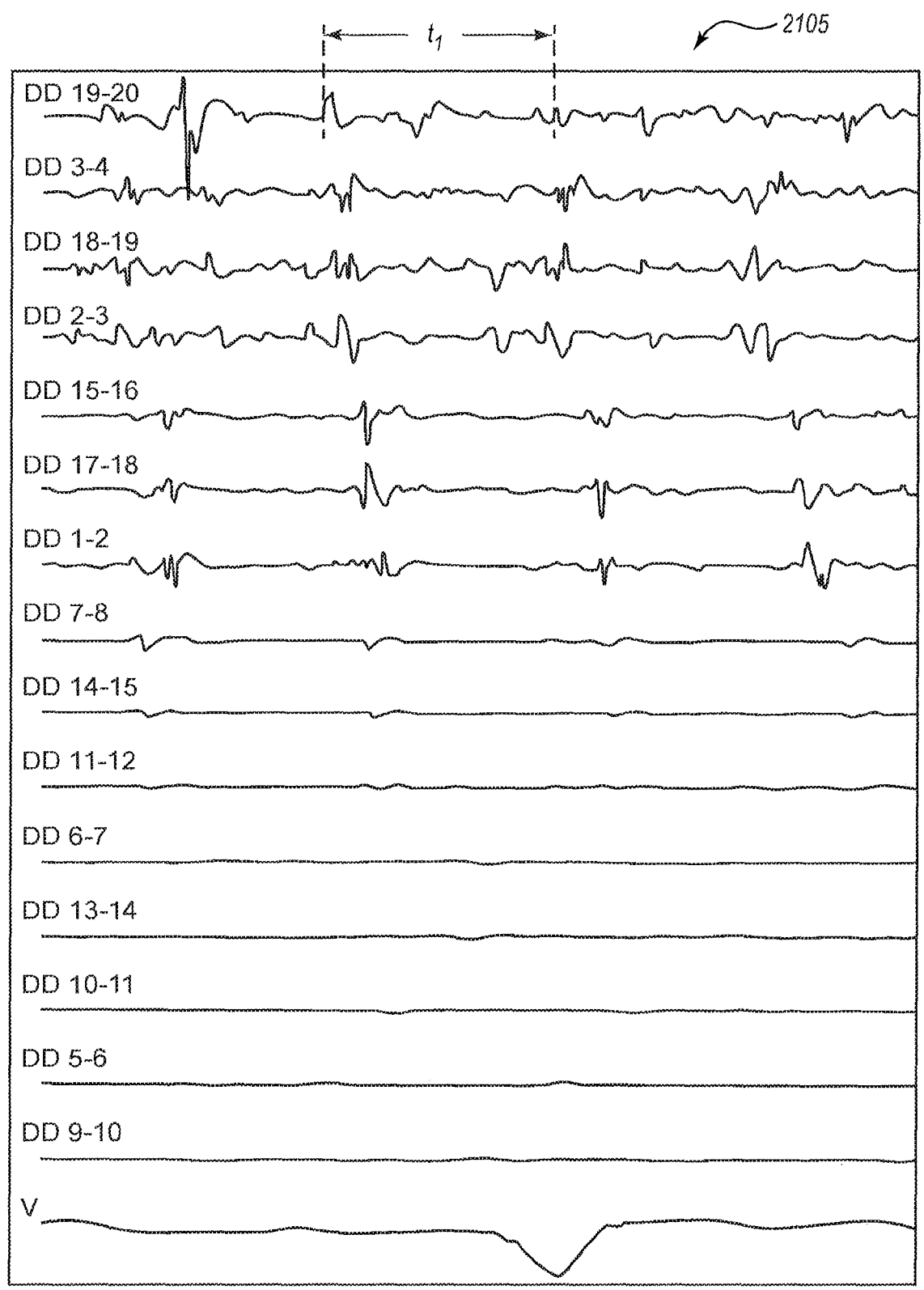
FIG. 44B is a plot that includes the electrograms from FIG. 44A in a rearranged format to demonstrate propagation of wavefronts from the driver.

The result of such a ranking algorithm is shown in the plot 2105 in FIG. 44B, in which the highest ranked electrogram is listed first, the next highest is listed second, and so on. Whereas in some procedures, the ranking is performed by a computer or is otherwise automated, in other procedures, the ranking may be done visually by a practitioner. In other or further instances, the ranking may involve some form of manipulation of the electrograms by a practitioner, such as by dragging and dropping or some other movement using, for example, peripheral computer controls or a touchscreen. Thus, a practitioner might also be capable of rearranging, sorting, or ranking the electrograms into the order shown in FIG. 44B.

As mentioned above, the frequency (or period) of the electrograms can factor into a ranking algorithm. For example, the shorter the period between successive wavefronts, the higher the weighting an electrogram may receive. Thus, it may be desirable for the shortest period electrograms to appear at the top of the plot 2105, which can aid in determining the location of a target portion of the atrial wall 2050 at which a primary driver is expected to be located. In the illustrated embodiment, the period $t_1$ between successive wavefronts is shown.

Based on the observation or calculation that wavefronts first appear in the region between the sensors S19 and S20 and then propagate away from this region, it can be determined that the target region is closest to that region of the cardiac wall 2050. In some instances, the region between S19 and S20 is treated as a sufficiently close approximation as to the location of the driver 2030. Accordingly, the procedure may identify that location as the target spot.

In other embodiments, further calculations or observations can be conducted to conclude that the target area, although close to the position between the sensors S19 and S20, is actually between the branches that include the sensors S17, S18, S19, S20 and the sensors S1, S2, S3, and S4. Thus an even closer approximation may be obtained by making the target area somewhere between the positions between the sensors S19 and S20 and the sensors S3 and S4. Further algorithms may be used to even more accurately interpolate the position of the driver 2030. The algorithms may take into account such factors as the relative positions of the branches of the sensor assembly 2000, the relative positions of the sensors 2002, the differences in time at which wavefronts reach the respective sensor regions, etc.

In the illustrated embodiment, a single driver 2030 is identified. In some instances, signals from the driver 2030 might appear at each of the sensing regions, such that the propagation of the wavefronts will be even more apparent than what is shown in FIG. 44B. However, as can be seen in FIG. 44B, no every sensing region has received a signal from the driver 2030. This can be due to one or more of a variety of reasons, such as poor sensor contact with the atrial wall 2050, contact with an area of the wall that is non-electrically conductive (e.g., due to a prior ablation), etc.

Once a target position for the driver 2030 has been determined, this position can be identified on a map or plot (e.g., a representative image, such as the image 191 discussed above) of the heart. In some instances, the identification can be used for subsequent ablation. For example, in some instances, detection of different driver positions takes place over a period of time, and once all such desired positions have been identified, focal ablation of specific positions that have the highest ranking, or likelihood of being primary drivers, then proceeds.

The identification may be of any suitable variety. For example, as discussed above, the identification may take the form of adding color to the three-dimensional plot. In some instances, three different colors may be used to identify driver regions of fast, medium, or slow frequencies, which may correlate with high, intermediate, and low likelihood of being primary drivers. Further discussion of identification procedures are provided above. In some instances, after a desired number of such driver positions have been identified, the ablation may then proceed, and in some instances, only the most likely candidates for primary drivers are ablated. Other systems for identifying and ablating are contemplated. Additionally, in various instances, the periods for what are considered fast, medium, and slow drivers may vary, such as from patient to patient. Accordingly, in some instances, the thresholds for what is fast, medium, or slow may be set according to a relative scale, as determined by the physiology of the patient.

Figure 45:
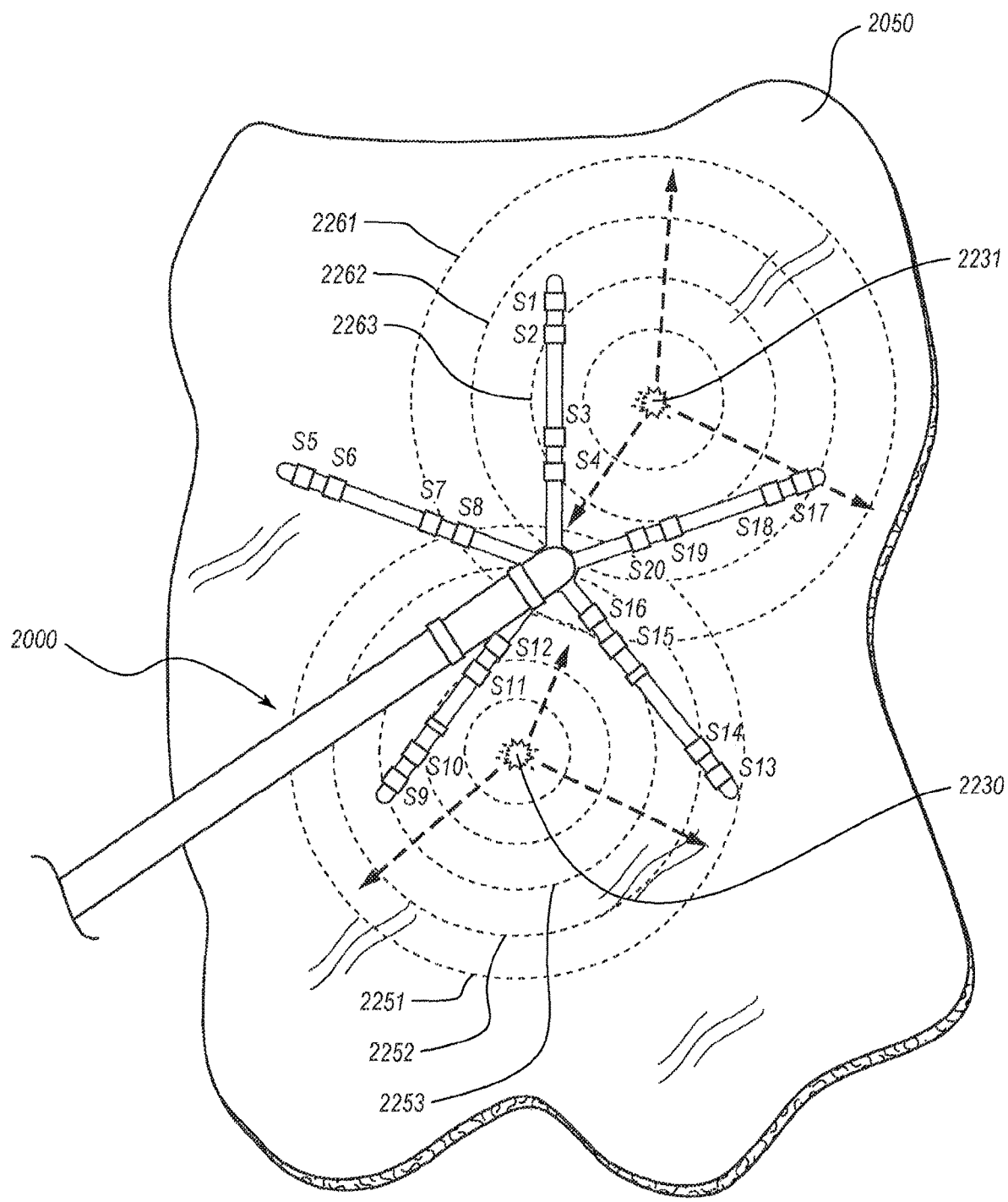
FIG. 45 is a plan view of an embodiment of a sensor assembly in the process of gathering electrograms from a portion of an atrial wall, wherein two separate drivers are within a sensing region of the sensor assembly.

FIG. 45 is a plan view of the sensor assembly 2000 in the process of gathering electrograms from another portion of the atrial wall 2050, wherein two separate drivers 2230, 2231 are within a sensing region of the sensor assembly. For example, the information gathering that is taking place in FIG. 45 can occur at a later time during the identification of possible drivers and prior to a focal ablation procedure. The driver 2230 provides wavefronts (e.g., 2251, 2252, 2253) at a higher frequency than the driver 2231 provides wavefronts (e.g., 2261, 2262, 2263).

Figure 46A:
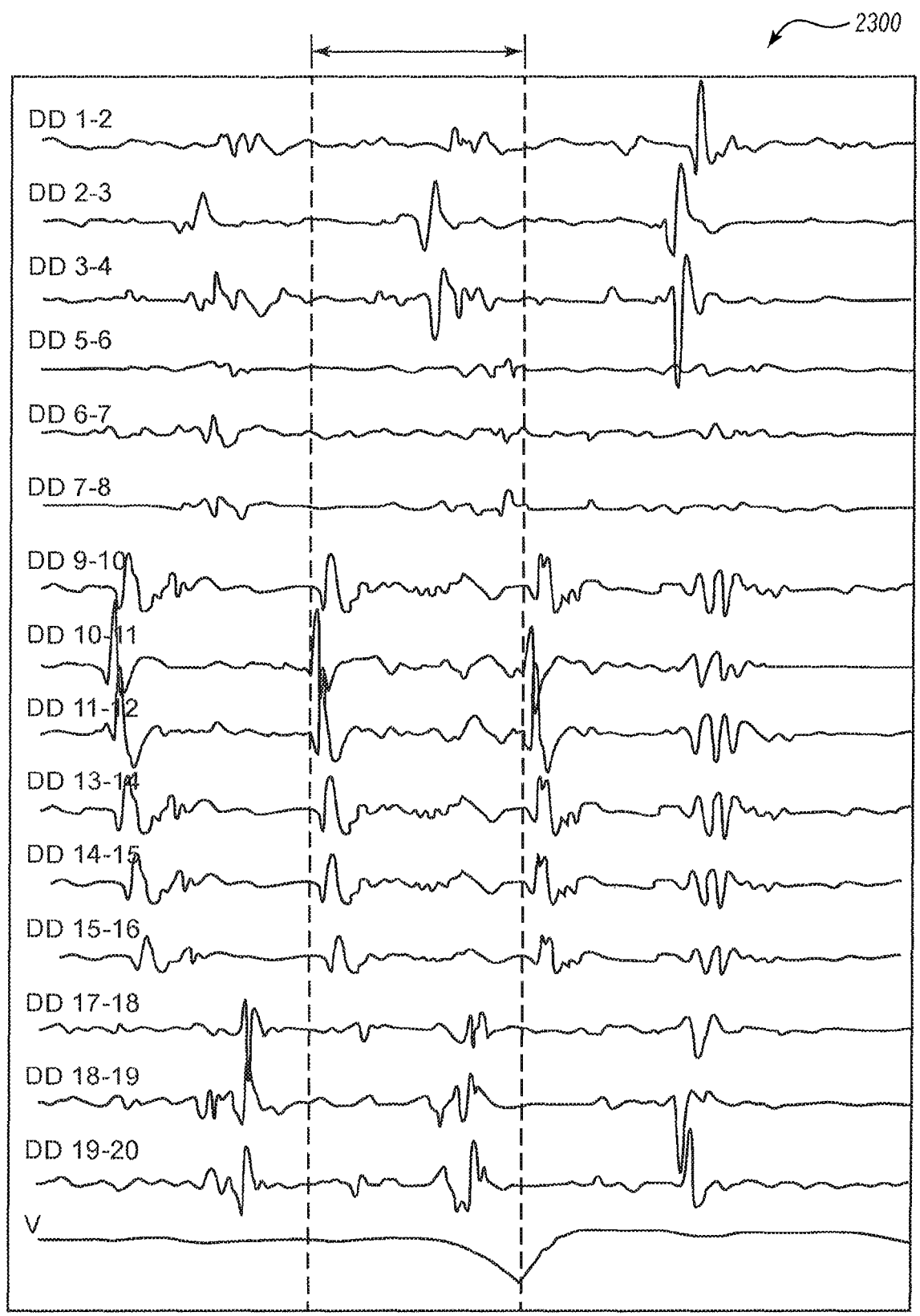
FIG. 46A is a plot that includes electrograms gathered via the sensor assembly and that also shows a base signal of the heart.

FIG. 46A is a plot 2300 that includes electrograms gathered via the sensor assembly 2000 and that also shows a base signal of the heart. Calipers (as shown by dashed vertical lines) may be provided to assist a practitioner in identifying a minimum period from among the electrograms, as well as an electrogram for which wavefronts appear first and then propagate onward to other sensed regions. In some arrangements, the calipers may be used instead of or in addition to sorting or rearranging the electrograms in the vertical dimension.

Figure 46B:
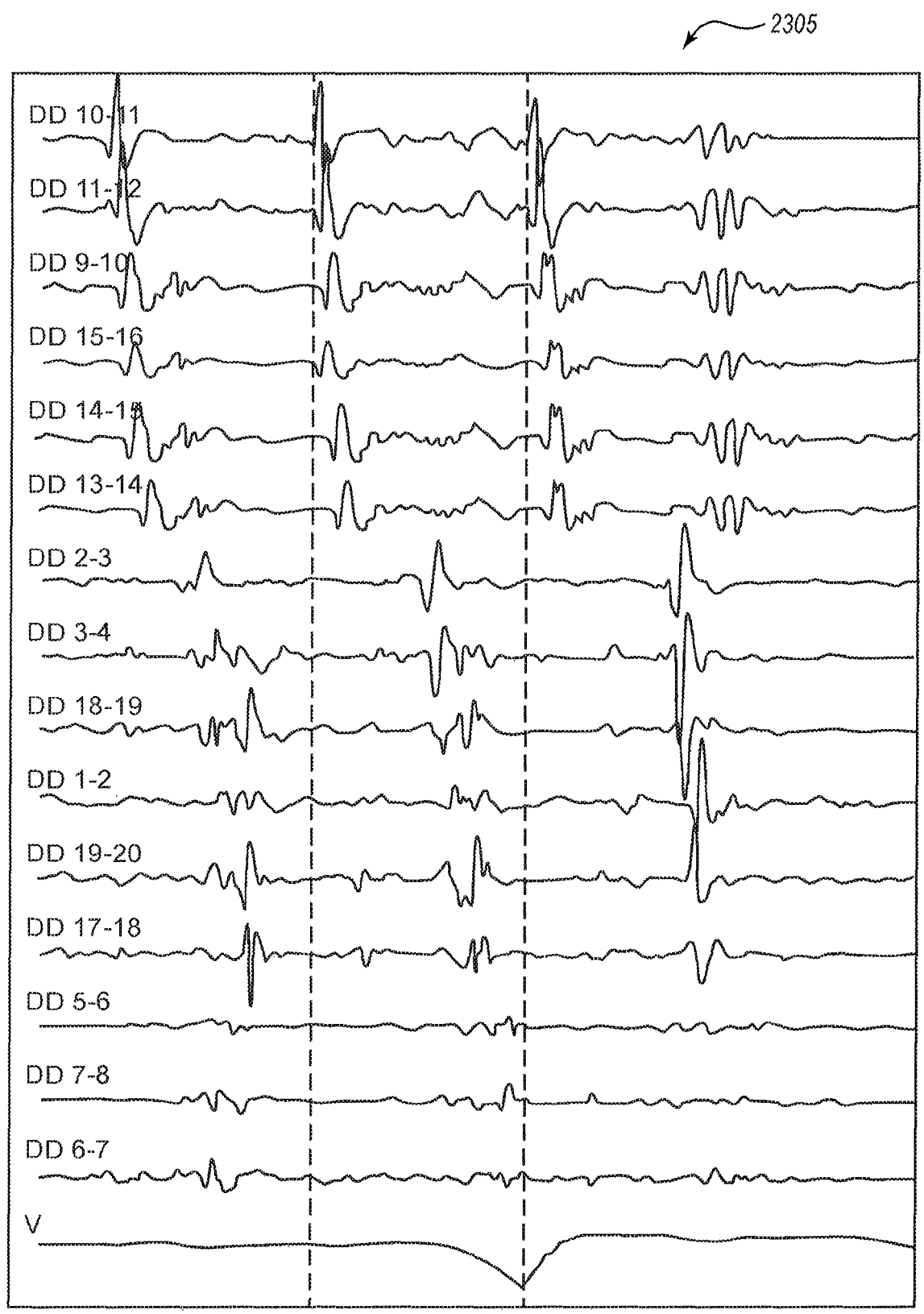
FIG. 46B is a plot that includes the electrograms from FIG. 46A in a rearranged format to demonstrate propagation of wavefronts from the drivers.

Such a sorting or ranking is shown in FIG. 46B. In the illustrated embodiments, the two drivers within the sensing area generate unique waveforms having nearly the same period, although the driver 2230 has a shorter period. In the illustrated sorting algorithm, the electrograms associated with the driver 2230 are higher along the vertical axis than, or stated otherwise, are ranked above, the electrograms that are associated with the driver 2231. This may result from the higher frequency of the driver 2230.

In some instances, a sorting algorithm may take into account various properties of the waveforms to conclude that multiple drivers are being sensed. For example, the two sets of waveforms have different overall shapes. The higher frequency waveform initiates with a small dip and then a large peak, for example, whereas the lower frequency waveform initiates with a small peak and then a large dip.

The plot 2305 shows multiple interacting drivers of distinct morphology and frequency. In DD 13-14, DD 14-15, a slow repetitive driver is noted by morphology and frequency with a simultaneous much more rapid, repetitive driver that has a distinct morphology and frequency.

As with identifying individual drivers, the target locations may be estimated approximately, or may be interpolated or otherwise calculated with a higher degree of accuracy. For example, in some procedures, one or more of the regions that are at or close to the regions between the sensors 10 and 11 and between the sensors 2 and 3 may be targeted, as the separate waveforms appear to generally propagate away from these regions.

Figure 47:
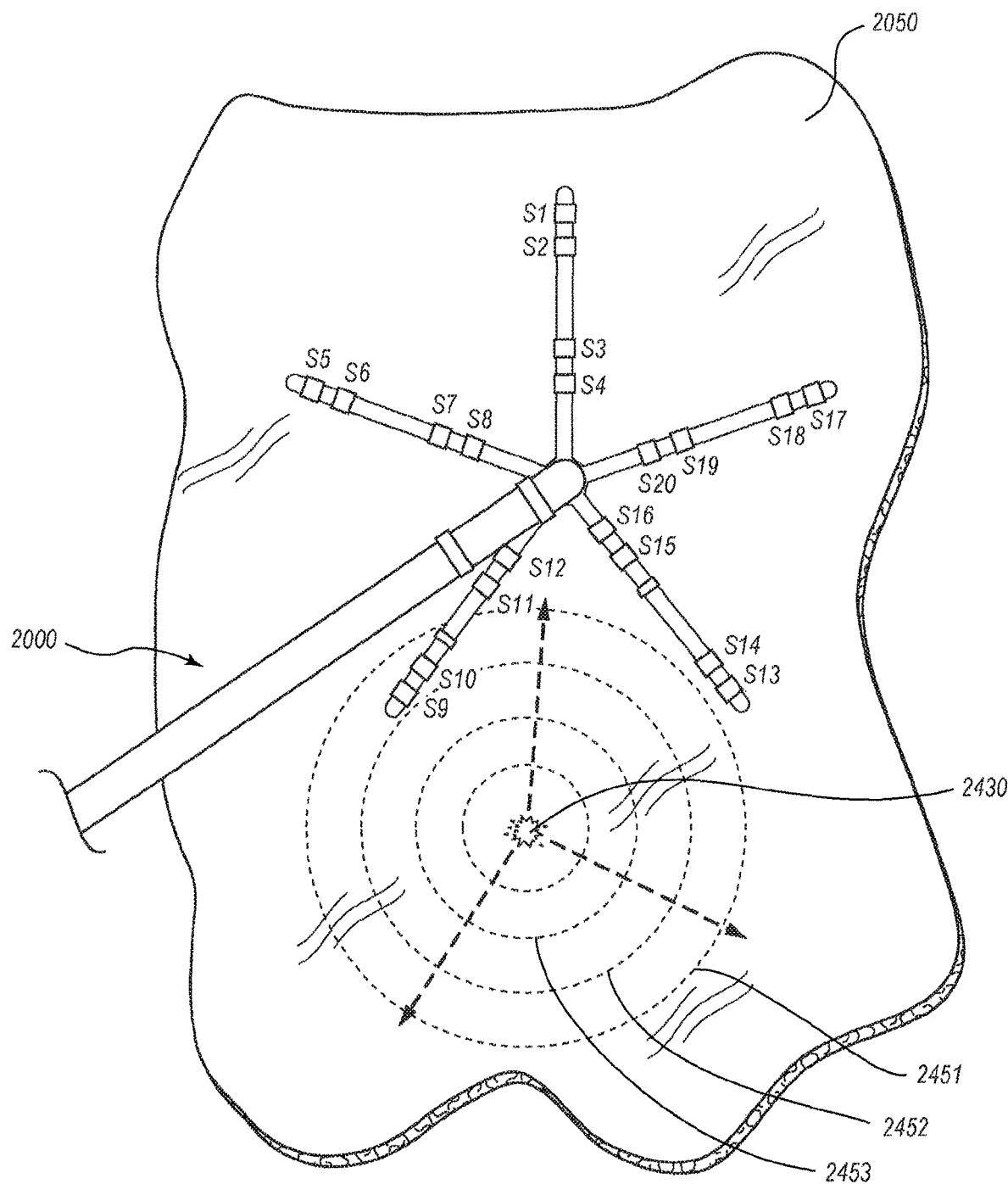
FIG. 47 is a plan view of an embodiment of a sensor assembly in the process of gathering electrograms from a portion of an atrial wall, wherein a driver is external to a sensing region of the sensor assembly.
Figure 48A:
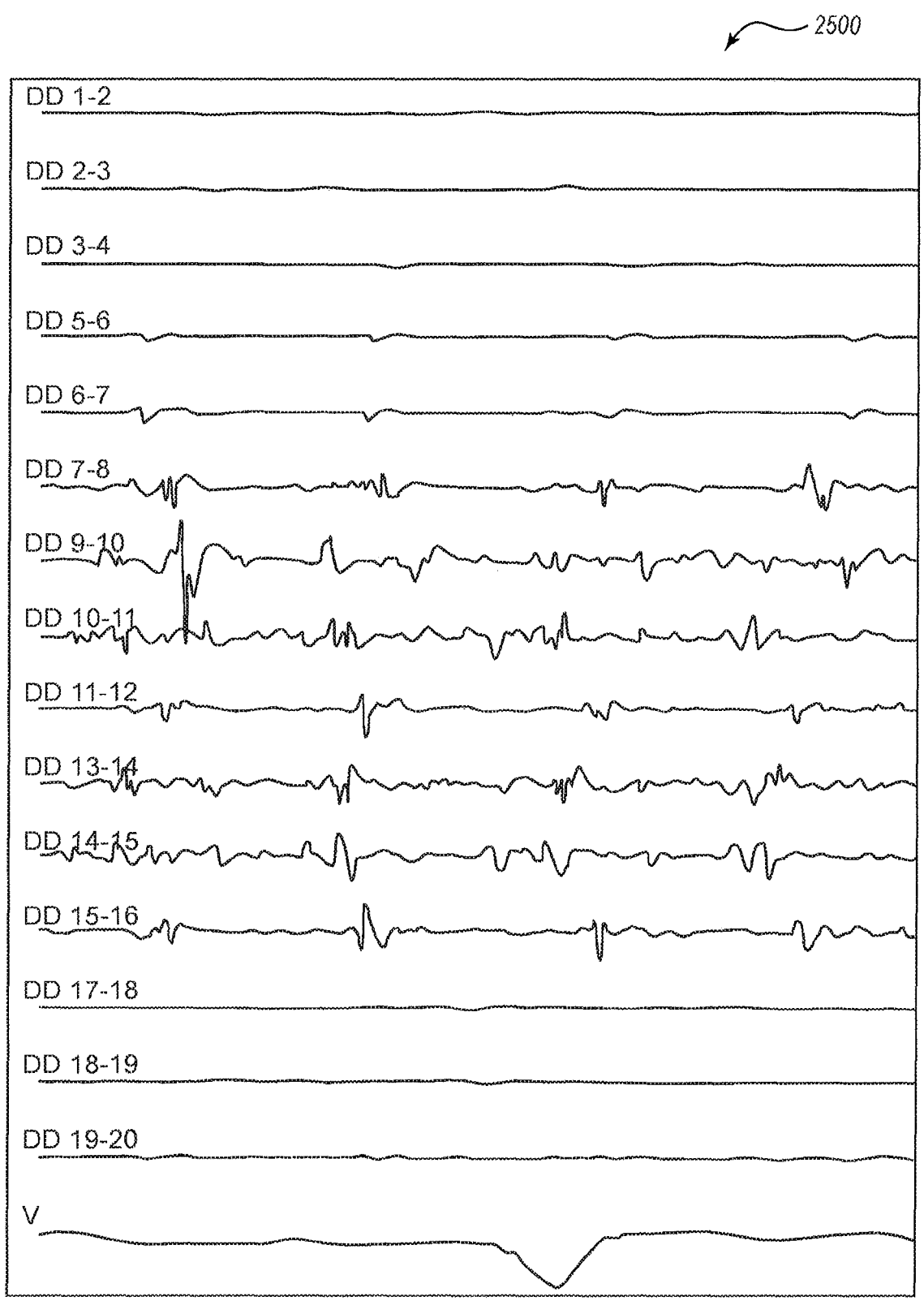
FIG. 48A is a plot that includes electrograms gathered via the sensor assembly and that also shows a base signal of the heart.
Figure 48B:
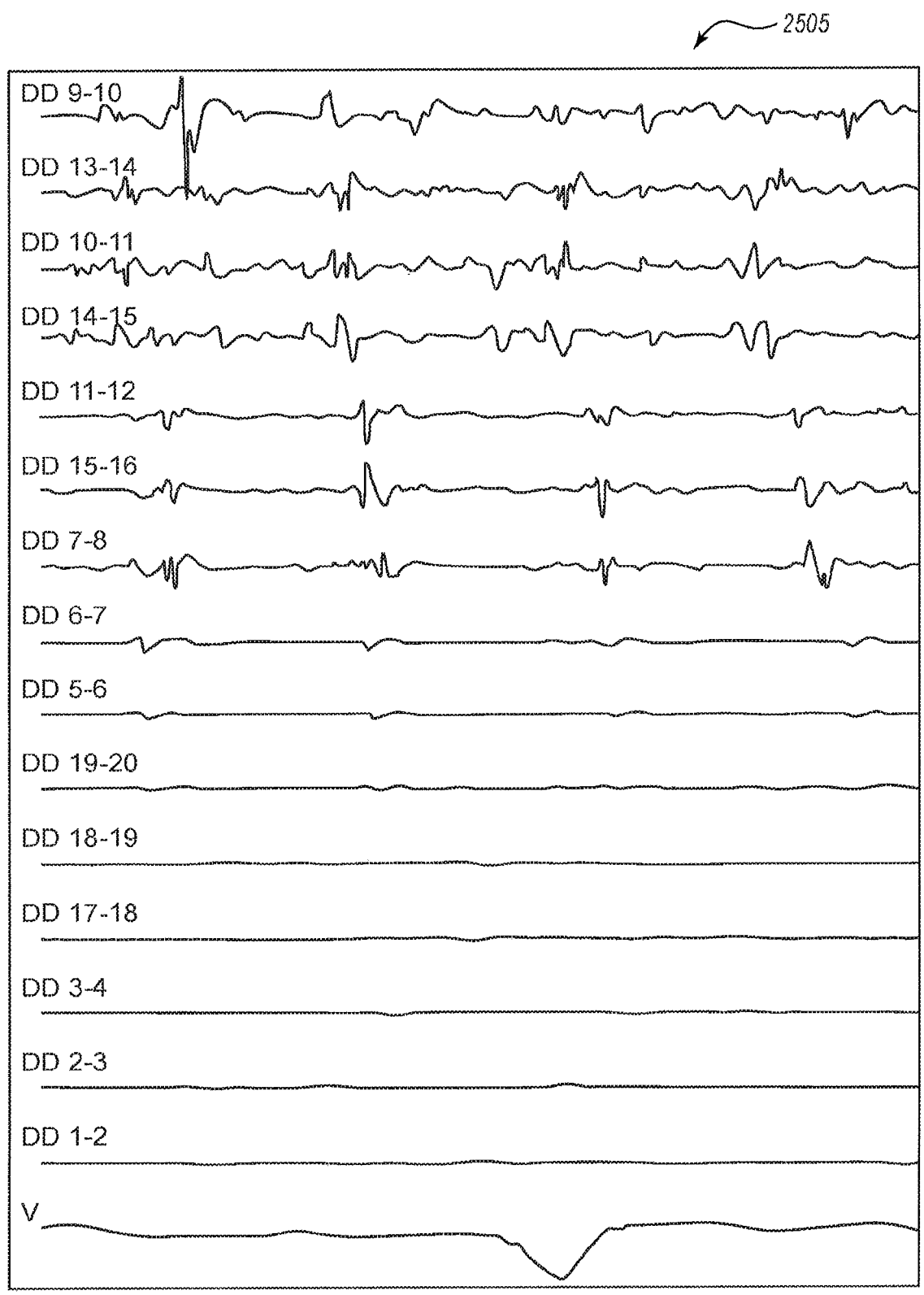
FIG. 48B is a plot that includes the electrograms from FIG. 48A in a rearranged format to demonstrate propagation of wavefronts from the driver.

FIG. 47 is a plan view of an embodiment of the sensor assembly 2000 in the process of gathering electrograms from another portion of the atrial wall 2050, wherein a driver 2430 is external to a sensing region of the sensor assembly. FIG. 48A is a plot that includes electrograms gathered via the sensor and that also shows a base signal of the heart. FIG. 48B is a plot that includes the electrograms from FIG. 48A in a sorted or rearranged format to demonstrate propagation of wavefronts from the driver.

In some embodiments, an algorithm may be used to determine that the driver 2430 is not between any of the branches of the sensor assembly 2000. Such algorithms may utilize time delay, sensor position, and/or other properties or variables of the sensed waves to determine an approximate or estimated location of the driver 2430. In other or further embodiments, the algorithm may provide a suggested direction for moving the distal end of the sensor assembly 2000 in order to bring the driver 2430 within the sensing area of the sensor assembly 2000 and determine more accurately the position of the driver 2430. In some embodiments, the suggested direction may occur on a display of the mapped heart. For example, the suggested direction may be depicted by an arrow or some other indicator on a display, which a practitioner can thus visualize and respond to in order to move the sensor assembly 2000.

Figure 49:
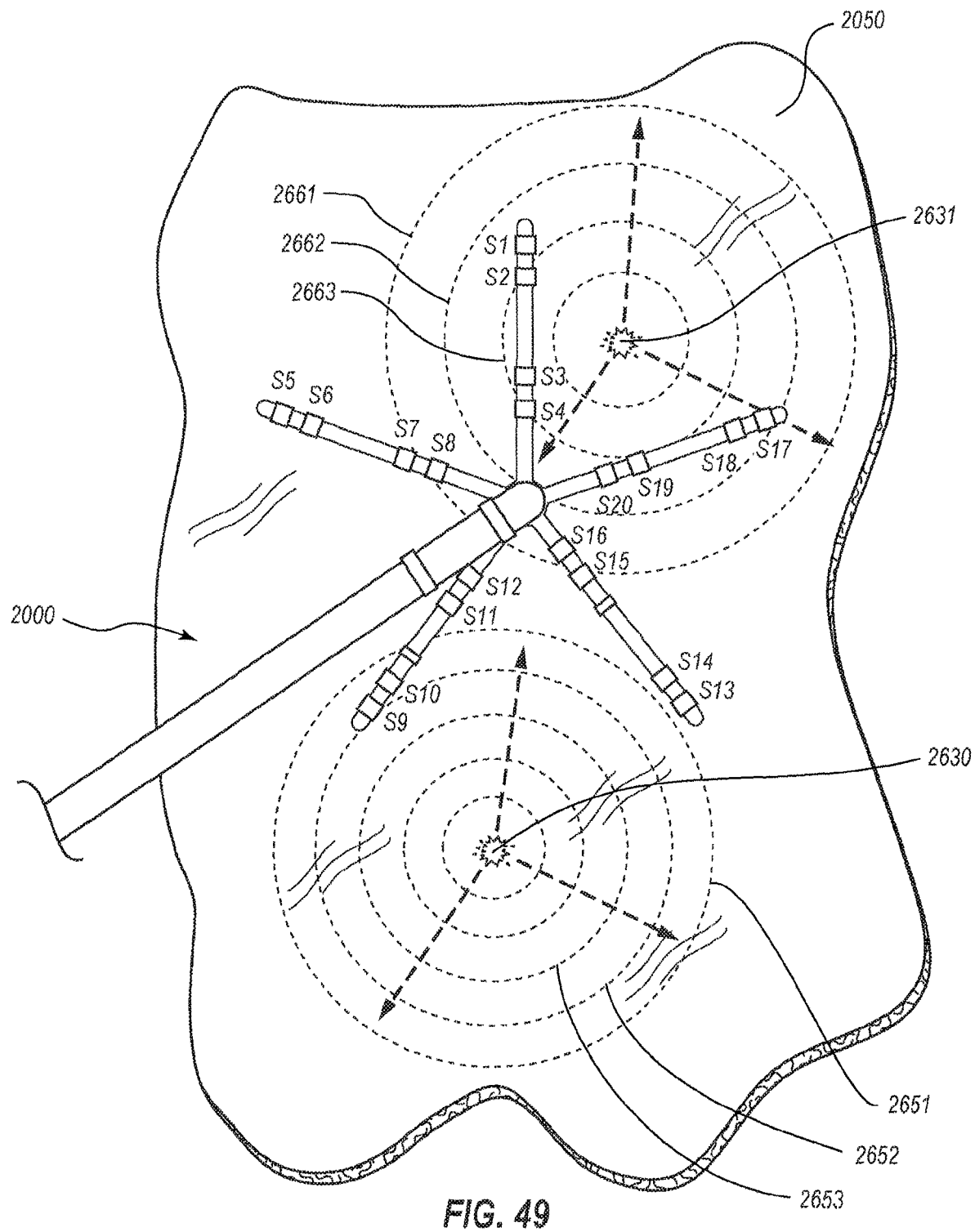
FIG. 49 is a plan view of an embodiment of a sensor assembly in the process of gathering electrograms from a portion of an atrial wall, wherein a first driver is at an exterior of the sensing region of the sensor assembly and a second driver is within the sensing region of the sensor assembly.
Figure 50A:
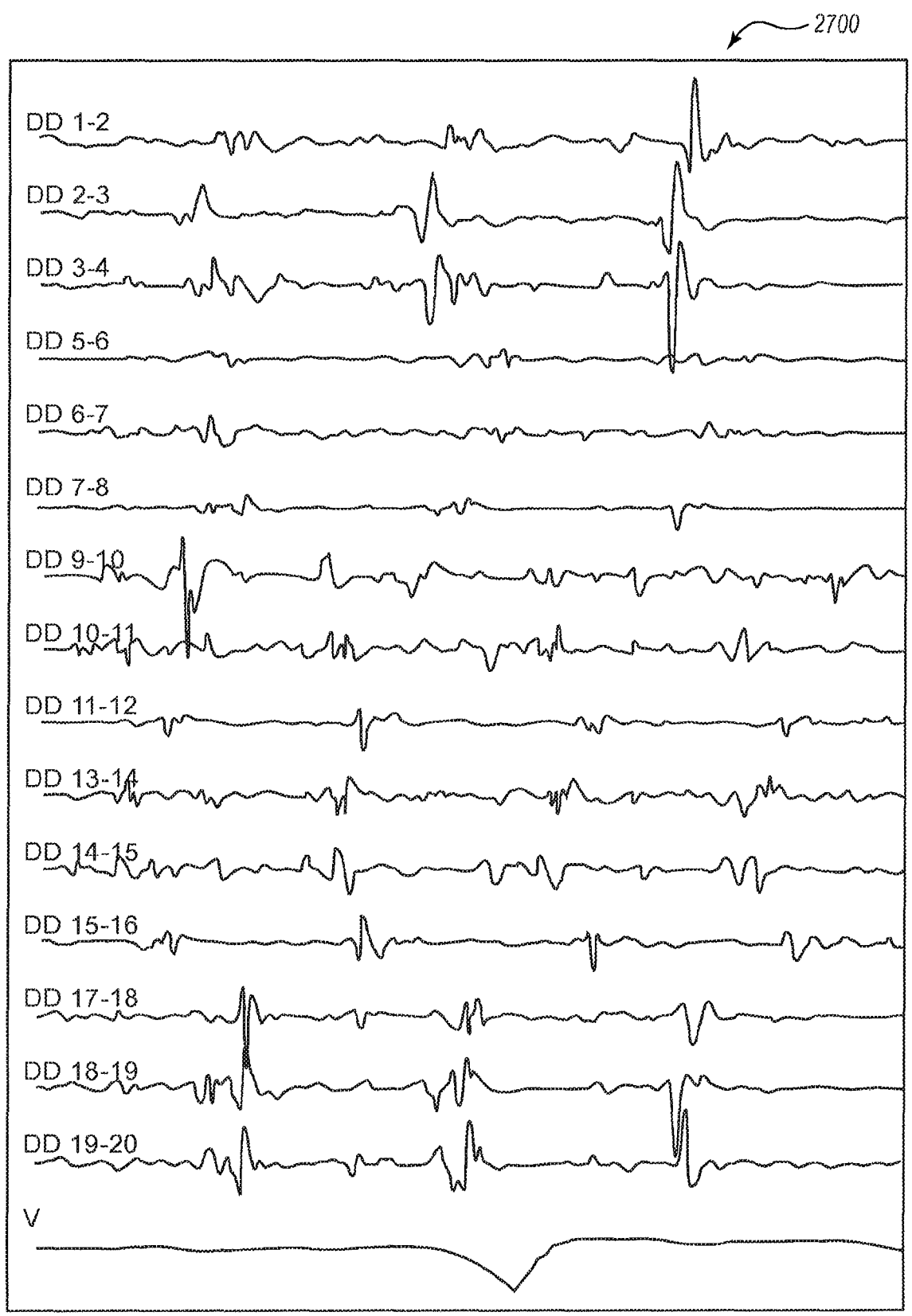
FIG. 50A is a plot that includes electrograms gathered via the sensor assembly and that also shows a base signal of the heart.
Figure 50B:
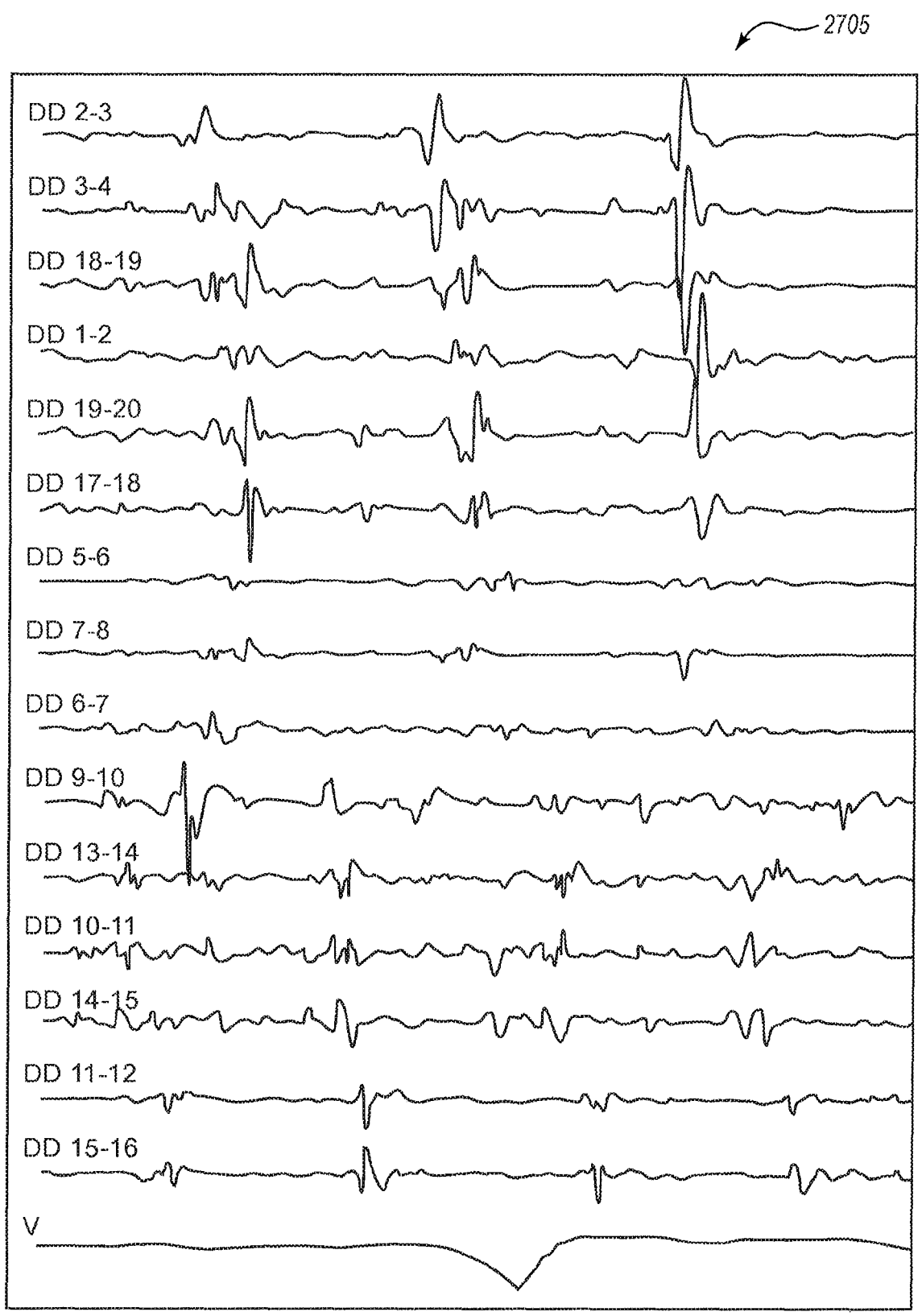
FIG. 50B is a plot that includes the electrograms from FIG. 50A in a rearranged format to demonstrate propagation of wavefronts from the drivers.

FIG. 49 is a plan view of the sensor assembly 2000 in the process of gathering electrograms from another portion of the atrial wall 2050, wherein a first driver 2630 is at an exterior of the sensing region of the sensor assembly 2000 and a second driver 2631 is within the sensing region of the sensor assembly 2000. FIG. 50A is a plot that includes electrograms gathered via the sensor assembly 2000 and that also shows a base signal of the heart. FIG. 50B is a plot that includes the electrograms from FIG. 50A in a ranked or rearranged format to demonstrate propagation of wavefronts from the drivers. Ranking or sorting of the waveforms, identification of target sites, and other procedures relative to the various sensed drivers can proceed in manners such as described above, particularly with respect to FIGS. 43-48B.

Figure 51:
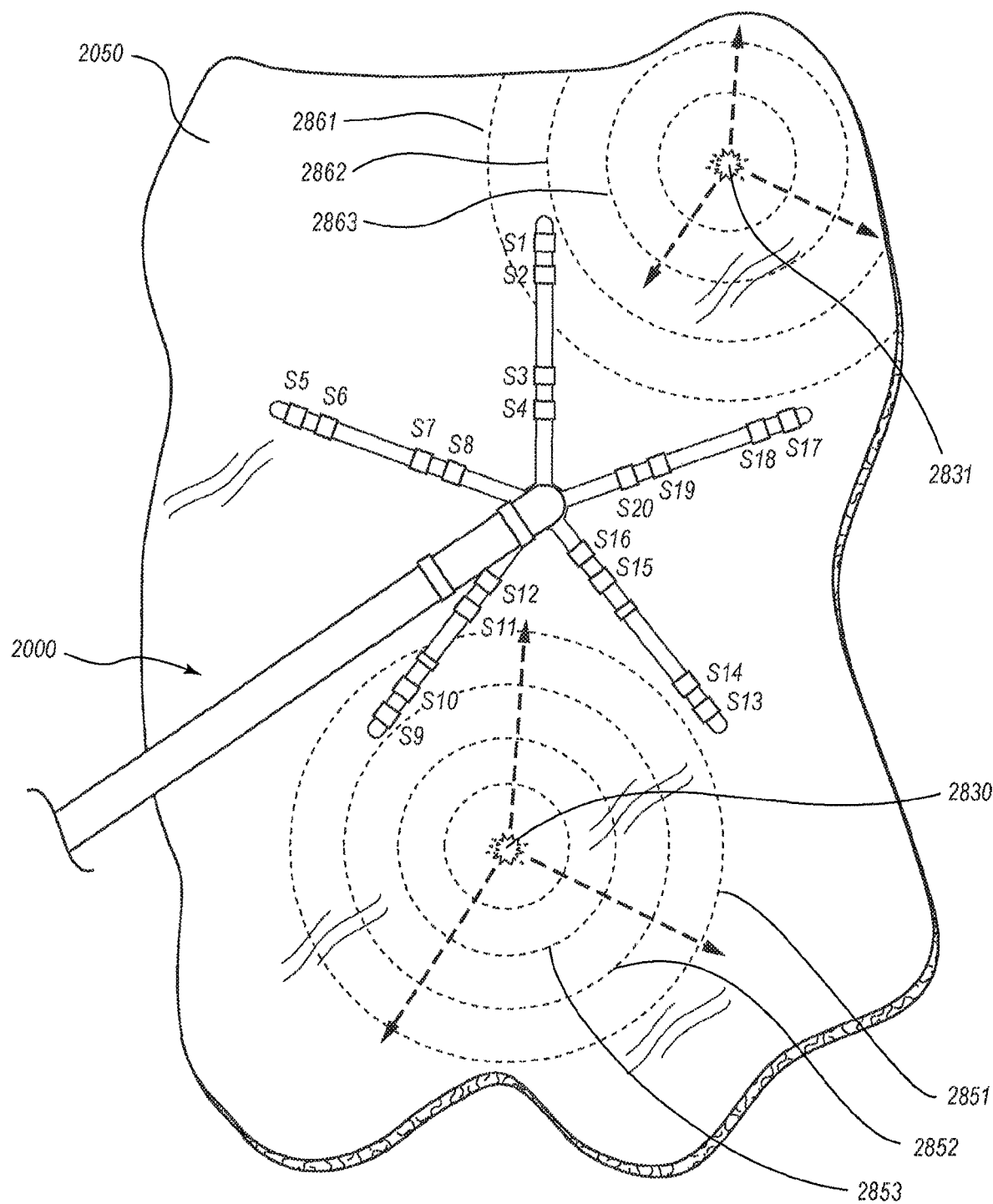
FIG. 51 is a plan view of an embodiment of a sensor assembly in the process of gathering electrograms from a portion of an atrial wall, wherein two drivers are near a sensing region of the sensor assembly but neither driver is within the sensing region.
Figure 52A:
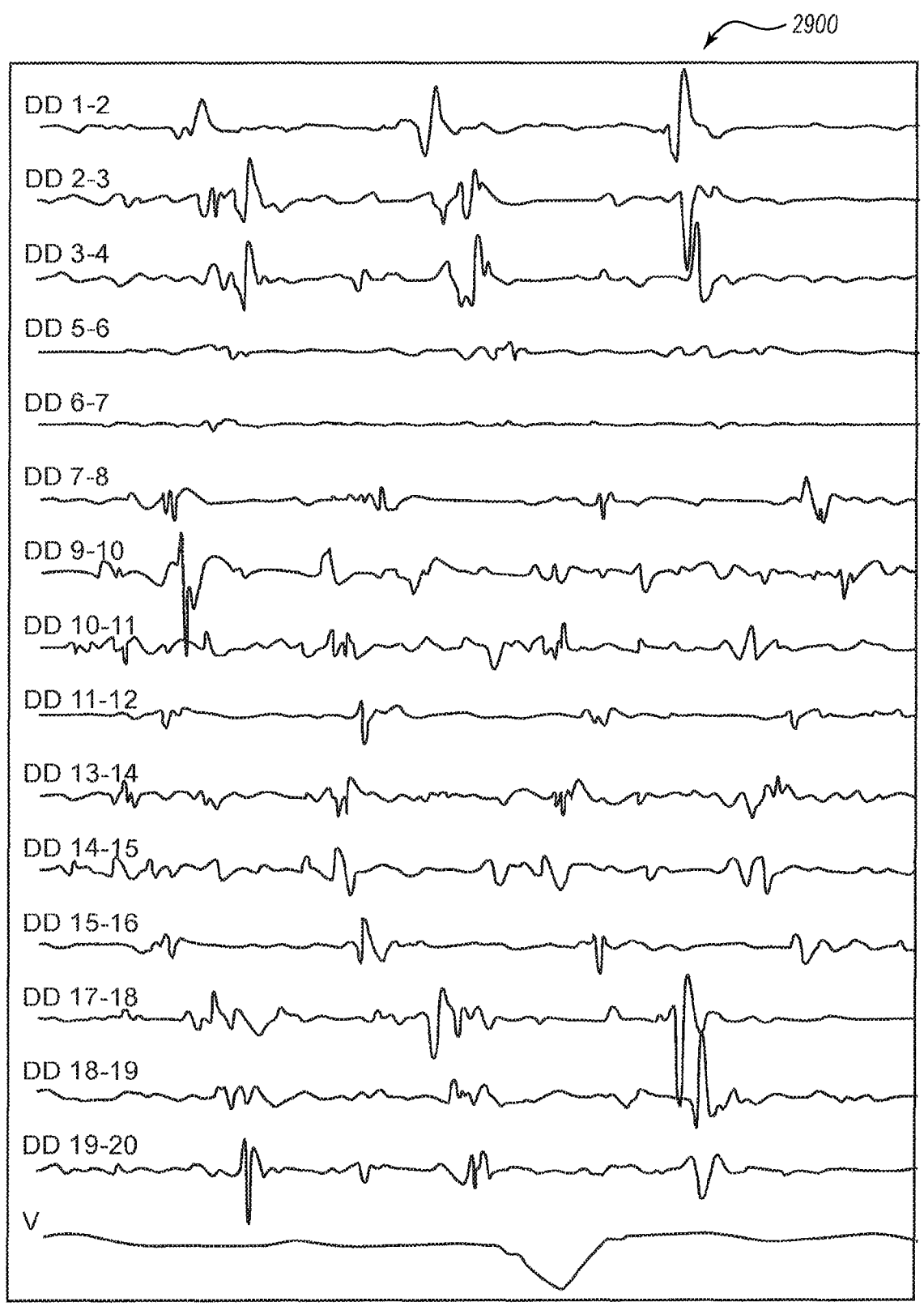
FIG. 52A is a plot that includes electrograms gathered via the sensor assembly and that also shows a base signal of the heart.
Figure 52B:
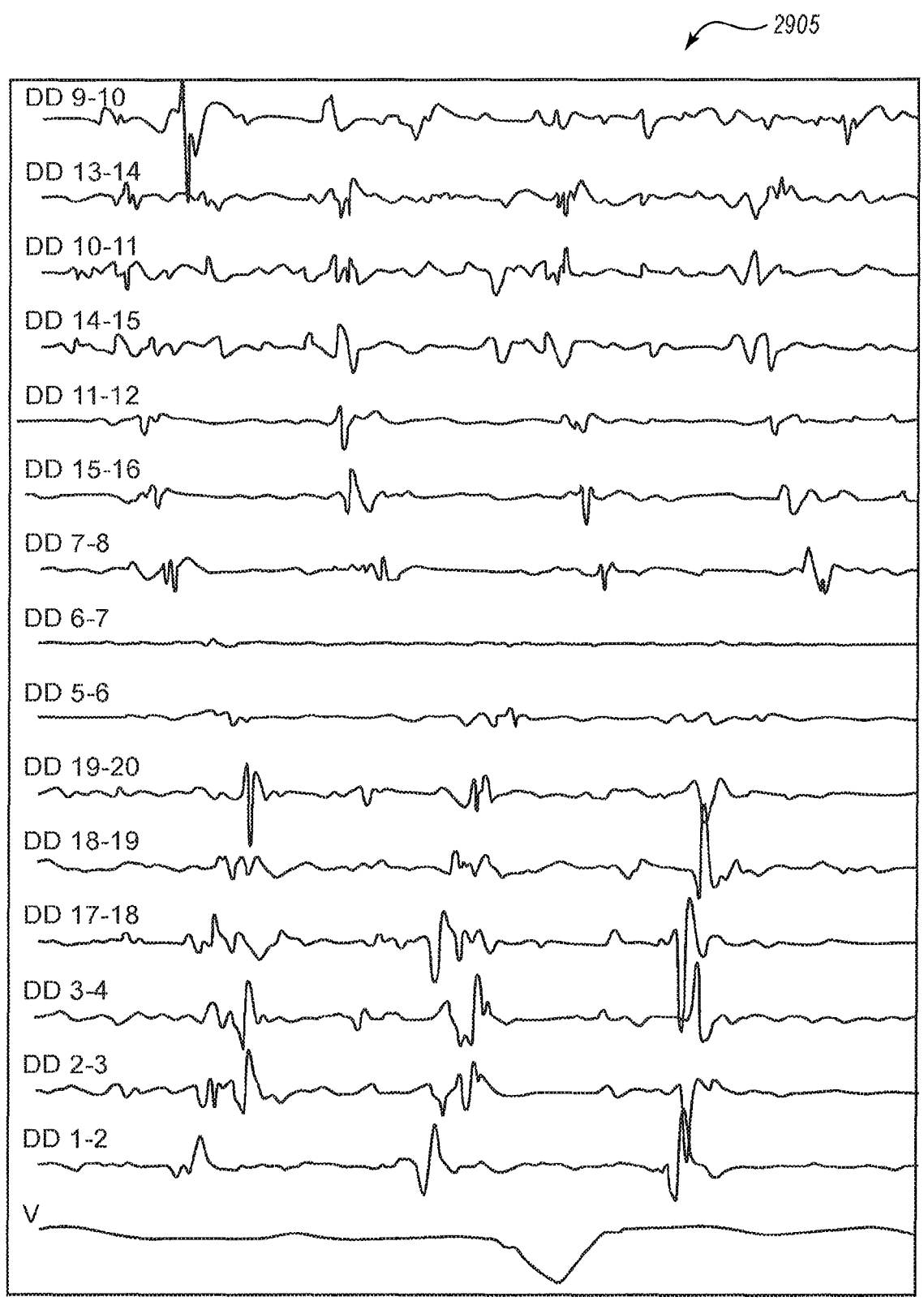
FIG. 52B is a plot that includes the electrograms from FIG. 52A in a rearranged format to demonstrate propagation of wavefronts from the driver.

FIG. 51 is a plan view of the sensor assembly 2000 in the process of gathering electrograms from another portion of the atrial wall 2050, wherein two drivers 2830, 2831 are near a sensing region of the sensor assembly, but are outside of the sensing region. FIG. 52A is a plot that includes electrograms gathered via the sensor and that also shows a base signal of the heart. FIG. 52B is a plot that includes the electrograms from FIG. 52A in a rearranged format to demonstrate propagation of wavefronts from the drivers. Ranking or sorting of the waveforms, identification of target sites, and other procedures relative to the various sensed drivers can proceed in manners such as described above, particularly with respect to FIGS. 47-50B.

Figure 53:
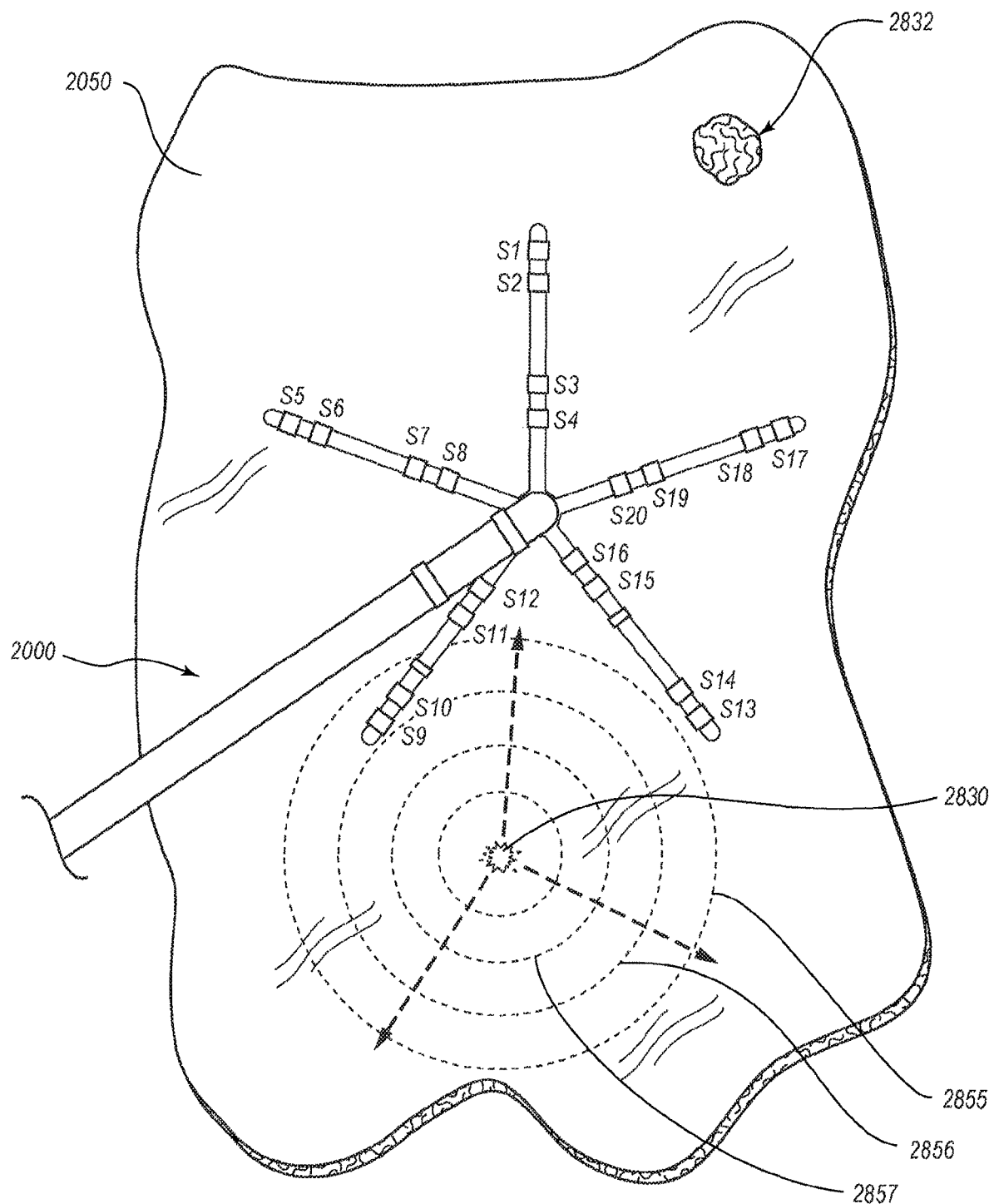
FIG. 53 is a plan view of an embodiment of a sensor assembly in the process of gathering electrograms from a portion of an atrial wall, wherein one driver is near a sensing region of the sensor assembly and another portion of the atrial wall that previously acted as a driver has been ablated and no longer emits wavefronts.
Figure 54A:
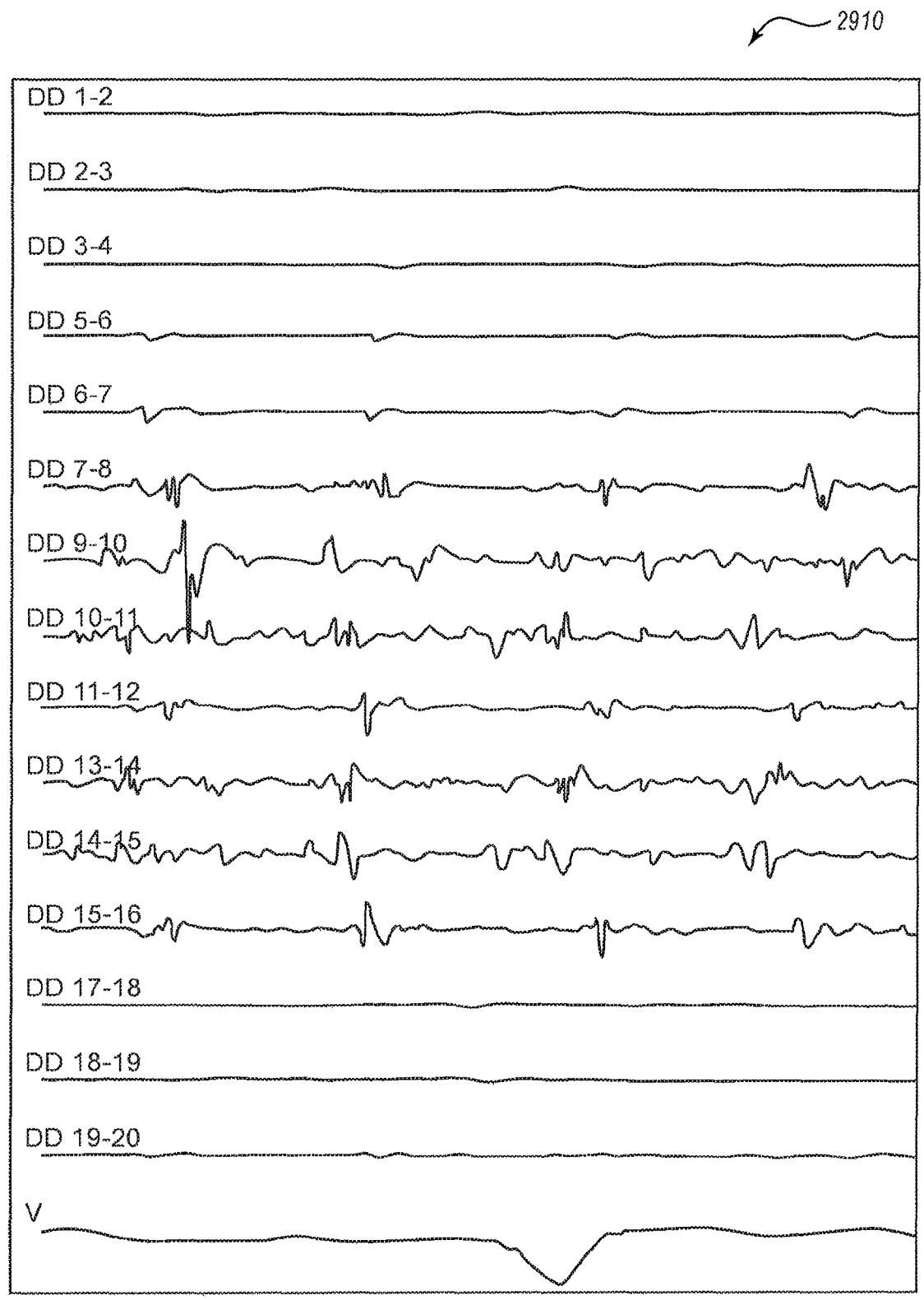
FIG. 54A is a plot that includes electrograms gathered via the sensor assembly and that also shows a base signal of the heart.
Figure 54B:
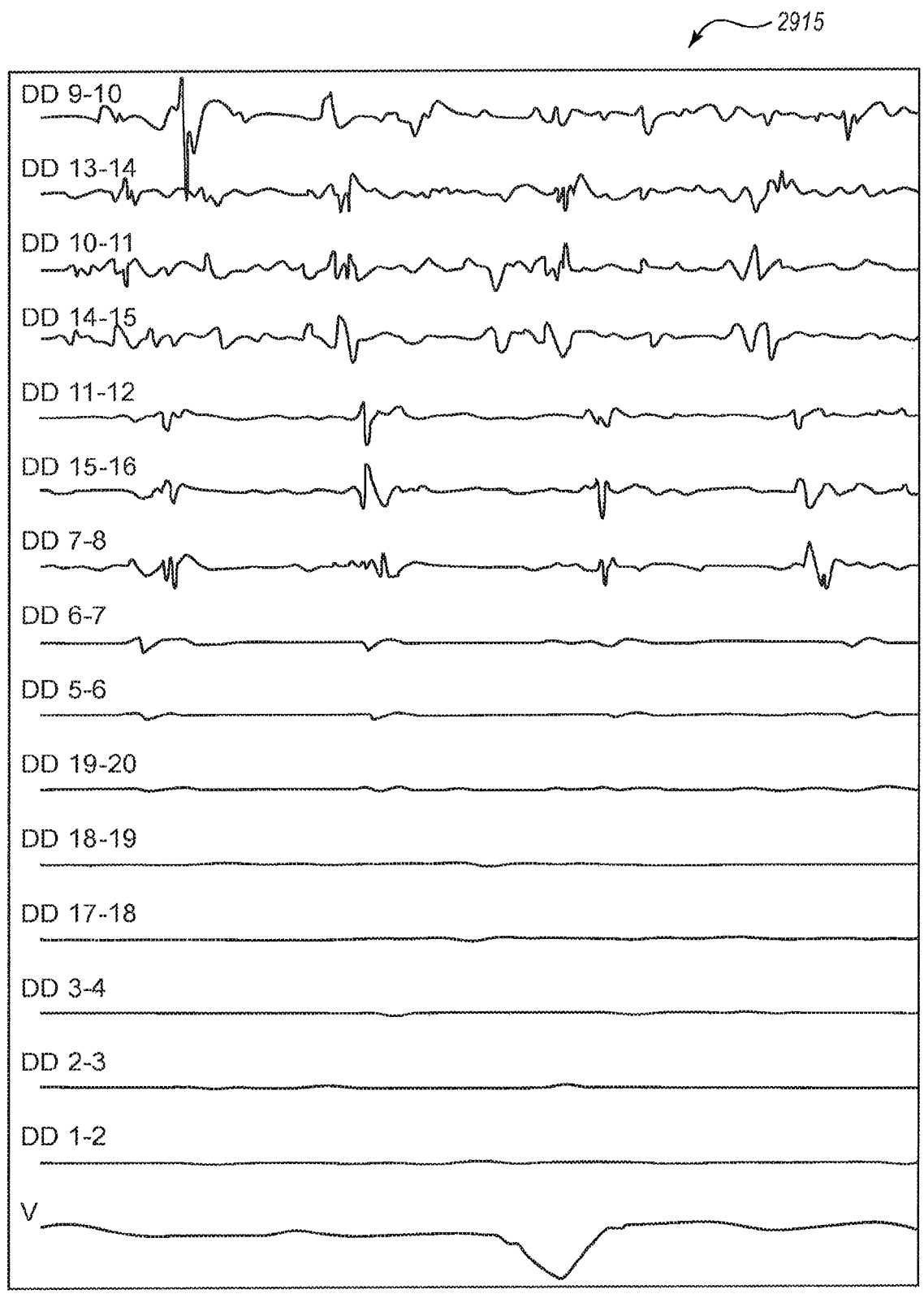
FIG. 54B is a plot that includes the electrograms from FIG. 44A in a rearranged format to demonstrate propagation of wavefronts from the driver.

FIG. 53 is a plan view of an embodiment of a sensor assembly in the process of gathering electrograms from the same portion of the atrial wall 2050 that is shown in FIG. 51. The atrial wall 2050 is shown after an ablative procedure has been conducted to cease activity of the driver 2831. FIG. 54A is a plot that includes electrograms gathered via the sensor and that also shows a base signal of the heart. FIG. 54B is a plot that includes the electrograms from FIG. 54A in a rearranged format to demonstrate propagation of wavefronts from the driver 2830. Due to the continued presence of a driver, a further ablative procedure may be desired. It is noted that the driver 2831 shown in FIG. 51 had a lower frequency than the driver 2830, although their frequencies were about the same. As discussed above, however, in many instances, the drivers with the higher or highest frequencies will be ablated in a preliminary ablation procedure.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub routines or only a portion of a method illustrated in the drawings, such as a small subset of step, may be a separate method. Stated otherwise, some additional methods may include only a portion of the steps shown in a more detailed method.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112 ¶6. Embodiments of the invention in which an exclusive property or privilege is claimed are defined as follows.

The invention claimed is:

1. A method of treating cardiac complex rhythm disorder in a patient, the method comprising:
   receiving an electrical base signal of a heart comprising a base signal frequency and a base signal waveform;
   simultaneously positioning a sensor system inside the heart of a patient while receiving a plurality of electrical signals from the sensor system, wherein positioning comprises identifying a source of repetitive aberrant electrical activity in the plurality of electrical signals and placing the sensor system such that the source is within a sensing region, wherein the sensing region is defined by a plurality of sensor locations that are in contact with a cardiac wall of the heart, wherein each electrical signal is detected at each of the plurality of sensor locations for at least one heartbeat, and wherein each electrical signal comprises an electrogram waveform;
   determining that the source of repetitive aberrant electrical activity is propagating in an outward direction from within the sensing region based on at least a timing and a frequency of the electrogram waveform of each electrical signal that is distinguishable from the base signal frequency, wherein the sensor system is positioned at a location where the source of repetitive aberrant electrical activity is disposed between a plurality of sensor locations in at least two different directions; and
   electrically isolating the source of repetitive aberrant electrical activity by relocating the sensor system and performing at least one focal ablation procedure inside the sensing region.

2. The method of claim 1, wherein a location of the source of repetitive aberrant electrical activity defines a target site within the sensing region and at least one focal ablation procedure is performed at the target site.

3. The method of claim 2, further comprising:
   repositioning the sensor system to another or the same sensing region that encompasses the target site after performing at least one focal ablation procedure and receiving a second plurality of electrical signals from the sensor system; and determining if the repetitive aberrant electrical activity has been eliminated from the electrical signals.

4. The method of claim 1, further comprising:
   generating a representative image of the heart of the patient; and
   identifying a target position on the representative image that corresponds to a location of the source of aberrant electrical activity.

5. The method of claim 1, further comprising identifying a target site of the cardiac wall, wherein identifying the target site comprises interpolating a location of the target site from the sensor locations on the cardiac wall.

6. The method of claim 1, wherein the at least one focal ablation procedure comprises encircling the source with a plurality of focal ablations.

7. The method of claim 1, wherein relocating the sensor system comprises removing the sensor system from its position inside the heart.

8. A method of treating cardiac complex rhythm disorder in a patient, the method comprising:
   receiving an electrical base signal of a heart comprising a base signal frequency and a base signal waveform;
   simultaneously positioning a sensor system inside the heart of a patient while receiving a plurality of electrical signals from the sensor system, wherein positioning comprises identifying a source of repetitive aberrant electrical activity in the plurality of electrical signals and placing the sensor system such that the source is within a sensing region, wherein the sensing region is defined by a plurality of sensor locations that are in contact with a cardiac wall of the heart, wherein each electrical signal is detected at each of the plurality of sensor locations for at least one heartbeat, and wherein each electrical signal comprises an electrogram waveform;
   determining that the source of repetitive aberrant electrical activity is propagating in an outward direction from within the sensing region based on at least a timing and a frequency of the electrogram waveform of each electrical signal that is distinguishable from the base signal frequency; and
   electrically isolating the source of repetitive aberrant electrical activity by performing at least one focal ablation procedure inside the sensing region.

9. The method of claim 8, wherein a location of the source of repetitive aberrant electrical activity defines a target site within the sensing region and at least one focal ablation procedure is performed at the target site.

10. The method of claim 9, further comprising:
    repositioning the sensor system to another or the same sensing region that encompasses the target site after performing at least one focal ablation procedure and receiving a second plurality of electrical signals from the sensor system; and
    determining if the repetitive aberrant electrical activity has been eliminated from the electrical signals.

11. The method of claim 8, further comprising:
    generating a representative image of the heart of the patient; and
    identifying a target position on the representative image that corresponds to a location of the source of aberrant electrical activity.

12. The method of claim 8, further comprising identifying a target site of the cardiac wall, wherein identifying the target site comprises interpolating a location of the target site from the sensor locations on the cardiac wall.

13. The method of claim 8, wherein the at least one focal ablation procedure comprises encircling the source with a plurality of focal ablations.

14. The method of claim 8, further comprising removing the sensor system from its position inside the heart prior to performing the at least one focal ablation procedure.

15. A method of treating cardiac complex rhythm disorder in a patient, the method comprising:
    positioning a sensor system inside the heart of a patient while receiving a plurality of electrical signals from the sensor system, wherein positioning comprises identifying a source of repetitive aberrant electrical activity in the plurality of electrical signals and placing the sensor system such that the source is within a sensing region, wherein the sensing region is defined by a plurality of sensor locations that are in contact with a cardiac wall of the heart, wherein each electrical signal is detected at each of the plurality of sensor locations for at least one heartbeat, and wherein each electrical signal comprises an electrogram waveform;

determining that the source of repetitive aberrant electrical activity is propagating in an outward direction from within the sensing region based on at least a timing and a frequency of the electrogram waveform of each electrical signal, wherein the sensor system is positioned at a location where the source of repetitive aberrant electrical activity is disposed between a plurality of sensor locations in at least two different directions;

electrically isolating the source of repetitive aberrant electrical activity by performing at least one focal ablation procedure inside the sensing region; and repositioning the sensor system to another or the same sensing region that encompasses the target site after performing at least one focal ablation procedure and receiving a second plurality of electrical signals from the sensor system; and determining if the repetitive aberrant electrical activity has been eliminated from the electrical signals.

16. The method of claim 15, wherein a location of the source of repetitive aberrant electrical activity defines a target site within the sensing region and at least one focal ablation procedure is performed at the target site.

17. The method of claim 15, further comprising:
generating a representative image of the heart of the patient; and
identifying a target position on the representative image that corresponds to a location of the source of aberrant electrical activity.

18. The method of claim 15, further comprising identifying a target site of the cardiac wall, wherein identifying the target site comprises interpolating a location of the target site from the sensor locations on the cardiac wall.

19. The method of claim 15, wherein the at least one focal ablation procedure comprises encircling the source with a plurality of focal ablations.

20. The method of claim 15, further comprising removing the sensor system from its position inside the heart prior to performing the at least one focal ablation procedure.

* * * * *